United States Patent
Nishioka et al.

[11] Patent Number: 6,025,873
[45] Date of Patent: *Feb. 15, 2000

[54] ENDOSCOPE SYSTEM PROVIDED WITH LOW-PASS FILTER FOR MOIRE REMOVAL

[75] Inventors: Kimihiko Nishioka, Hachioji; Naoki Hasegawa, Chofu; Katsuya Ono, Hino; Yutaka Tatsuno, Hachioji, all of Japan

[73] Assignee: Olympus Optical Co., Ltd., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/917,429

[22] Filed: Aug. 26, 1997

Related U.S. Application Data

[63] Continuation of application No. 08/380,578, Jan. 30, 1995, abandoned.

[30] Foreign Application Priority Data

| Apr. 7, 1994 | [JP] | Japan | 6-069601 |
| May 31, 1994 | [JP] | Japan | 6-118996 |

[51] Int. Cl.$^7$ .................... H04N 7/18; A61B 1/04
[52] U.S. Cl. ................ 348/72; 348/75; 348/342; 600/181
[58] Field of Search ............... 348/72, 73, 75, 348/71, 68, 65, 342, 360, 359, 340; 600/181, 182, 109; H04N 7/18

[56] References Cited

U.S. PATENT DOCUMENTS

| 4,178,611 | 12/1979 | Okano | 348/342 |
| 4,676,593 | 6/1987 | Adachi et al. | 350/96.26 |
| 4,845,554 | 7/1989 | Kimura et al. | 348/69 |
| 4,930,861 | 6/1990 | Okabe et al. | 348/359 |
| 4,977,450 | 12/1990 | Yokota | 348/72 |
| 4,988,171 | 1/1991 | Yokota | 600/181 |
| 4,989,959 | 2/1991 | Plummer | 359/640 |
| 5,392,067 | 2/1995 | Konno et al. | 348/72 |
| 5,444,574 | 8/1995 | Ono et al. | 348/342 |
| 5,471,343 | 11/1995 | Takasugi | 348/342 |

FOREIGN PATENT DOCUMENTS

| 44-1155 | 1/1969 | Japan . |
| 61-186919 | 8/1986 | Japan . |
| 1-284225 | 11/1989 | Japan . |
| 3-248695 | 11/1991 | Japan . |

OTHER PUBLICATIONS

Television Technical Paper, pp. 19–21; Jan. 1991.

*Primary Examiner*—Bryan Tung
*Attorney, Agent, or Firm*—Armstrong, Westerman, Hattori, McLeland & Naughton

[57] ABSTRACT

An endoscope system including a first hard endoscope which uses a relay lens as an image transmission optical system, a second hard endoscope which uses an image guide formed by a fiber bundle, and a TV camera which is mountable respectively on the first and second hard endoscopes and which is rotatable. The TV camera has built therein a CCD. An optical low-pass filter for removing moire even in case of being rotated is provided on an ocular part of the second hard endoscope.

6 Claims, 29 Drawing Sheets

FIG. 13
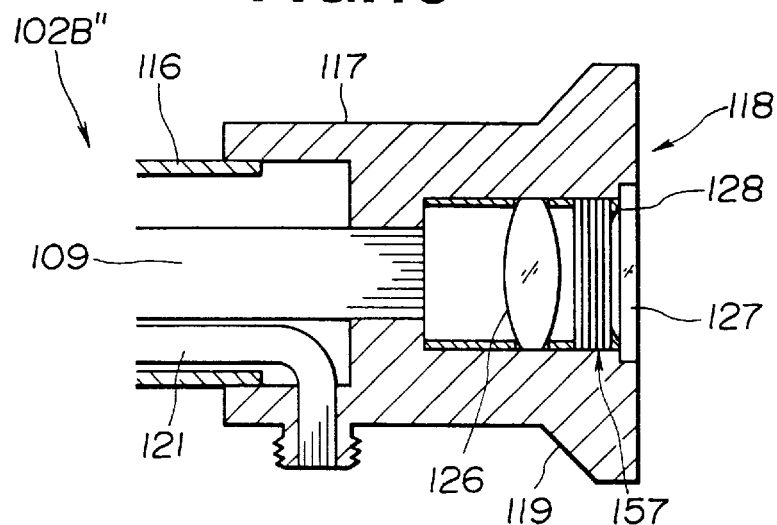
FIG. 14A   FIG. 14B
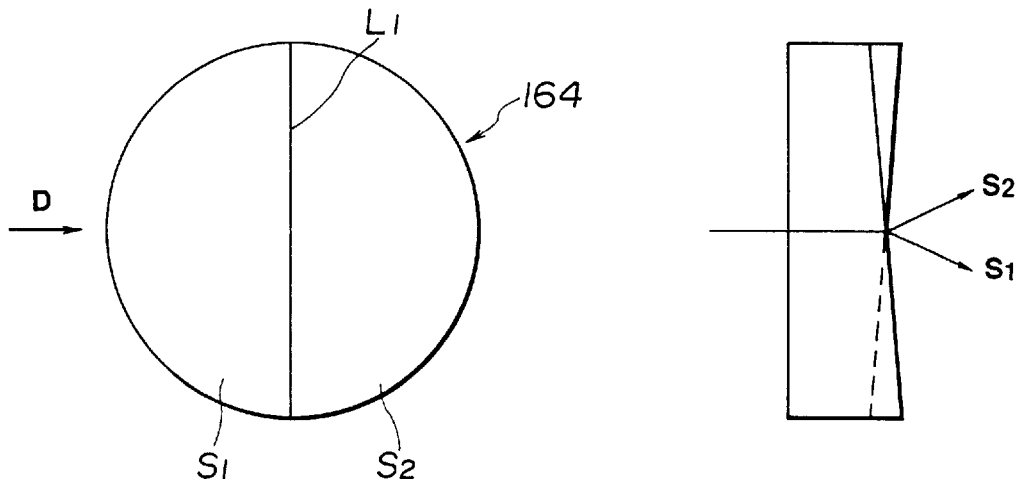
FIG. 15
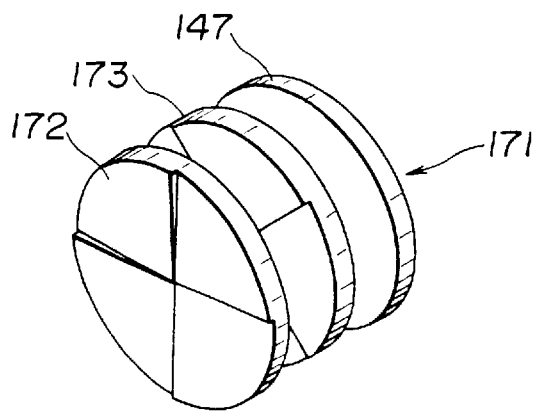

θa=2'40"

θb=2'40"
(=0.008rad)

$\theta = 2'$
$(= 0.00029 \text{rad})$

FIG.32A
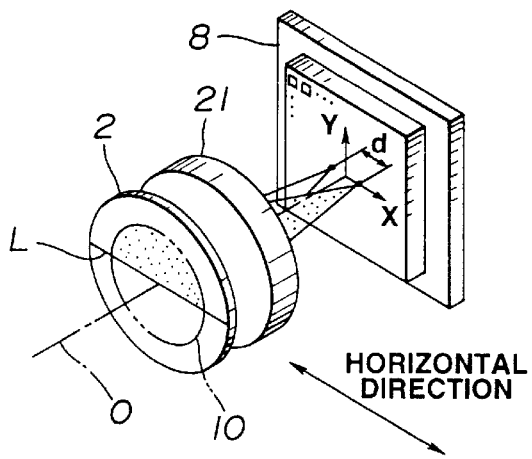
HORIZONTAL DIRECTION
FIG.32B
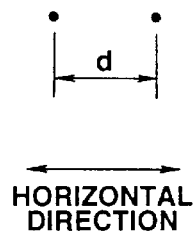
HORIZONTAL DIRECTION
FIG.33
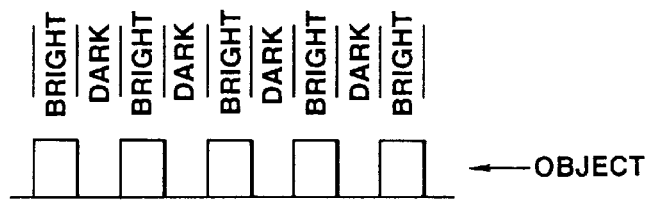
← OBJECT
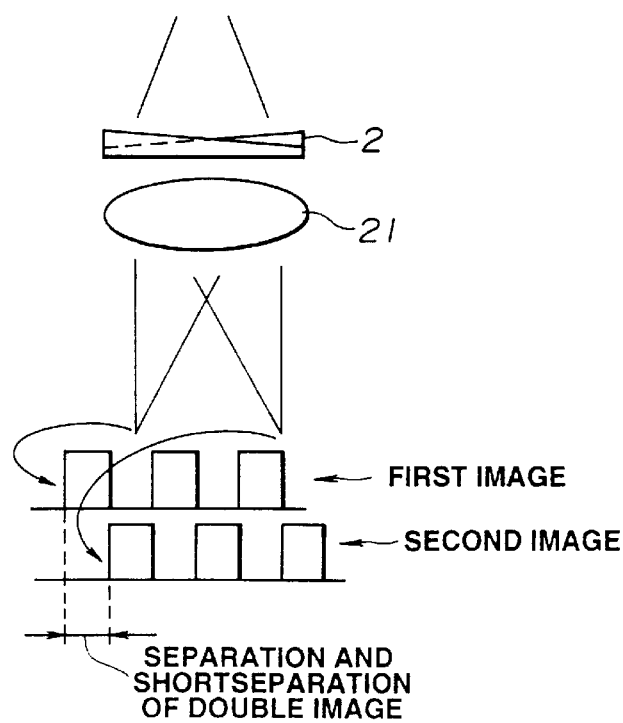
← FIRST IMAGE
← SECOND IMAGE
SEPARATION AND SHORTSEPARATION OF DOUBLE IMAGE

PORTION IN WHICH PLANAR SHAPE IS DISTURBED

BOUNDARY LINE

PORTION IN WHICH PLANAR SHAPE IS DISTURBED

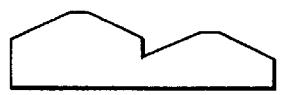
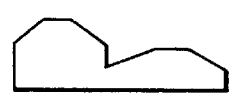
FIG.58A  FIG.58B  FIG.58C
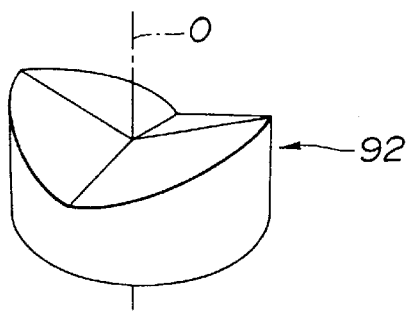
FIG.59
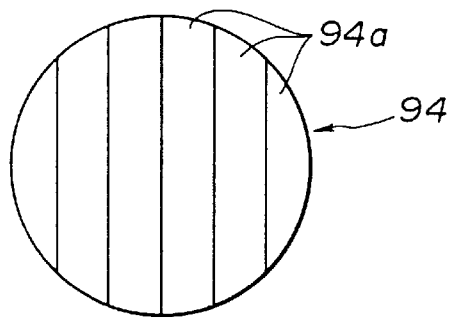
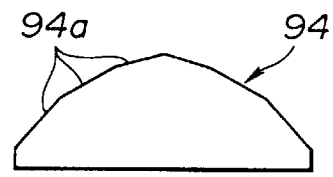
FIG.60A  FIG.60B
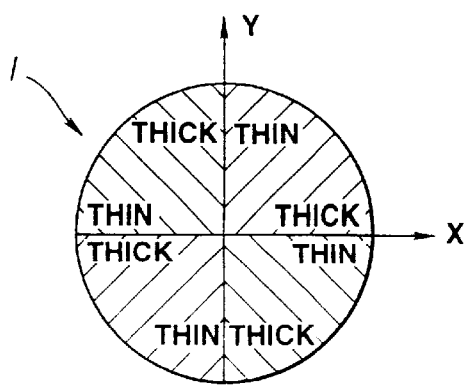
FIG.61

ENDOSCOPE SYSTEM PROVIDED WITH LOW-PASS FILTER FOR MOIRE REMOVAL

This application is a continuation of application Ser. No. 08/380,578 filed Jan. 30, 1995, now abandoned.

BACKGROUND OF THE INVENTION

1. Field of the Invention

The present invention relates to an endoscope system in which an endoscope for transmitting an image by fibers is provided with a low-pass filter for moire removal and which can use a common TV camera together with the endoscope which transmits the image by a lens or lenses.

2. Description of the Related Art

Endoscopes, particularly hard endoscopes, can be divided into two types including a lens relay type which uses the lenses consisting of a homogeneous or heterogeneous medium in an image transmitting optical system, and a fiber relay type which uses an image guide (hereinafter referred to as "IG"). In the case where high resolution is required, image transmission due to the lenses has been conducted. At this time, an optical low-pass filter (hereinafter referred to as "LPF") which has, normally, a double refraction plate of a degree of a single plate is inserted into an optical path of the TV camera which is used in combination with the hard endoscope, in order that the resolution is not injured, but only a pseudocolor is removed. Meanwhile, in the case where reduction in diameter is required for the hard endoscope, an IG is used. At this time, about three~four LPFs are inserted into the optical path of the TV camera which is used in combination with the hard endoscope, in order to reduce the moire which is generated by interference in cyclic structure or construction between the IG and an electronic image-pickup element (hereinafter referred to as "CCD").

In this manner, in the prior art, the TV camera which is provided with different LPFs has been used in accordance with the type of the image transmission optical system of the used endoscope.

Over against this, as an arrangement in which, even in case where the image transmission optical systems are different in type from each other, as the TV camera can commonly be used, there is an apparatus which is disclosed in Japanese Patent Unexamined Publication No. HEI 1-284225 (284225/1989). The apparatus is arranged such that LPFs each of which is formed by two~six quartz plates and which have different characteristics are prepared, and the LPFs which are inserted into the optical path of the TV camera in accordance with the combined endoscope can selectively be exchanged.

In this manner, the reason as to why the different LPFs are used in accordance with the type of the image transmission optical system is as follows:

The type which uses the relay lenses is arranged such that an image of an object is image-formed on the image pickup element by the lenses. Accordingly, the image of the object directly interferes with an array of picture elements or pixels of the image pickup element. Since, however, the frequency in which a fine frequency component similar to the repeating period of the picture element of the image pickup element is included in the object is relatively low, the generation of moire in the image is remarkably low. On the contrary, the arrangement which uses the image guide is such that an end face of the IG is imaged on the image pickup element. Since, however, the IG is an arrangement in which a multiplicity of fibers are bundled together, the IG includes such a plurality of frequency components that the IG interferes with the arrangement of the picture elements of the image pickup element. Specifically, the fibers have a core which transmits a light and a clad which does not transmit the light. Accordingly, the image on the end face of the fiber bundle in which the multiplicity of fibers are bundled is made to one in which a plenty of cores closely are arranged. The repeating patterns of the core interfere with the arrangement of the picture elements of the image pickup element, and remarkable moire is generated in the TV image. Accordingly, the different LPFs are required for the arrangement which uses the relay lenses and for the arrangement which uses the IG, in order to remove the moire.

By the way, there are various kinds of LPFs. However, a typical LPF has a double refraction plate such as a quartz plate or the like.

The double refraction plate has a property thereof which separates an incident light into a normal light and an abnormal light to output the same. Accordingly, if the double refraction plate is arranged at an adequate position in an image pickup light path, a double image of the object is formed on an image plane. An optical element for forming the double image effects to limit spatial frequency with respect to a direction in which the image is shifted. Specifically, the array having the repetitive period corresponding to an amount of shift of the two images is eliminated with reference to the direction in which the image is shifted. Accordingly, in the shifted direction, the spatial frequency response of the imaging optical system which includes the LPF becomes zero in the spatial frequency in accordance with the amount of shift of the image. The arrangement is such that such effects which limit the spatial frequency is utilized whereby the required number of quartz plates is arranged in a TV image pickup optical system, and an image separation direction of each plate is set adequately, to remove the moire.

In this case, the effects which limit the spatial frequency of the LPF are generated or occur only in a direction which separates a light ray retarding a single double-refraction plate. Accordingly, even if the same number of double refraction plates is combined with each other, the spatial frequency characteristics of the LPF are different from each other, depending upon how to set the light-ray separating directions. Thus, when the LPF is designed adequately, the number of double refraction plates and the light-ray separation direction are selected in accordance with the pattern of the arrangement of the picture element of the solid-state image pickup element, such as a CCD or the like, or the arrangement of the fibers of the IG.

Generally, a countermeasure against the moire which is generated by the interference between the IF and the CCD is dealt with by the fact that the LPF is provided on the side of the TV camera. A separation direction of a point due to the LPF has been designed on the assumption that the positional relationship which is fixed with respect to a scanning direction on a CCD face or plane is held or retained.

In recent years, diffusion or popularization of the surgery operations which use endoscopes abruptly increases the use of hard endoscopes in a surgical range or region. Further, almost all of the observation configuration or form in the range of surgery is image observation due to the TV monitor. Moreover, there are frequently forced the necessities that, during the operation, the hard endoscope of lens relay type which transmits the image by the lenses and the hard endoscope of fiber relay type which transmits the image by the fibers are selectively used. For this reason, in recent years, there has been an increased need for endoscope systems which can be used in such a manner that the aforesaid both types of hard endoscopes are connected to the same TV camera increase.

In the case where the LPFs of a degree of three~four are inserted into the optical path of the TV camera, the hard endoscope of lens relay type causes a decrease of resolution thereof. Meanwhile, in the case where only the LPF having a degree of one is inserted into the optical path of the TV camera, the moire is generated when used in combination with the hard endoscope of fiber relay type.

In an apparatus disclosed in Japanese Patent Unexamined Publication No. HEI 1-284225 (284225/1989), the LPF on the side of the TV camera must be replaced each time the hard endoscope is replaced, which causes problems when in use. In a surgical operation, many treatment tools must be treated or handled other than the endoscope. Thus, the prompt countermeasure must be taken during the operation. Accordingly, all actions which are time-consuming must be removed or excluded.

At present, however, it is extremely difficult to use the same TV camera between the endoscopes which have different image transmitting structures. Furthermore, a device which can realize the same has not yet been demonstrated.

Further, there is a need for observation, in the surgical operation, of the side of the abdomen or bauchseite which is always displayed correspondingly to an upper part of an image plane of a monitor. Particularly, in the case of the hard endoscope which observes a strabismus direction with respect to an insertion direction, the observation must be carried out while the scope is rotated during the operation. Along with this, the TV camera is frequently rotated to frequently conduct positional adjustment of the bauchseite which is displayed on the monitor. Specifically, for the aforesaid reason, the TV camera is universally rotated and is used with respect to a body of the endoscope, during the operation.

Meanwhile, since a conventional soft endoscope has a function of a wire angle or the like which can universally remote-operate the direction of a distal end thereof, the endoscope body has not been required to be rotated in the case of the strabismus. In this manner, it is peculiar to the hard endoscope to require the rotation of the endoscope body. Since the IG itself has flexibility, the IG has been mainly used in the soft endoscope, and it has been rare that the IG has been used in the hard endoscope. For this reason, it is not assumed that the hard endoscope of the fiber relay type is universally rotated and is used with respect to the TV camera, and this problem has conventionally not been considered. Accordingly, in the prior art, the relative positional relationship between the scanning direction on the CCD plane and the point separation direction of the LPF has been considered fixed. Any device on the assumption that the scanning direction is rotated universally has not yet been demonstrated.

In this manner, the endoscope system in which observation is conducted by the common TV camera, the TV camera can universally be rotated, and the moire is sufficiently suppressed in an optional rotational direction of the TV camera has not yet been demonstrated.

Although the conception is different, as an arrangement which is the closest to the arrangement of the endoscope system according to the present embodiment in an enforcement mode, there is an apparatus which is disclosed in JP-59-193416, corresponding to U.S. Pat. No. 4,676,593.

The apparatus is arranged such that, in order not to make prominent the mesh or network construction of the IG, the LPF having three quartz plates is provided in an ocular optical system, and the separation directions of the point due to the quartz plate are joined to each other every shifting of 60° in accordance with a transverse row or line (hexagonal density) of loading of the fiber.

However, in this apparatus, since the separation direction of the point is shifted every 60°, the separation strength of the point due to the quartz plate comes into $\frac{1}{3}$, and is not uniform. For this reason, the sufficient effects of moire removal cannot be acquired. Further, since it is not assumed that the TV camera is rotated, it is impossible to suppress the moire in an optional rotational direction. Moreover, consideration is not also paid to the adaptability of the TV camera.

Furthermore, as will be described on and after a tenth embodiment, the optical device or the image pickup device such as the endoscope device or the like in which the quartz plate is used to remove the moire increases in cost.

SUMMARY OF THE INVENTION

An object of the invention is to provide an endoscope system in which hard endoscopes of different image transmitting types such as a lens relay type and a fiber relay type are capable of being selectively mounted on the same TV camera, and, even if the TV camera is rotated through an optional angle with respect to a hard endoscope body, moire can sufficiently be removed.

Another object of the invention is to provide an optical device or an image pickup device which can remove moire or the like at low cost.

According to the invention, there is provided an endoscope system comprising:

a first endoscope body having first illumination-light output means for outputting an illumination light from the side of a distal end of an elongated first insertion part, a first object optical system provided on the side of the distal end of the first insertion part, for focusing into an image of an object which is illuminated by the illumination light, and a first image transmission optical system arranged with the first insertion part, and formed by the use of a lens which transmits the image to the rearward side of the first insertion part in a relay manner;

a second endoscope body having second illumination-light output means for outputting the illumination light from the side of a distal end of an elongated second insertion part, a second object optical system provided on the side of the distal end of the second insertion part, for focusing into the image of the object which is illuminated by the illumination light, a second image transmission optical system arranged within the second insertion part, and formed by the use of image guide fibers for image transmission, which transmits the image to the rearward side of the second insertion part, and low-pass filter means provided on the side of a rearward end of the second image transmission optical system, for optically removing moire which is generated in the case of using the image guide fibers for image transmission;

image pickup means detachably mounted on the side of a rearward end of one of the first and second endoscope bodies so as to be rotatable, having an imaging optical system for imaging an image which is transmitted by one of the first and second image transmission optical systems, and an image pickup element for conducting photoelectric conversion;

signal processing means for conducting signal processing with respect to the image pickup element; and image display means to which an image signal generated by the signal processing means is inputted to thereby display an image which is photoelectrically converted by the image pickup element.

Even if the second endoscope body or the image pickup means is rotated under a state in which the image pickup means is mounted on the second endoscope body, generation of moire can be suppressed by the low-pass filter means. Further, it is possible to avoid reduction in resolution in case where the image pickup means is mounted on the first endoscope body.

BRIEF DESCRIPTION OF THE DRAWINGS

FIG. 2 is a cross-sectional view showing structure or construction in the vicinity of an ocular part of a second hard endoscope under a state in which a photographing or radiographic adaptor is mounted;

FIG. 3 is a cross-sectional view showing structure in the vicinity of an ocular part of a first hard endoscope;

FIG. 4 is a view showing a quartz plate which forms an LPF which is provided on the second hard endoscope;

FIG. 5 is an explanatory view showing an array of a fiber of an IG which is used in the second hard endoscope;

FIG. 6 is a view showing an arrangement of an optical system in the vicinity of the ocular part of the second hard endoscope;

FIG. 7 is a characteristic view showing spatial frequency characteristics due to an LPF of the first embodiment;

FIG. 8 is cross-sectional view showing a TV camera device in a first modification of the first embodiment;

FIG. 11 is a characteristic view showing spatial frequency characteristics due to the LPF of the second embodiment;

FIG. 13 to FIG. 14B relate to a fourth embodiment of the invention, FIG. 13 being a cross-sectional view showing an arrangement in the vicinity of an ocular part of a second hard endoscope in the fourth embodiment;

FIG. 14A is a front elevational view showing a two-slant-face prism which forms an LPF in the fourth embodiment;

FIG. 14B is a side elevational view in which the two-slant-face prism is viewed from a direction indicated by an arrow D;

FIG. 15 to FIG. 17 relate to a fifth embodiment of the invention, FIG. 15 being a perspective view showing, in decomposition, an arrangement of an LPF in the fifth embodiment;

FIG. 16 is a front elevational view showing a four-slant-face prism which forms the LPF;

FIG. 17 is an explanatory view showing a separation pattern of a point due to the four-slant-face prism;

FIG. 19 is a front elevational view showing a double-sided four-slant-face prism which forms an LPF in the sixth embodiment;

FIG. 22 is a front elevational view of an LPF in the eighth embodiment;

FIG. 24 is an explanatory view for finding frequency fp of a fiber which forms an IG;

FIG. 25 is a view showing a color array of a mosaic filter which is used in a CCD;

FIG. 26 is an explanatory view showing the relationship between the frequency of the fiber which forms the IG and moire generation;

FIG. 27 is a view for the description of the relationship between the frequency of the fiber which forms the IG and moire generation;

FIG. 28A to FIG. 42 relate to a tenth embodiment of the invention, FIG. 28A and FIG. 28B being perspective views showing respectively one multiple slant face and the other multiple slant face of a double-sided multiple slant-face prism which is used in the tenth embodiment;

FIG. 30 is an arrangement view showing an endoscope apparatus according to a modification of the tenth embodiment;

FIG. 31 is an explanatory view of a pixel array of a solid-state image pickup element;

FIG. 32A is a perspective view showing an image pickup optical system of a television camera;

FIG. 32B is an explanatory view of function due to the single-sided multiple slant-face prism;

FIG. 33 is a basic or fundamental explanatory view in which moire is removed by a double image which uses the single-sided multiple slant-face prism;

FIG. 35 is an explanatory view in which function of removing the generation of moire due to color modulation by a trap line is shown by a spatial frequency planar face;

FIG. 36 is an explanatory view showing an array of an image of a fiber bundle serving as a fiber assembly;

FIG. 39 is an explanatory view showing an aspect in which a boundary of the multiple slant-face prism is formed in eccentricity;

FIG. 40 is an explanatory view showing the fact that the vicinity of a center in the boundary of the multiple slant-face prism is so ground as to come into a planar face;

FIG. 41 is an explanatory view showing the fact that it is preferable that the multiple slant-face prism is arranged in the vicinity of a pupil;

FIG. 42 is an entire or whole arrangement view of an endoscope apparatus according to a tenth embodiment;

FIGS. 47A to FIG. 48 relate to a first modification of the twelfth embodiment, FIG. 47A being an explanatory view showing a direction of a boundary line of a double-sided multiple slant-face prism;

FIG. 48 is an explanatory view showing a dark-part removal operation of a clad part by a spatial frequency planar face, due to the first modification of the twelfth embodiment;

FIG. 49B is an explanatory view showing a dark-part removal operation of a clad part by a spatial frequency planar face;

FIG. 50 to FIG. 51B relates to a thirteenth embodiment, FIG. 49 being a cross-sectional view showing an ocular adaptor for dark-part removal according to the thirteenth embodiment;

FIG. 51B is an explanatory view showing a dark-part removal operation of a clad part corresponding to a state in FIG. 51A, by a spatial frequency planar face;

FIG. 57D is a characteristic view showing MTF characteristics of the single-sided multiple slant-face prism, by a spatial frequency planar face;

FIG. 58A to FIG. 58C are views showing a single-sided multiple slant-face prism in a modification of the seventeenth embodiment;

FIG. 59 is a view showing a single-sided multiple slant-face prism in an eighteenth embodiment;

FIG. 60A and FIG. 60B are respectively showing a front face or elevation and a top plane or planar face of a single-sided multiple slant-face prism in a modification of the eighteenth embodiment;

FIG. 61 is a view showing an optical path length in a double-sided multiple slant-face prism;

FIG. 63A is a front elevational view of a phase filter;

DETAILED DESCRIPTION OF THE PREFERRED EMBODIMENTS

Figure 1:
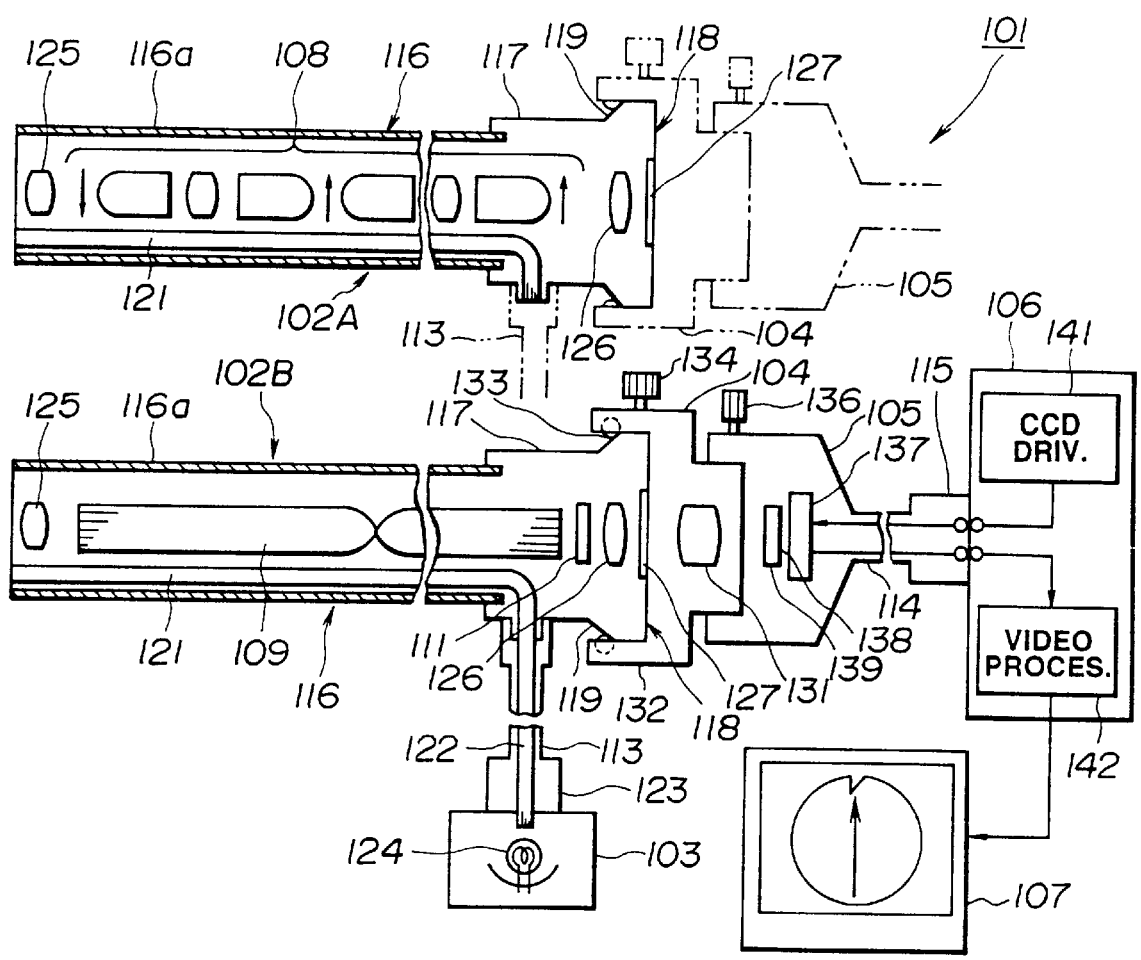
FIG. 1 to FIG. 8 relate to a first embodiment of the invention, FIG. 1 being an arrangement view of an endoscope system according to the first embodiment.

Various embodiments of the invention will hereunder be described in detail with reference to the accompanying drawings.

An endoscope system 101 according to a first embodiment of the invention shown in FIG. 1 comprises a first hard endoscope 102A having a relay lens system 108 serving as image transmission means, a second hard endoscope 102B having an image guide fiber bundle (hereinafter abbreviated as "IG") 109 serving as image transmission means, a light source device 103 for supplying an illumination light to illumination-light transmission means of the first or second hard endoscope 102A or 102B, through a light guide cable 113, a radiographic adaptor 104 detachably mounted on or detachably connected to the first or second hard endoscope 102A or 102B, a TV camera 105 detachably mounted on or detachably connected to the radiographic adaptor 104, and having built therein an image pickup element, a camera control unit (hereinafter abridged as "CCU") 106 to which a connector 115 provided on a camera cable 114 which extends from the TV camera 105 is detachably connected, and which has built therein signal processing means with respect to the image pickup element, and a color monitor 107 connected to the CCU 106, for displaying an endoscope image.

Each of the first and second hard endoscopes 102A and 102B has a hard insertion part 116 formed by an elongated metallic cylindrical pipe 116a, a grip par 117 formed thick in diameter at a rearward end of the insertion part 116 and gripped by an operator, and an ocular part 118 provided with an eyepiece frame 119 formed conically, at a rearward end of the grip part 117.

A light guide 121 for transmitting the illumination light is inserted into the insertion part 116. The light guide 121 has a rearward end thereof which reaches to a base of the grip part 117. A connector which is provided on one end of the light guide cable 113 into which a light guide 122 is inserted can be connected to the base. A connector 123 at the other end thereof can detachably be connected to the light source device 103. The illumination light which is generated by a lamp 124 within the light source device 103 is applied to or is irradiated to an end face of the light guide 122, and is transmitted by the light guide 122. The illumination light is supplied to the light guide 121 having an end face on the side of a rearward end thereof which is fixed to the base.

The illumination light transmitted by the light guide 121 is outputted forwardly from a distal end face thereof which is fixed to an illumination window, on the side of a distal end thereof, of the insertion part 116, to illuminate a forward object such as an affected or diseased part or the like. An observation window is formed adjacent to the illumination window, at the distal end part of the insertion part 116. An objective lens 125 is mounted on the observation window so that an optical image is focused onto an imaging position.

In the first had endoscope 102A, the relay lens system 108 is arranged with the insertion part 116 through a lens receiving tube or the like, along an optical axis of the objective lens 125. The relay lens system is arranged such that a plurality of lenses are arranged in an axial direction of the insertion part 116, and a forward real image is formed invented on the rearward side, whereby the real image due to the objective lens 125 is transmitted to the rearward side in a relay manner. A final image which is transmitted in a relay manner to the rearward position of the final lens of the relay lens system 108 is imaged. The final image can be observed in enlarged form from an ocular window through an ocular lens 126 which is built in the eyepiece part 118. The ocular window is sealed by a cover glass 127. A diaphragm 128 is formed at a pupil position between the ocular lens 126 and the cover glass 127.

Meanwhile, in the second hard endoscope 102B, the IG 109 serving as image transmitting means has a distal end face thereof which is arranged at an imaging position of the objective lens 125. The IG 109 is formed by a plurality of bundled fibers, or the like, so that an image on the distal end face is transmitted to a rearward end face. In FIG. 1, the image is twisted on the way, and an inverted image is inverted so that the inverted image is made to an erecting image at the rearward end face.

Figure 2:
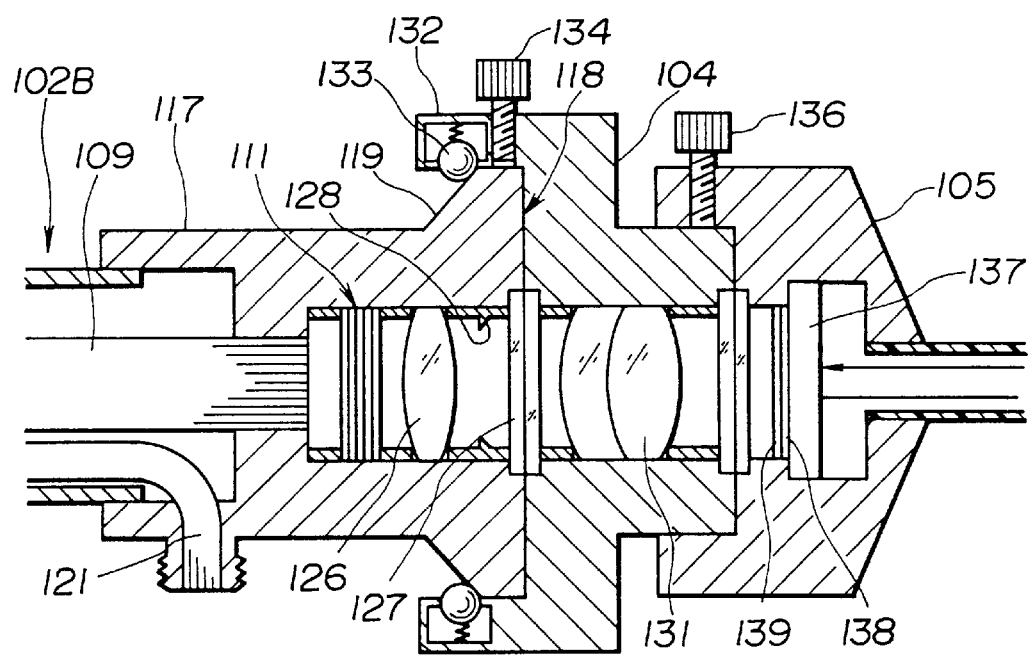

As shown in FIG. 2, an optical low-pass filter (hereinafter abridged as "LPF") 111 for moire removal is arranged in opposed relation to the rearward end face of the IG 109. Further, the ocular lens 126 is arranged in opposed relation to the LPF 111, similar to the first hard endoscope 102A. Thus, it is possible to conduct enlarged observation from the ocular window. Moreover, the ocular window is sealed by the cover glass 127.

Figure 3:
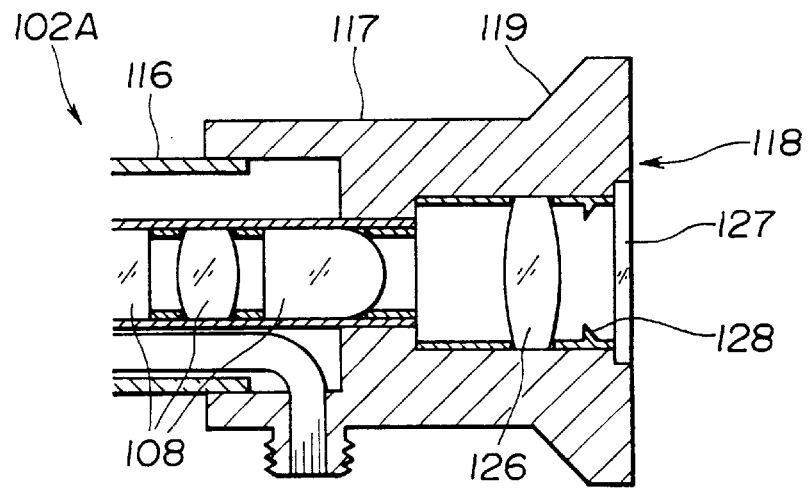

FIG. 3 shows a structure in the vicinity of the ocular part 118 of the first hard endoscope 102A. The arrangement is such that an image due to the relay lens system 108 can be observed in enlargement through the ocular lens 126.

Specifically, the first hard endoscope 102A and the second hard endoscope 102B are different from each other in that the image transmitting means is different from each other, and that the LPF 111 which is not provided on the first hard endoscope 102A is provided in the second hard endoscope 102B, between the IG 109 and the ocular lens 126.

The radiographic adaptor 104 which receives therein a radiographic lens 131 can be detachably mounted on any of the eyepiece frames 119, in opposed relation to the ocular lens 126. Specifically, any of an eyepiece frames 229 are also the same in size and are the same in shape, and the common radiographic adaptor 104 can be detachably mounted. The radiographic adaptor 104 has a mounting frame part 132 in the form of a ring which projects forwardly. The mounting frame part 132 has an inner diameter thereof which is almost the same in value as an outer diameter of the eyepiece frame 119. The eyepiece frame 119 can be fitted, and the eyepiece frame 119 and the radiographic adaptor 104 are relatively rotatable. Furthermore, a ball 133 is biased by a spring toward the inside in a radial direction, in the vicinity of a distal end of the mounting frame 132, and projects as shown in FIG. 2.

Accordingly, it is possible to mount and demount the radiographic adaptor 104 on the eyepiece frame 119, against the biasing of the spring. Further, under a state of being mounted as shown in FIG. 2, the radiographic adaptor 104 is rotatable in the eyepiece frame 119 under a fastened state so as not to come out by the ball 133. Moreover, a knob 134 serving as rotation detent means is provided in projection on the radiographic adaptor 104. It is also possible to rotate the knob 134 to prevent rotation of the radiographic adaptor 104 and the eyepiece frame 119.

The TV camera 105 is further detachable from the radiographic adaptor 104. For example, a fixing knob 136 is provided in projection on the TV camera 105 which is provided, on a forward end thereof, with a recess which is fitted on the projection which projects toward the radiographic adaptor 104. The knob 136 may be rotated whereby the radiographic adaptor 104 and the TV camera 105 are releasably fixed to each other by a screw, so that they may be demounted from each other.

Furthermore, a CCD 137 is arranged with the TV camera 105, in opposed relation to the radiographic lens 131, to photoelectrically convert the image which is imaged through the radiographic lens 131. A mosaic filter 138 is mounted on an image pickup face of the CCD 137, to optically conduct color separation for each pixel (or picture element). Moreover, an LPF 139 for the prevention of a false or sham color is arranged in front of the mosaic filter 138.

The connector 115 at the rearward end of the camera cable 114 which extends from the TV camera 105 is connected to the CCU 106, whereby a CCD drive signal from a CCD drive circuit 141 within the CCU 106 is applied to the CCD 137. A CCD output signal which is photoelectrically converted is inputted to a video process circuit 142 within the CCU 106 so as to be converted to a standard image signal. The image signal is inputted to the monitor 107. Thus, the endoscope image corresponding to the image signal is displayed.

Figure 4:
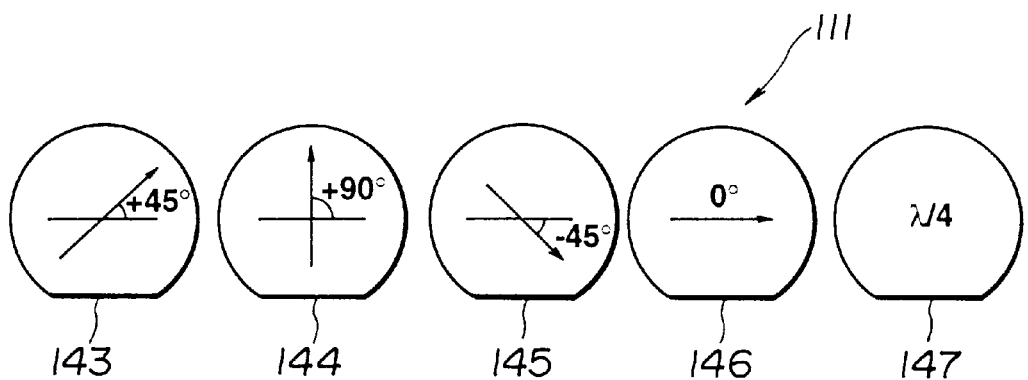

FIG. 4 is a view showing, in decomposition, a quartz plate which forms the LPF 111 which is used in the endoscope system 101 according to the first embodiment. The LPF 111 in the present embodiment is one which is used in the hard endoscope 102B shown in FIG. 1.

Figure 5:
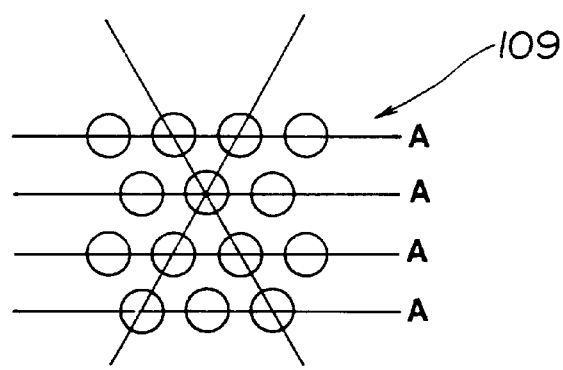

The LPF 111 is arranged as follows. Specifically, it is assumed that, on the basis of a reference of a loading direction A of the fiber which forms the IG 109 shown in FIG. 5, as shown in FIG. 4, a separation direction of the point due to a first quartz plate 143 as counted from the side closer to the IG 109 is +45°, a separation direction of the point due to a second quartz pate 144 is +90°, a separation direction of the point due to a third quartz plate 145 is −45°, and a separation direction of the point due to a fourth quartz plate 146 is +0°. Then, the four quartz plates in which crystallographic axes of the respective quarts plates are shifted from each other every 45°, and a λ/4 plate 147 which is provided on the final face are integrally pasted together.

Figure 6:
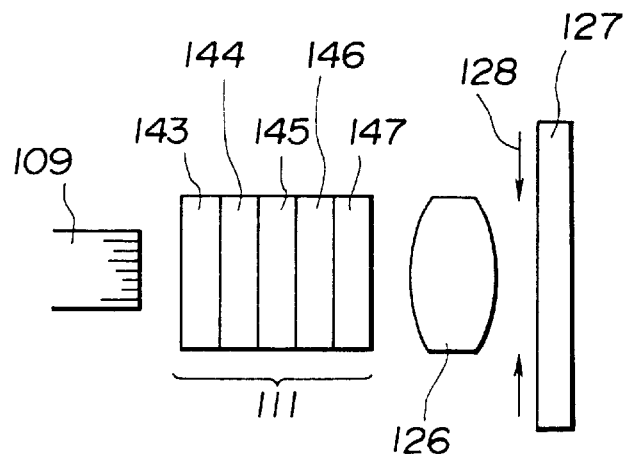

FIG. 6 shows an aspect in which the LPF 111 is inserted into the optical path of the hard endoscope 102B of IG type. In this manner, the LPF 111 which has the quartz plates 143 to 146, and the λ/4 plate 147 is arranged between the IG 109 and the ocular lens 126.

Further, in order to prevent false color, the LPF 139 due to a single quartz plate is provided in the interior on the TV camera 105 which is used in the present embodiment, and is fixed such that the separation direction of the point is in agreement with the scanning direction on the face of the CCD 137 which is built in the TV camera 105. The quartz plate with the TV camera 105 is adapted to be universally rotatable with respect to the LPF 111 within the hard endoscope.

At this time, in the case where the fourth quartz plate 146 which forms the LPF 111 and the crystallographic axis of the quartz plate with the TV camera are in agreement with each other or are made to a wholly reverse state, the separation of the point due to the quartz plate 146 does not occur, or a separation amount thereof is doubled. In order to prevent such deficiency or drawback, the λ/4 plate 147 is provided between the quartz plate 146 and the quartz plate with the TV camera 105, and a linear polarization component which is vibrated in a horizontal or vertical direction with respect to a direction of the crystallographic axis of the quartz plate 146 is converted to circular polarization. Thus, separation of the point due to the quartz plate within the TV camera with respect to an optional rotating direction is made possible. The λ/4 plate 147 is preferable so that G of an intensity signal of the TV camera 105 is selected as the reference wavelength.

In connection with the above, the single λ/4 plate 147 is normally sufficient. However, in the case where wavelength dependency is desired to be improved in accordance with objects, the arrangement may be such that the λ/4 plate 147 is arranged such that a plurality of quartz plates are pasted together so as to have achromatic function.

Figure 7:
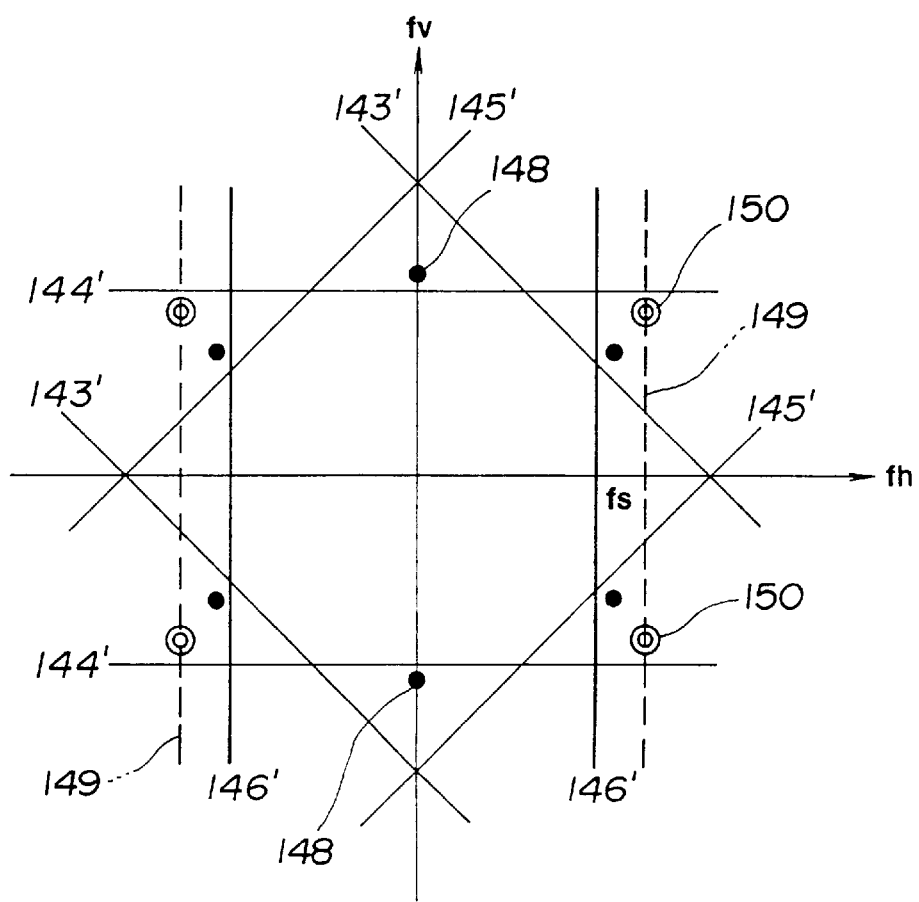

FIG. 7 shows spatial frequency characteristics due to the LPF 111 in the present embodiment. In FIG. 7, fv is the spatial frequency in a vertical scanning direction of the CCD 137 face within the TV camera 105, and fh is the spatial frequency in a horizontal scanning direction of the CCD, while fs is the sampling frequency in a horizontal direction of the CCD 137.

Further, frequencies 148 of the IG 109 on the image pickup face of the CCD 137 under a state that the image which is transmitted from the IG 109 is imaged on the CCD 137 face with image pickup scale factor or magnification β are indicated by ●, while sampling points 150 of the CCD 137 (or the spatial frequency due to two-dimensional array of the photoelectric conversion element in the image pickup face of the CCD 137) are indicated by ⊙. Furthermore, trap lines due to the quartz plates 143~146 are indicated respectively by 143'~146'. Broken lines 149 are trap lines due to the quartz plate which forms the LPF 139 built in the TV camera 105.

As shown in FIG. 7, in order to remove the moire without reducing resolution, the low-pass characteristics of the LPF 111 which is built in the hard endoscope 102B should be such that each of the trap lines is drawn so as to pass lower frequencies which are close to the basic or fundamental spatial frequency due to the array of the IG 109 as far as possible (the thickness of each of the quartz plates should be selected so as to come into so). If the image pickup magnification and variation in distance between textiles of the fibers which form the IG 109 are considered, the range which is lower than the frequency of the IG 109 through a degree of 2~5% is preferable.

Here, if a using state during operation is considered, there are many cases where the hard endoscope 102B and the TV camera 105 are rotated relatively. In the present embodiment, the moire is adapted to be removed without substantial hurting of the resolution, also with respect to the rotation.

Specifically, in the case where it is assumed that the spatial frequencies 148 of the image of the IG 109 on the image pickup face of the CCD 137 are indicated by ●, a spatial frequency region close to or approximate to a circle is secured within ● by the spatial frequency region of an octagon which is encircled by the trap lines 143'~146'. Thus, the present embodiment has a function of removing the moire almost without reducing resolution with respect to the rotation.

The IG 109 and the quartz plates 143~146 are rotated together or in unison with respect to the quartz plates which form the CCD 137 and the LPF 139 within the TV camera 105. In this case, on the fv-fh coordinate in FIG. 7, the trap lines 143'~146' and the frequency 148 of the IG 109 are universally rotated on circumferential loci having the same radius with the origin serving as a center.

As the frequencies 148 are the closest respectively to the sampling points 150 of the CCD 137, greater moire is generated. Accordingly, it is required that, in the neighborhood thereof, the thickness of each of the quart plates 143~146 is set such that two trap lines are piled upon each other slightly less than the frequencies 148.

The frequencies 148 of top and bottom (on the fv axis) in FIG. 7 are spaced from the trap line slightly toward the side of the high frequency. However, the trap lines 143' and 145' are piled up each other double at a location spaced further toward the high frequency. As a result, the frequencies 148 sufficiently cancel the frequency of the IG 109 by three trap lines so as to surround the frequency of the IG 109. In four frequencies 148 other than the same, two trap lines pass substantially just below the same or just above the same. Accordingly, it is possible to sufficiently cancel the frequency of the IG 109.

Figure 8:
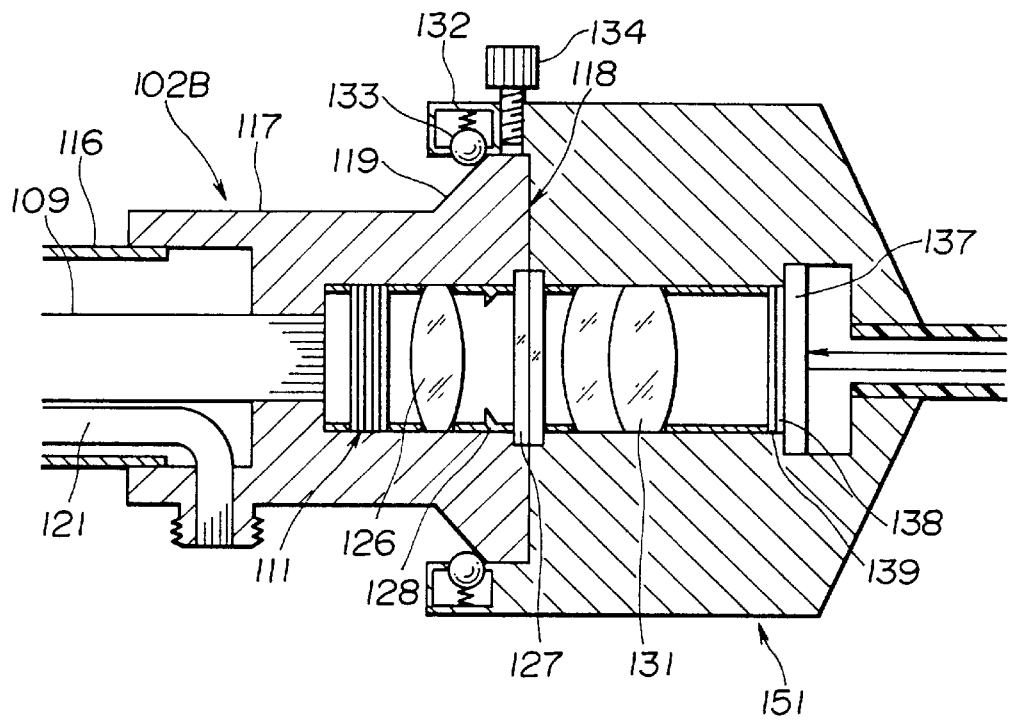

FIG. 8 shows a TV camera device 151 in a first modification of the first embodiment. The TV camera device 151 has a structure in which the radiographic adaptor 104 and the TV camera 105 in FIG. 1 or FIG. 2 are united to each other. The TV camera device 151 has built therein a radiographic optical system, and is rotatably mounted with respect to the hard endoscope 102A or 102B which is mounted by a structure similar to that of the first embodiment.

The other is similar in arrangement to the first embodiment. Function and advantages of the present embodiment are substantially similar to those of the first embodiment.

Figure 9:
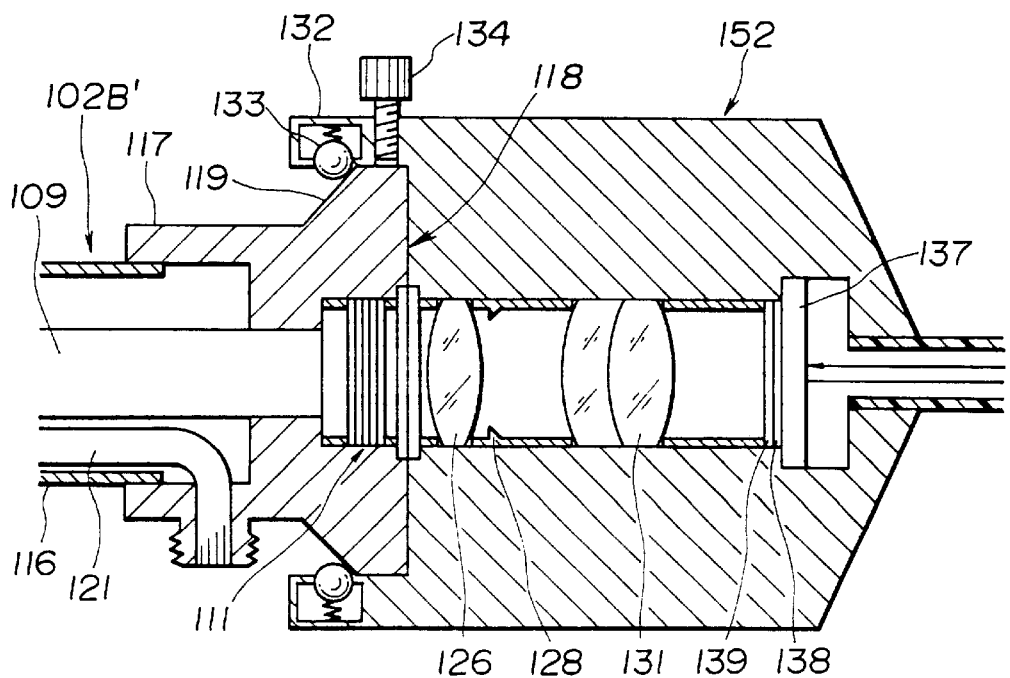
FIG. 9 is a cross-sectional view showing a TV camera device in a second modification of the first embodiment.

FIG. 9 shows a TV camera device 152 in a second modification of the first embodiment. A system of the modification includes the TV camera device 152 having an ocular optical system and a radiographic optical system, and a second hard endoscope 102B' having no ocular optical system. A first hard endoscope 102A' (not shown) also has a structure having no ocular optical system.

Specifically, the TV camera device 152 has a structure in which the TV camera device 151 in FIG. 8 and the ocular optical system of the hard endoscope 102A or 102B are integrated with each other.

In a case where the TV camera device 152 is mounted and is used, the modification can be used similarly to the first modification of the first embodiment.

In a case where the TV camera device 152 is not mounted, but the hard endoscope 102A' or 102B' is used to conduct observation with the naked eye, an ocular adaptor (not shown) which has built therein an ocular optical system can be mounted on the hard endoscope 102A' or 102B' and can be used.

Subsequently, a second embodiment of the invention will be described.

Figure 10:
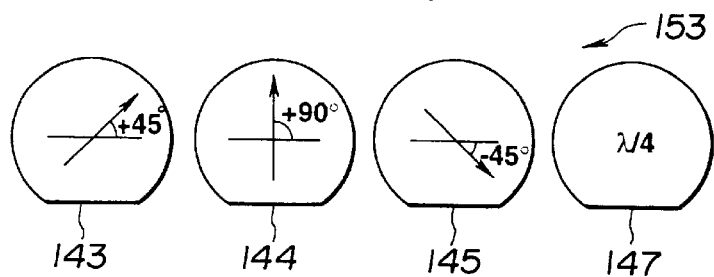
FIG. 10 and FIG. 11 relate to a second embodiment of the invention, FIG. 10 being a view showing a quartz plate which forms an LPF in the second embodiment.

FIG. 10 is a view showing quartz plates which form an LPF 153 used in an endoscope system according to the second embodiment of the invention. In a case where frequency of the IG 109 within the hard endoscope 102B and the cut-off frequency of quartz plates within the TV camera 105 are close to one another, the fourth quartz plate 146 which forms the LPF 111 shown in the first embodiment is omitted and, in place thereof, it can also be used by the quartz plate which forms the LPF 139 built in the TV camera 105.

The arrangement of the LPF 153 in the present embodiment is similar to that shown in the first embodiment except that the quartz plate 146 is omitted from the LPF 111.

Accordingly, a luminous flux which is separated by the three quartz plates 143, 144 and 145 is converted to a circular polarization from a linear polarization through a λ/4 plate 147. Thus, fourth separation of the point occurs depending not upon a rotational position of the quartz plate of the LPF 139 which is built in the TV camera 105. Accordingly, low-pass results due to the three quartz plates 143~145 are used 100%, while the quartz plates of the LPF 139 which is built in the TV camera 105 can also effectively be used.

Figure 11:
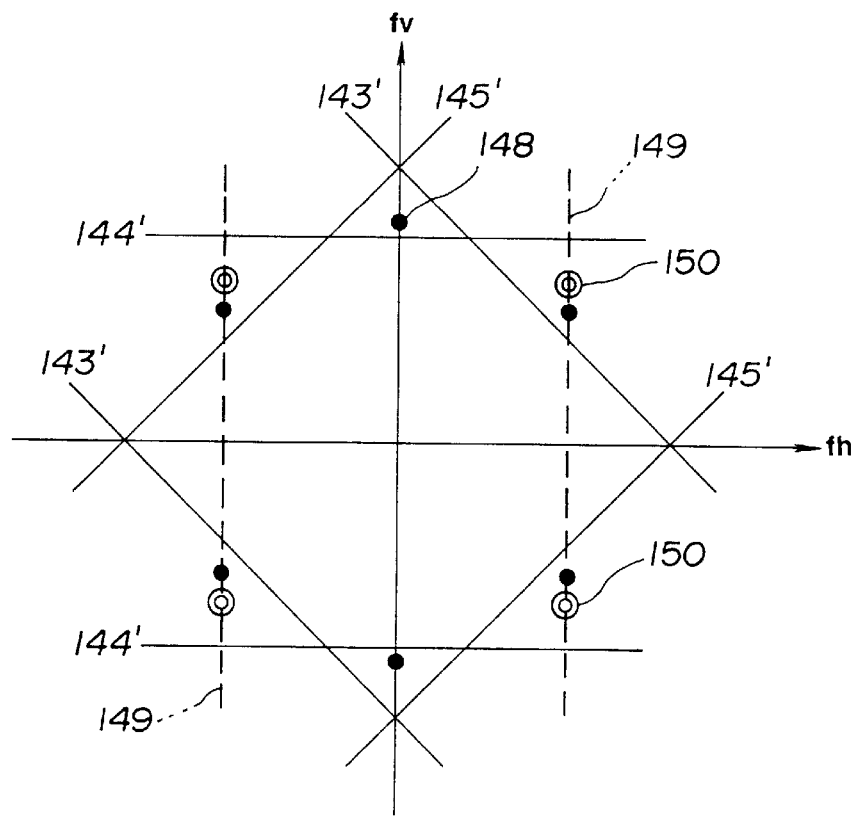

Moreover, since a wide area surrounded by the trap line can be secured, resolution increases as compared with the arrangement shown in the first embodiment. An aspect thereof will be shown in FIG. 11. The reference numerals in FIG. 11 are the same as those in the frequency characteristic view shown in FIG. 6. As shown in FIG. 11, in the present embodiment, the trap line 149 is positioned equivalent to the frequency of the IG 109 or slightly toward the low frequency. Accordingly, the quartz plate 146 can be omitted.

Subsequently, a third embodiment of the invention will be described.

Figure 12:
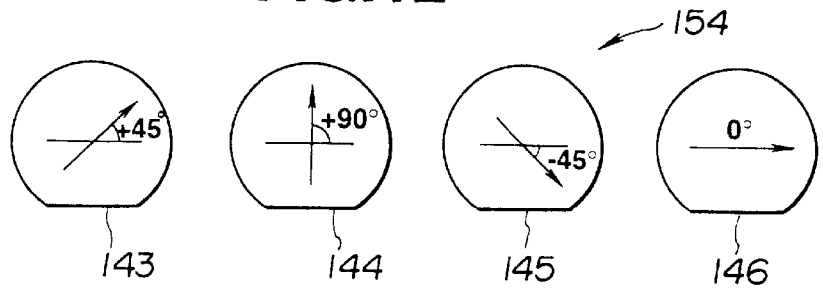
FIG. 12 is a view showing a quartz plate which forms an LPF in a third embodiment of the invention.

FIG. 12 is a view showing quartz plates which form an LPF 154 used in an endoscope system according to the third embodiment of the invention. An arrangement of the LPF 154 in the present embodiment is different from those shown in FIG. 1~FIG. 11 only in that the λ/4 plate 147 is omitted from the LPF 111 shown in the first embodiment. In a case where the quartz plates are available at low cost, less than the λ/4 plate 147, if the LPF 154 is formed as in the present embodiment, a reduction in cost is possible.

Under a state in which the crystallographic axis of the fourth quartz plate 146 of the LPF 154 and the crystallographic axis of the quartz plate which forms the LPF 139 which is built in the TV camera 105 are reversed through 180°, the separation of the point of the quartz plate 146 disappears, and the low-pass effects are limited only to those due to the other three quartz plates. To the contrary, in a case where directions of the crystallographic axes are in agreement with each other, an amount of separation of a point is made twice. Since the aforesaid trap line is moved toward the side of the low frequency, slight reduction of the resolution can be observed. However, there can be produced an image which is practically permissible.

FIG. 13 shows a structure in the vicinity of an ocular part of the second hard endoscope 102B" in the endoscope system 155 according to a fourth embodiment of the invention. In the present embodiment, an LPF 157 which uses a two-slant-face prism 164 or the like shown in FIG. 14A and FIG. 14B is arranged between the ocular lens 126 and the stop 128.

FIG. 14A is a front elevational view of the two-slant-face prism 164 as viewed from an optical-axis direction, while FIG. 14B is a side elevational view of the two-slant-face prism 164 in which FIG. 14A is viewed from a direction of an arrow D.

As shown in FIG. 14A and FIG. 14B, the two-slant-face prism 164 in the present embodiment comes into a slant face in which planar faces divided in half by a boundary line L1 which passes through a center thereof have inclinations different in direction or orientation from each other. The two-slant-face prism 164 utilizes prism function having two slant faces each having the same inclination in opposite directions, to conduct the separation of the point.

Specifically, as shown in FIG. 14B, of a light ray which is incident upon the two-slant-face prism 164, a component which is incident upon one face S1 and a component which is incident upon the other face S2 are refracted in directions opposite one another. Accordingly, a double image which is slightly shifted in the refraction direction (in a vertical direction in an example shown in FIG. 14A and FIG. 14B) is formed on an image face. Thus, the present embodiment has spatial frequency limiting or restriction effects similar to those of the LPF due to the quartz plate 144.

It is possible to vary or change the inclination angles of the faces S1 and S2, whereby an amount of separation of the image is adjusted. Furthermore, four two-slant-face prisms of this kind are piled up each other such that the directions of the boundary line are different from one another every 45°, i.e., such that the separating directions of the image are different from each other like the quartz plates 143~146 in FIG. 4 and, further, the ¼ wavelength plate 147 is piled upon the two-slant-face prism, similarly to FIG. 4, so that the LPF 157 is formed. It is preferable that, as shown in FIG. 13, the LPF 157 is arranged in the vicinity of the pupil position where the stop 128 is arranged.

The other arrangement in the present embodiment is the same as that shown in FIG. 1. For example, the first hard endoscope 102A is the same as that shown in FIG. 1 or FIG. 3.

The present embodiment has the following merits. That is, the two-slant-face prism 164 or the like which can be manufactured considerably lower in cost than the quartz plates is used to realize the system which has a function similar to the first embodiment.

In connection with the above, it is also possible to use the cover glass 127 by the LPF 157 in the present embodiment.

Furthermore, it is also possible that the two-slant-face prism as shown in FIG. 14A and FIG. 14B, is applied to the second embodiment illustrated in FIG. 10 or to the third embodiment illustrated in FIG. 12. In this case, it is possible to extract one from the LPF 157 shown in FIG. 13.

FIG. 15 shows, in decomposition, an LPF 171 which is used in an endoscope system according to a fifth embodiment of the invention. In the present embodiment, the LPF 171 is of structure in which two four-slant-face prisms 172 and 173 and the single ¼ wavelength plate 147 are piled upon one another. A front elevational view of the four-slant-face prism 172 which is used in the present embodiment is shown in FIG. 16.

Figure 16:
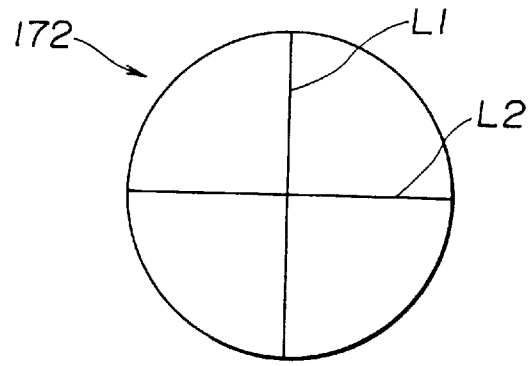
Figure 17:
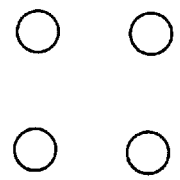

As shown in FIG. 16, the four-slant-face prism 172 has four slant faces which are divided into four by boundary lines L1 and L2 which extend perpendicularly to each other. Accordingly, a separation pattern of a point due to the four-slant-face prism 172 conducts the separation of the point into two in a horizontal direction which extends perpendicularly to the boundary line L1, as shown in FIG. 17, and conducts the separation of the point into two in a longitudinal direction which extends perpendicularly to the boundary lines L2. The other arrangement is similar to that of the first embodiment.

By the LPF 171 shown in FIG. 15, a function similar to that of the first embodiment is realized at low cost. It is also possible to use an LPF in which the ¼ wavelength plate is deleted from the LPF 171, in place of the LPF 154 in FIG. 12.

As shown in FIG. 17, it is preferable that, in accordance with the desired separation pattern of the point, a plurality of slant face parts which are inclined to each other, are provided on a face of the LPF with determined angles. Moreover, if the divided areas in the slant face at the pupil face are equalized to on another, point separation of the equal strength is made possible. In this example, angles of the four slant face parts are so set as to acquire the image separation pattern of substantially square shape.

Figure 18:
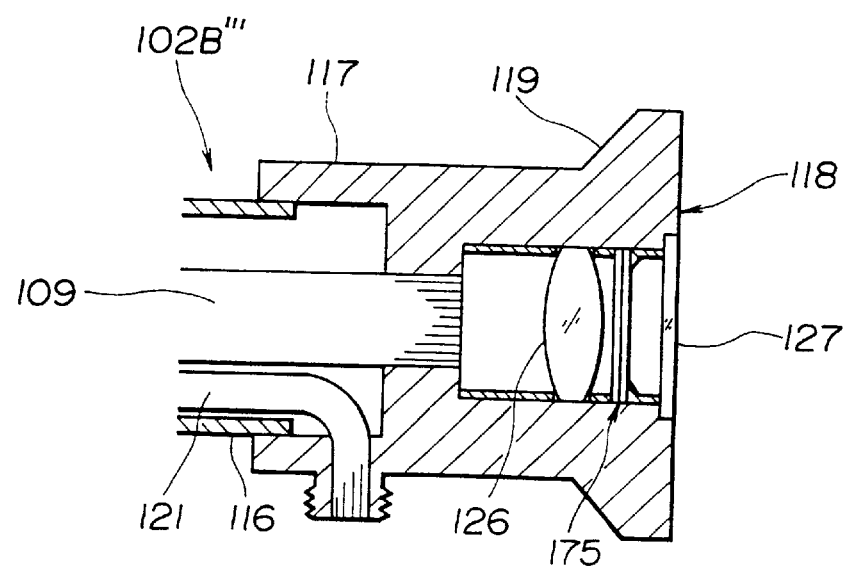
FIG. 18 and FIG. 19 relate to a sixth embodiment of the invention, FIG. 18 being a cross-sectional view showing an arrangement in the vicinity of an ocular part of a second hard endoscope in the sixth embodiment.
Figure 19:
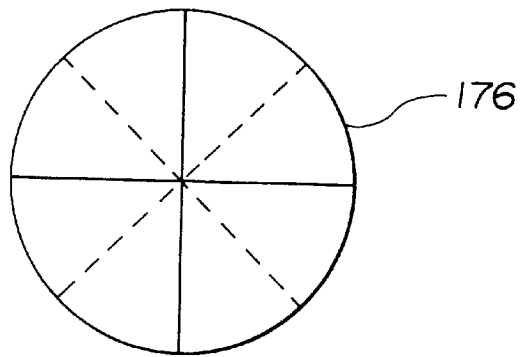

FIG. 18 shows structure in the vicinity of an ocular part of a second hard endoscope 102B''' in a sixth embodiment of the invention. In the sixth embodiment, an LPF 175 comprises the ¼ wavelength plate 147 and a double-face four-slant-face prism 176 shown, in front elevational view, in FIG. 19. As shown in FIG. 15, the LPF 175 is arranged such that the four-slant-face prisms 172 and 173 each of which is formed with four slant faces on a single face are formed respectively on both faces thereof.

Specifically, the LPF 175 is arranged such that the four-slant-face prism 173 is formed on the side of a rear face of the four-slant-face prism 172 in FIG. 15. The LPF 172 is arranged in the vicinity of the stop 128. The other is similar in arrangement to the first embodiment.

The present embodiment can also realize a system which has a function and advantages similar to those of the first embodiment, at low cost.

Figure 20:
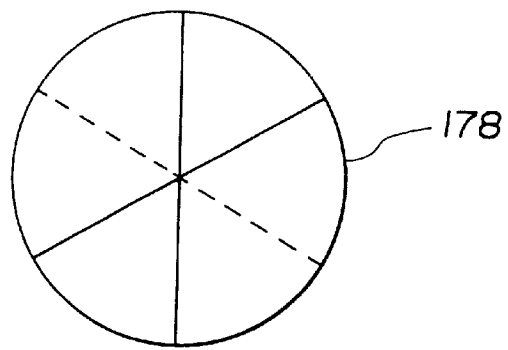
FIG. 20 is a front elevational view showing a double-sided slant-face prism in a seventh embodiment of the invention.

FIG. 20 is a front elevational view of a double-face slant-face prism 178 which forms an LPF used in an endoscope system according to a seventh embodiment of the invention. This embodiment also utilizes prism effects similarly to the fourth~sixth embodiments. Solid lines in FIG. 20 indicate boundary lines of the slant face which is provided on a face, while a broken line indicates a boundary line of the slant face which is provided on a rear face.

In the face, each of the slant faces is so provided that an area ratio between a large face and a small face comes into 2:1, while, in the rear face, two slant faces are so provided that the boundary line is located at a position which divides in half the area portion in which the face is large.

By a refraction action of these slant faces, an incident light is separated into six points which form a substantially hexagonal shape, and which are equal in strength. In this manner, if the slant faces are provided respectively in a front and a rear, it is possible to form a plurality of separated images, by filters which are fewer in number. Accordingly, if the LPF in the present embodiment is used, space is saved, and an attempt can be made to miniaturize the hard endoscope body.

Of course, the LPF of the present embodiment is also arranged at the position similar to the LPF shown in the fourth embodiment.

An eight embodiment of the invention will subsequently be described.

As shown in the seventh embodiment, in the case where the filter provided with the straight line part on the face of the glass is used, when the accuracy of the angles of the slant-face portions which are delimited by such straight lines is deteriorated or low, the aforesaid straight line part is seen, and a ghost-image is generated. Thus, there is the case where a state which is difficult to conduct the observation is offered.

Figure 21:
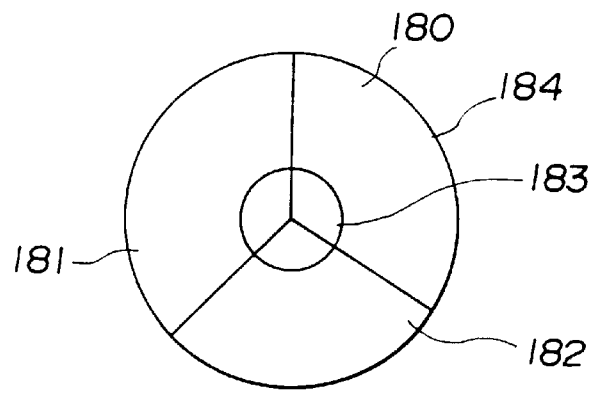
FIG. 21 and FIG. 22 relate to an eighth embodiment of the invention, FIG. 21 being an explanatory view showing the fact that a pupil diameter upon eye-viewing observation and a pupil diameter upon TV observation are compared in magnitude with each other.

As shown in FIG. 21, when time upon the naked-eye observation and time upon observation due to the TV camera are compared with each other, the magnitudes of the pupil diameter are different from each other, and there are many cases where the magnitudes of the pupil diameter upon the naked-eye observation are smaller than the latter. When an area of the straight part which is occupied in the pupil diameter increases, such straight part becomes conspicuous.

In FIG. 21, the reference numerals 180~182 denote slant-face parts, the reference numeral 183 denotes a pupil diameter of eye, and the reference numeral 184 denotes a pupil diameter upon an image pickup by the TV camera. In this manner, in the case where it is difficult to improve the accuracy of the slant-face angle, it is considered that the straight part is not provided on a conspicuous portion of the pupil diameter (the pupil diameter of eye 183 in FIG. 21), but a slant face is provided out of the pupil diameter, to acquire low-pass effects.

Further, in the case where a pupil of the eye is smaller than the TV camera, the straight part should be deleted regarding the portion equivalent to the pupil of the eye.

Figure 22:
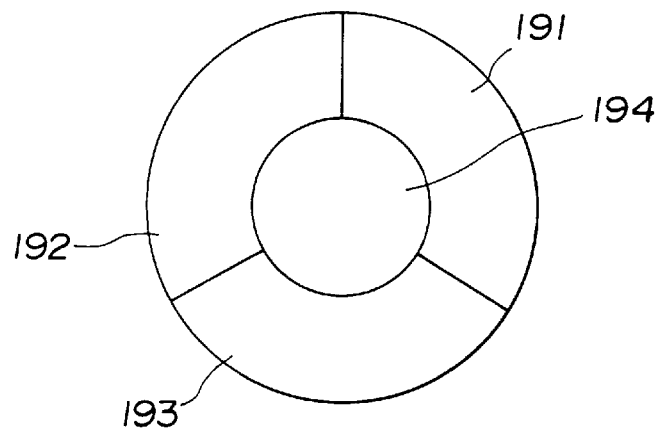

In view of the above, an LPF of the present embodiment is shown in FIG. 22. As shown in FIG. 22, in the LPF, a planar face 194 which is vertical to an optical axis is provided on a portion which corresponds to the pupil diameter upon the naked-eye observation. Moreover, slant faces 191 to 193 are provided on an outer periphery of the planar face 194.

Figure 23:
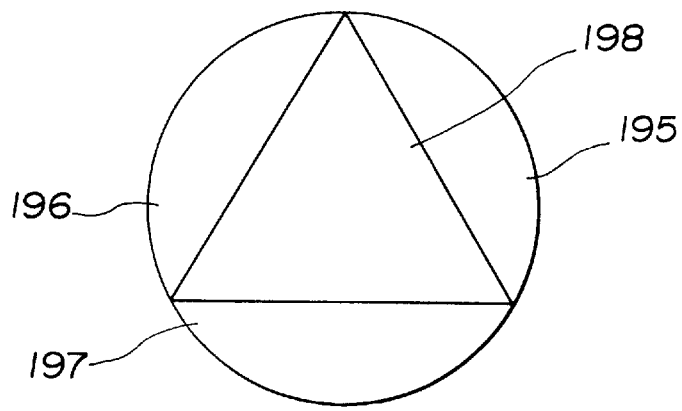
FIGS. 23 to 27 relate to a ninth embodiment of the invention, FIG. 23 being a front elevational view showing a quartz plate which forms an LPF in the eighth embodiment.

FIG. 23 shows an LPF which is used in the endoscope system according to a ninth embodiment of the invention.

The LPF in the present embodiment in an another enforcement mode of the LPF shown in the eight embodiment. Planar face 195 corresponds to the planar face 194 in FIG. 21, while slant faces 195~197 correspond to the slant faces 191~193.

Furthermore, a method will be described in which, by a system in which another means is used on the side of the body part, that is, by the fact that a distance between textiles of fibers which form an IG for conducting an image pickup on a CCD face with the TV camera is sufficiently reduced, generation of moire is. Here, the case where a pigment array of the IG is hexagonal minuteness or closeness is shown as an example.

Figure 24:
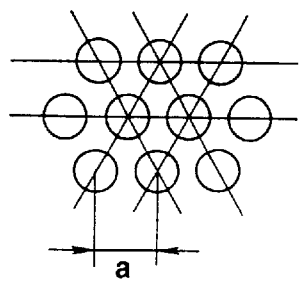

As shown in FIG. 24, the frequency fp of the fiber which forms the IG in this case is indicated by the following expression:

$$fp = \{(\sqrt{3/2})an\} - 1 \tag{1}$$

where a is a distance between textiles of the fibers, and n is an optional number. Further, when the case of n=1 is assumed to be fundamental frequency, there exists a frequency component of 1/n times thereof.

Moreover, regarding the CCD within the TV camera, if fn is the Nyquist frequency, and fs is the sampling frequency, both of them are determined by the structure of the CCD, and are indicated by the following expression:

$$fn=1/mpi \tag{2}$$

$$fs=1/pi \tag{3}$$

where pi is a pixel size on the CCD face in a horizontal scanning direction or a vertical scanning direction, and m is the optional constant. This is decided by an array of a color filter in the case of a mosaic filter or the like.

Figure 25:
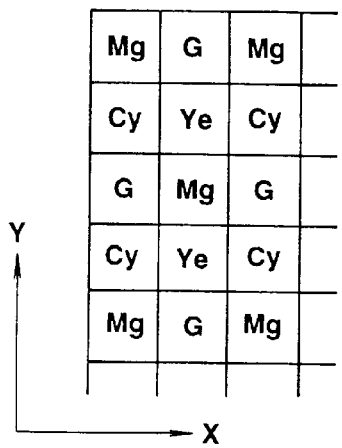

For example, in the case of an array as shown in FIG. 25, the Nyquist frequency fn in a y-(vertical) direction of G is as follows:

$$fn=1/2py$$

where py is a pixel size in a direction horizontal to the scanning line of the CCD.

Selection of the distance between the textiles of the fibers which form the IG for preventing the moire from occurring will subsequently be described. In order to prevent the moire from occurring, it is preferable that the fundamental frequency fp of the fibers on the CCD face is higher than the cut-off frequency on an MTF (the absolute value of response function) of the image pickup optical system. Since, however, as indicated in the expression (1), there exist secondary and third frequencies, only this is not sufficient. Practically, it is sufficient if suppression can be made up to the third frequency. Particularly, if the secondary frequency fp/2 comes up in the vicinity of fs, the secondary frequency fp/2 is folded back so that the moire of the low frequency is generated, causing remarkable reduction of the image. In order to avoid this phenomenon, it is required that a value of fp/2 is substantially equalized to fn. Specifically, a conditional expression indicated below must be satisfied:

$$0.8 \leq fp/2 \cdot fn \leq 1.2 \tag{5}$$

Further, although the frequency of the fibers is universally rotated on a CCD frequency space, the moire is likely to be conspicuous when accessed to the sampling point. Accordingly, a method to deal with this should be considered. As described above, since the third frequency is equal to or below the Nyquist frequency, this frequency does not participate in generation of the moire.

The fundamental frequency will subsequently be considered.

Figure 26:
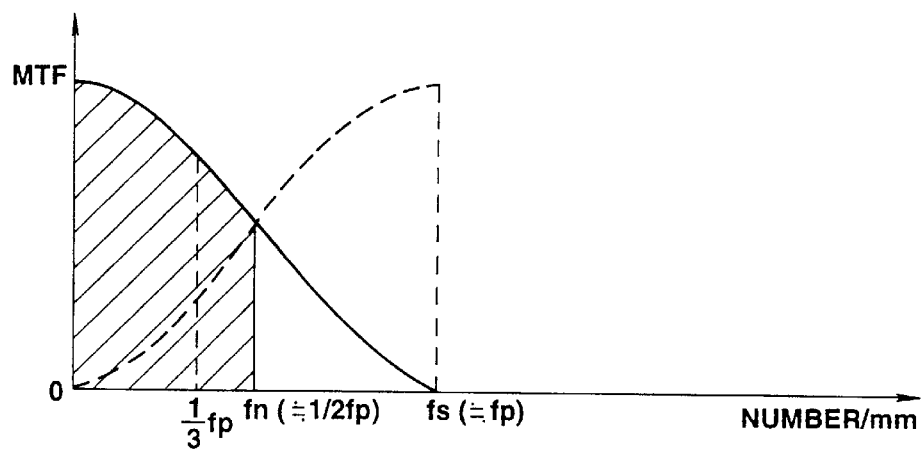
Figure 27:
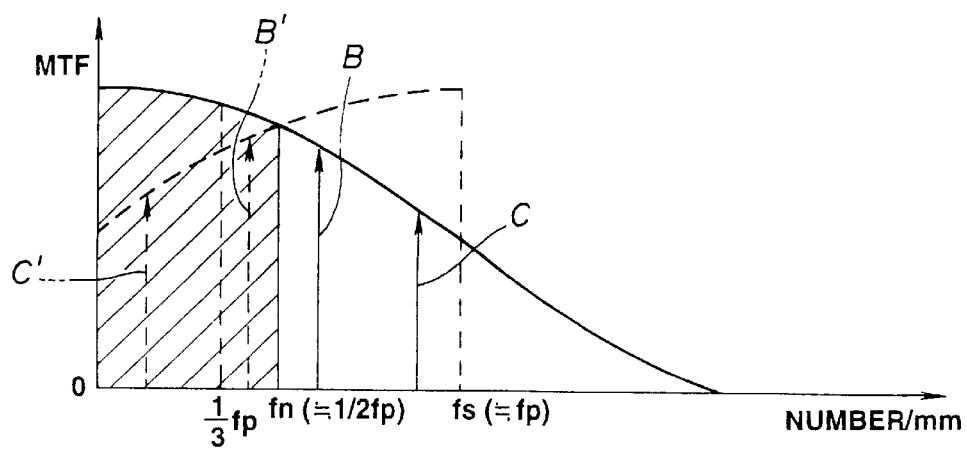

FIG. 26 and FIG. 27 are views for the description of the MTF characteristics in the scanning direction of the CCD. In these figures, solid lines indicate an MTF of an image pickup optical system which does not include the LPF. In the case of the arrangement illustrated in FIG. 1, an optical system in which the ocular lens and the imaging lens within the adaptor are synthesized with each other. Furthermore, broken lines indicate a loop or folded component, which occurs due to the sampling of the CCD. In this case, the fundamental frequency fp is equalized to the cut-off frequency of the MTF of the image pickup optical system. Substantially twice the value of fn comes into a value equal to the value of fs in the example. In such a case, the moire due to the primary~third fiber frequencies is not generated. In this manner, the following two methods will be considered in order that the MTF of the image pickup optical system is equalized to the fundamental frequency fp.

The first method is a method of restricting the image pickup optical system to conduct setting such that the diffraction limit comes into the vicinity of the value of fp. Diffraction limiting frequency fl on the CCD face due to the image pickup optical system is decided by an expression indicated below:

$$fl=(0.61\lambda/N.A.)-1 \tag{7}$$

where λ is wavelength of flux of light or luminous flux which is transmitted from the image pickup optical system, and N.A. is a numerical aperture of the image pickup optical system.

A second method is to design that an MTF cut-off frequency of the image pickup optical system is set as to beforehand come low. For example, the second method is that spherical aberration or eccentric or decentering aberration is intentionally generated high in the image pickup optical system.

FIG. 27 is a view showing the MFT characteristics in the scanning direction on the CCD face, for the description of a state in which the MFT of the image pickup optical system is sufficiently remained in fs. As will be seen from FIG. 27, since the cut-off frequency in the optical system is a frequency sufficiently higher than the Nyquist frequency fn of the CCD, a value of the MTF in the Nyquist frequency is large, but the folded component thereof is also correspondingly high.

For this reason, if there is a frequency component of an object image between the frequencies fn and fs, a pseudo- or quasi-signal is mixed in a frequency band of the image which is folded toward the opposite side serving as a center of fn and which is fetched. Thus, the pseudo-signal comes into the moire or the like and appears in the image. For example, a component B which is located adjacent to fn is folded and comes to B'. Since, however, among the fetched images, the component B is located toward the high frequency, the stripes of moire are fine and are not conspicuous. To the contrary, a component C adjacent to fs is folded back and comes to a location C' in the vicinity of the origin.

Specifically, the moire is not conspicuous in the frequency component of fp/2 which is located adjacent to fn. However, the moire due to the frequency component of fp which is located adjacent to fs is extremely conspicuous. In order to eliminate or remove the moire, the spatial frequency response in the frequency fs must be reduced. However, in the case where the MTF of the image pickup optical system cannot be sufficiently or reduced in fs by the aforementioned method, it is required that the aforesaid LPF is used to sufficiently reduce the response of fs.

Design data on the basis of the aforesaid first method will be indicated below:

In case of px=10$\mu$, and py=10
fs=100 (lp/mm), fn=50 (lp/mm)
a=5.8$\mu$, $\beta$=2
whereby
fp=1/(3·a/2)/$\beta$=100 (lp/mm)
Accordingly,
fp/2=50 (lp/mm), fp/3=33.3 (lp/mm)
When the F number=15.6, by N.A.=0.032
fl=100 (lp/mm)$\neq$fp Thus, there can be provided the MTF characteristics similar to those shown in FIG. 26. The moire can be removed without the use of the LPF.

A tenth embodiment of the invention will subsequently be described. An object of each of the tenth embodiment and the latter is to provide an optical device or an image pickup device in which, since the arrangement which uses quartz plates as a filter for removing the moire or the like is costly, the optical device or the image pickup device has a similar function and uses an optical element which can realize the same at low cost.

For this reason, in embodiments and modifications to be described later, a double-face or single-side slant-face prism having at least a plurality of pairs of slant faces which are in a torsional relationship, mainly on double faces or a single face, is used to form an optical device such as an endoscope or the like.

FIG. 28A~FIG. 28D show a double-face multiple slant-face prism 1 which is used in a tenth embodiment of the invention and which serves as an optical element having function of an optical low-pass filter. The double-face multiple slant-face prism 1 is arranged such that multiple slant-face prisms each having two divided faces which are twisted like a propeller are formed respectively on faces on both sides, similarly to one face of a single-face multiple slant-face prism 2 in a modification of the tenth embodiment, shown in FIG. 29A~29C. Accordingly, the single-side multiple slant-face prism 2 which is simple in construction or arrangement and which is used in the modification will first be described.

The single-side multiple slant-face prism 2, in a modification of the tenth embodiment, which has a function of an optical low-pass filter and which serves as an optical element is one which has optical filter function even under a defocus state, among arrangements which are disclosed in Japanese Patent Unexamined Publication No. HEI 3-248695 (248695/1991) and which are point-symmetric around an optical axis.

One side (B side, for example) of the single-side multiple slant-face prism 2 is provided with semicircular a part and b part which are formed such that they jointly own an optical axis O and in which two slant faces are inclined in opposite directions to each other. Normals to these two slant face are in twisting or torsional relationship, and are inclined only through $\theta$ to each other.

By the fact that they are so formed as to be in the torsional relationship, the arrangement is such that, even under the defocus state in which the point is shifted into many directions to be described subsequently, it is possible to leave function of the filter which removes the moire or the like (refer to FIG. 34A).

If the inclinations with respect to the optical axis O of the respective normals of the faces are $\theta 1$ and $\theta 2$, the following expression can be acquired:

$$\theta = \theta 1 - \theta 2 \tag{8}$$

Figure 30:
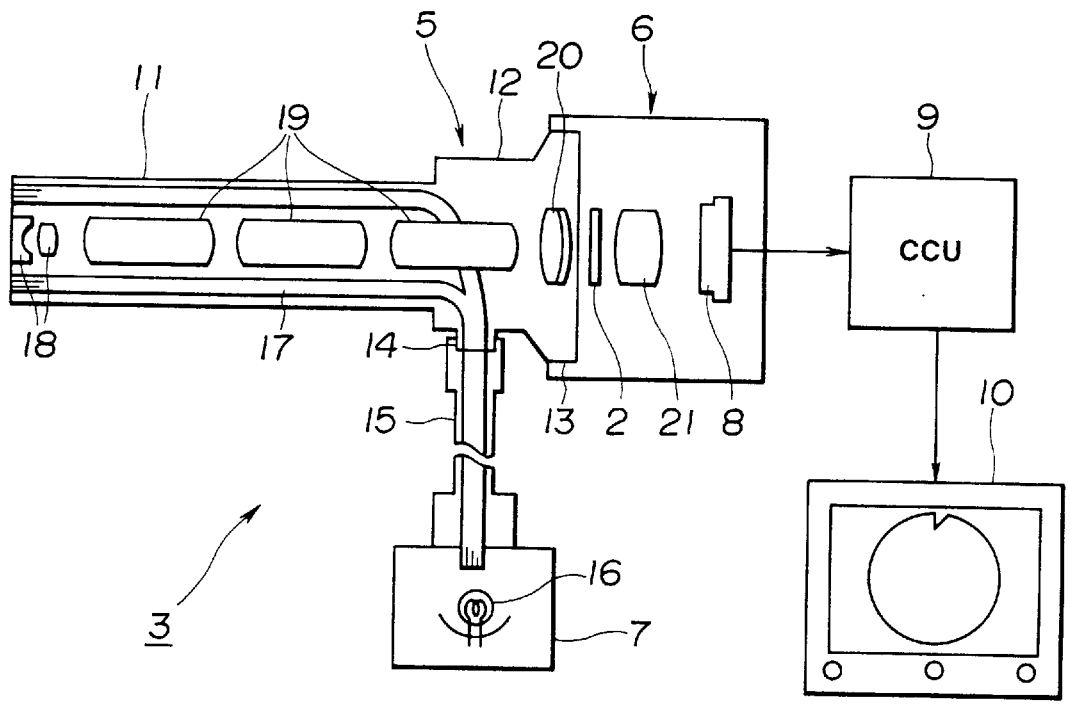

(In this connection, $\theta 1$ and $\theta 2$ express the inclinations including also the codes or marks, and an arrangement illustrated in FIG. 30 indicates $\theta 1 = -|\theta 2|$.)

Shape data of the B side of the single-side multiple slant-face prism 2 are as follows. In the case where a direction of the optical axis O is set to a Z-axis, an X-axis and a Y-axis are set in a plane which is vertical to the Z-axis, and a direction of a boundary line 1 between the a-part and the b-part is set to the X-axis, for example.

If the a-part is a zero (0) or positive range of Y (that is, Y$\geq$0), a face or plane of the a-part is Z=P·X.

If the b-part is a negative range of Y (that is, Y<0), a face or plane of the b-part is Z=−P·X. Here, a parameter P which expresses the inclined face is, for example, as follows:

P=tan 1'$\approx$0.00029 where 1'$\approx$0.00029 rad

In this case, the above-described $\theta$ is $\theta$=2'. Moreover, a size of the single-side multiple slant-face prism 2 is such that, as shown in FIG. 29B and FIG. 29C, a diameter is $\phi$8, a thickness To is To=1 mm, for example, and a refractive index n is n=1.51633, for example.

Figure 29A:
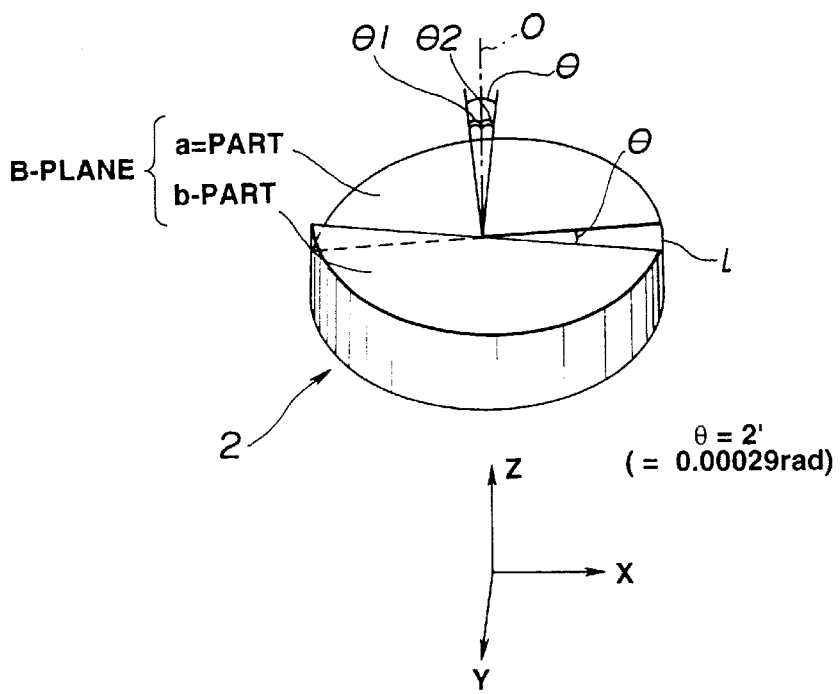
FIG. 29A is a perspective view showing a single-sided multiple slant-face prism which is used in a modification of the tenth embodiment.
Figure 29B:
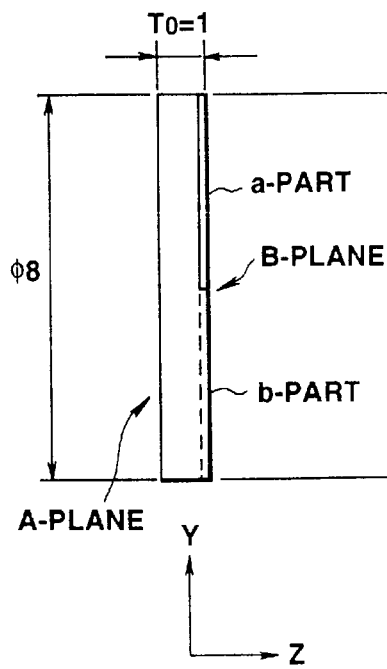
FIG. 29B and FIG. 29C are views respectively showing a side face or elevation and a front face or elevation of the single-sided multiple slant-face prism.
Figure 29C:
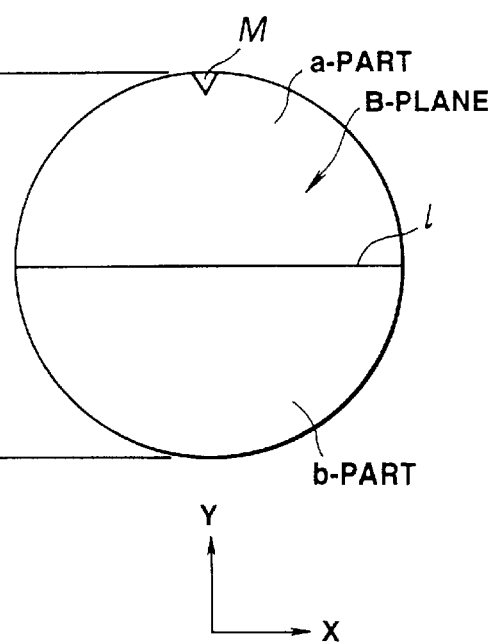

In connection with the above, FIG. 29B is a side elevational view, while FIG. 29C is a front elevational view. Further, as shown in FIG. 29C, a mark M for judging orientation of the optical element is applied to the B side. Moreover, the other side of the single-side multiple slant-face prism 2, that is, an A side is a planar face.

An endoscope apparatus 3 which serves as an optical device according to a modification of the first embodiment which uses the single-side multiple slant-face prism 2 is shown in FIG. 30. The endoscope apparatus 3 comprises a hard endoscope 5 provided with an illumination optical system and an observation optical system, a television camera 6 which has built therein image-pickup means which is mounted on the hard endoscope 5, a light source device 7 for supplying an illumination light to the hard endoscope 5, a CCU 9 for conducting signal processing with respect to a solid-state image pickup element 8 such as a CCD or the like which is built in the television camera 6, and a color monitor 10 connected to the CCU 9, for displaying an image signal which is outputted from the CCU 9.

The endoscope apparatus 3 is one which, resulting from an array of a light receiving element (including also the case of a mosaic filter) which is arrayed two-dimensionally in the solid-state image pickup element 8 serving as an optical element, removes moire which is generated by interference with the array period or cycle, moire due to interference with color modulation, or the like.

The hard endoscope 5 has an insertion part 11 formed by a hard overcoat or mantle tube, a gripped grip part 12 formed at a rearward end of the insertion part 11 and large in diameter, and an ocular part 13 formed at a rearward end of the grip part 12.

The grip part 13 is provided with a light guide base 14 which is detachably connected to the light guide device 7 through the light guide cable 15.

A white illumination light of a lamp 16 within the light source device 7 is transmitted by a light guide which serves as illumination-light transmission means within the light guide cable 15. The illumination light is supplied from the light guide base 14 portion to the side of a light guide 17 within the hard endoscope 5. An illumination optical system is formed which outputs forwardly the illumination light which is transmitted from a distal end face, which is mounted on an illumination window, at a distal end part of the insertion part 11.

At the distal end part, object lenses 18 are mounted on an observation window which is formed adjacent to the illumination window, so that an image of an object which is illuminated by the object lenses 18 is focused thereat. The image is relayed by a relay lens system 19 which serves as an image transmission optical system which is arranged within the insertion part 11 along an optical axis thereof so as to be in coincidence with the optical axis of the object lenses 18, and is transmitted such that an image is focused on the rearward side. Thus, a final image is formed adjacent to the ocular part 13.

An observation optical system is formed such that the image can be observed by the naked eye through an ocular lens (an ocular optical system) 20. In the case where the television camera 6 is mounted on the ocular part 13, the image which is transmitted by the relay lens system 19 is imaged on the solid-state image pickup element 8 having a color separation filter such as a mosaic filter or the like, through the ocular lens 20, the single-side multiple slant-face prism 2 having function of an optical low-pass filter arranged within the television camera 6, and an imaging lens (an image pickup lens) 21. Thus, image picking-up can be conducted.

It is desirable that the single-side multiple slant-face prism 2 is arranged in the vicinity of the position of the pupil of the imaging lens 21.

In connection with the above, a focal length of the imaging lens 21 is a degree of 15~35 MM. However, in the case where the imaging lens 21 is combined with the television camera 6 which uses the CCD of ⅓~¼ inches, it is appropriate that the focal length is a degree of 15~25 mm.

An image pickup signal which is photoelectrically converted by the solid-state image pickup element 8 is converted to a standard image signal by the CCU 9. The image pickup signal is inputted to the color monitor 10 which serves as image display means. Thus, an image corresponding to the image signal is displayed. The solid-state image pickup element 8 has a structure that pixels (picture elements) serving as light receiving elements which have photoelectric conversion function are regularly arranged in the form of a two-dimensional matrix on the photoelectric conversion face, as shown, for example, in FIG. 31.

Figure 31:
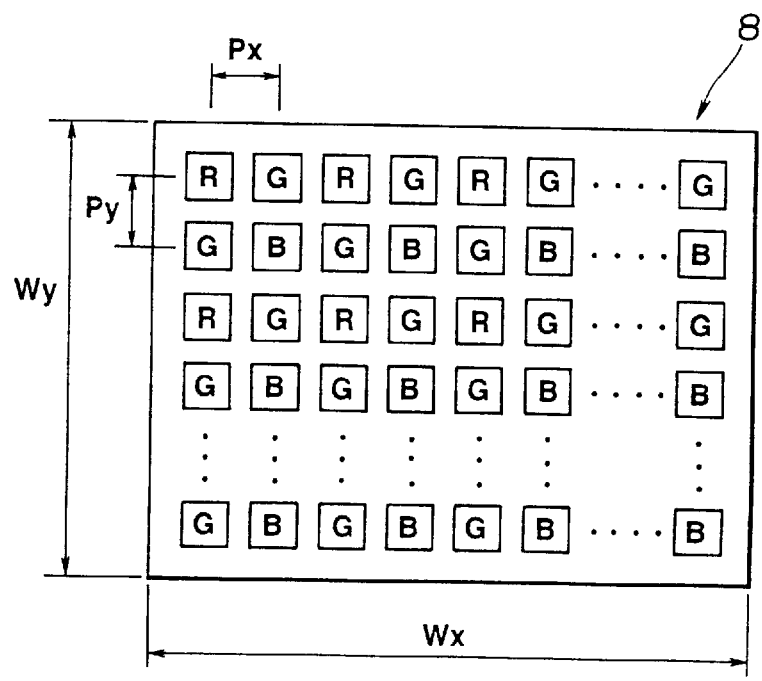

In FIG. 31, the arrangement indicated by R, G and B is that mosaic filters of R (red), G (green) and B (blue) are arranged in front of the pixel. Color image pickup is conducted by the fact that the light which is color-separated into R, G and B is photoelectrically converted. Here, Px . . . dimension of a single pixel of the solid-state image pickup element 8 in a horizontal direction;

Py . . . dimension of a single pixel of the solid-state image pickup element 8 in a vertical direction;

Wy . . . dimension of an effective image pickup area of the solid-state image pickup element 8 in the vertical direction;

Wx . . . dimension of an effective image pickup area of the solid-state image pickup element 8 in the horizontal direction;

M . . . horizontal cycle of the mosaic filter of the solid-state image pickup element 8, which is expressed by a pixel unit. In the example in FIG. 5, M=2, and N . . . vertical cycle of the mosaic filter of the solid-state image pickup element 8, which is expressed by a pixel unit. In the example in FIG. 31, N=2.

In connected with the above, the solid-state image pickup element 8 having no mosaic filter is treated as being M=N=1.

FIG. 32A shows an arrangement direction of the single-side multiple slant-fact prism 2 which is arranged in the vicinity of the stop 10 at the pupil position, and shows that the boundary line (divided line) 1 between the a-part and the b-part is arranged horizontally, that is, in parallel to the horizontal direction (transverse direction) of the solid-state image pickup element 8. In this case, the image is separated in the horizontal scanning direction of the solid-state image pickup element 8.

Specifically, as shown in FIG. 32B, the point passes through the single-side multiple slant-face prism 2, whereby the point comes into a double image in which two points which are spaced a distance d in the horizontal direction away from each other are formed. Description will be made further. As shown in FIG. 32A, a light (a stain pattern) which passes through an upper side of the boundary line 1 which divides the pupil substantially into two images on one in the horizontal direction (an image of a point for simplification), while a light which passes through a lower side of the boundary line 1 images on the other in the horizontal direction.

In this manner, the single-side multiple slant-face prism 2 divides a luminous flux which passes through the pupil, substantially by the boundary line 1, while the light or the luminous flux which passes through each of the slant faces is formed into the double image by the optical system.

As will be described with reference to FIG. 33, the single-side multiple slant-face prism 2 has a low-pass filter function which removes a specific spatial frequency component by the double image.

As described above, the single-side multiple slant-face prism 2 has the low-pass filter function which removes the specific spatial frequency component by the luminous flux which divides the pupil. Accordingly, the single-side multiple slant-face prism 2 can be called "pupil dividing-type LPF". Of course, the double-side multiple slant-face prism 1 can also be called "pupil dividing-type LPF".

Meanwhile, a phase filter 205 which is used in an embodiment to be described subsequently (refer to FIG. 62, for example) is formed such that films 208 which give a phase difference of ½ wavelength to a transparent parallel plate is arranged two-dimensionally. The two-dimensional arrangement is remarkably or considerably small as compared with the size of the pupil. Accordingly, the two-dimensional arrangement is not influenced upon the size of the pupil, and has low-pass filter function which removes the specific spatial frequency component equivalently with respect to the luminous flux which passes through an optional position within the pupil. For this reason, the phase filter 205 and a diffraction grating filter 206 (refer to FIG. 64) which utilize diffraction, a quartz plate (refer to FIG. 65) which utilizes birefrigerance or double refraction, or the like, can be called "non-pupil dividing-type LPF".

In the following description, it is assumed that a horizontal direction (transverse direction) of the solid-state image pickup element 8 is set to an X-axis, while a vertical direction (longitudinal direction) thereof is set to a Y-axis.

FIG. 33 shows an explanatory view of function in which the single-side multiple slant-face prism 2 is used in the image pickup optical system to form the double image to thereby erase a stripe pattern. Basic or fundamental thinking is arranged as follows: Specifically, the moire is generated in case where, when an object image is sampled, sampling frequency and a frequency component which is included in the object image are close to one other. Accordingly, the optical low-pass filter is set to have frequency characteristics so as to remove the frequency component.

As shown in FIG. 33, a bright and dark object is imaged (on the image pickup face of the solid-state image pickup element 8) at the repeating cycle or period by the single-slant multiple slant-face prism 2 and the imaging lens 21, a first image which passes through the a-part and which is imaged, and a second image which passes through the b-part and which is imaged are formed. It is assumed that a separation distance between the first image and the second image is set to ½ of the period. Then, when intensity distributions of the two images are overlapped with each other or are piled on one another, one crest fills up the other trough. Accordingly, the intensity becomes more uniform, and presence of the stripe patterns reduces.

Specifically, when the double image is formed, a frequency component having the repetitive period twice the separation distance of the image is eliminated. Accordingly, if the relationship between the spacing (repetitive period) of the picture element (pixel) for the sampling and the image separation distance is set adequately, it is possible to remove the moire.

Figure 34A:
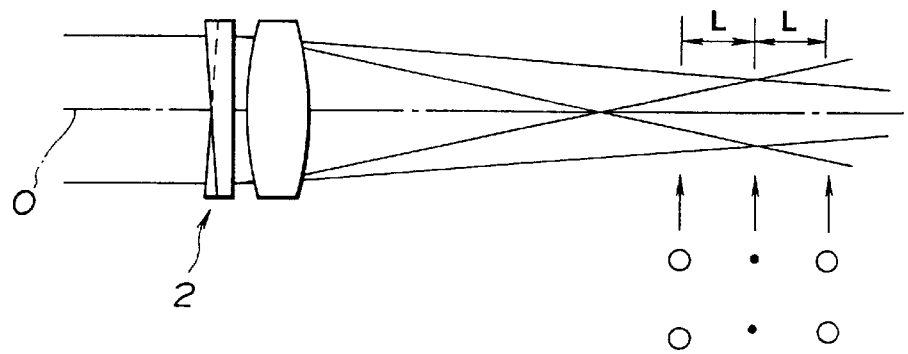
FIG. 34A is an explanatory view showing that a system has moire removal function even under a defocus state.
Figure 34B:
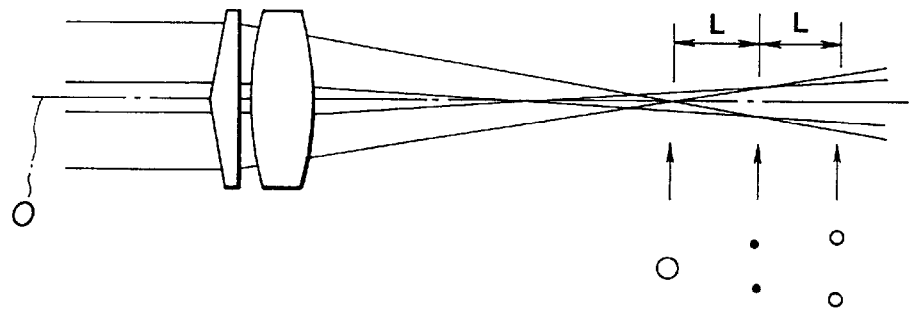
FIG. 34B is an explanatory view of function due to the prior art.

FIG. 34A and FIG. 34B describe a difference in function between an arrangement (FIG. 34A) which satisfies the torsional relationship which is used in the present embodiment or the like, and an arrangement (FIG. 34B) which does not satisfy the same, but is merely symmetrical in point. FIG. 34A shows the optical element in FIG. 29A~FIG. 29C, that is, an optical system portion in which the single-side multiple slant-face prism 2 in which the arrangement of the inclined face satisfies the torsional relationship. FIG. 34B shows an optical system in which a prism-like member (element in FIG. 1 of Japanese Patent Unexamined Publication No. HEI 3-248695 (248695/1991)) in which one face is a planar face, and the other face is formed into an angular form is arranged together with a lens.

These elements are arranged in the optical path, whereby an imaging optical system forms a double image of an object on an image face. In the image face under a focus state, if any one of the elements is used, there can be acquired the same effects or advantages. Specifically, the point is imaged as two points which are separated from each other vertically and, that is, from respectively a double image. However, if it comes into a defocus state, they are different in function from each other. In order to see the defocus state, the imaging states at positions which are out of the image face forwardly and rearwardly (positions space±L, for example, from the imaging face at the focus position) should be seen.

Specifically, in FIG. 34A and FIG. 34B, the image at a position which is spaced±L from the position of the imaging face forms circles shown below arrows, respectively. The magnitude of the circles shows a standard or level of the defocus state. The larger the magnitude of the circles, the more the defocus is conducted.

In the arrangement illustrated in FIG. 34B, the luminous flux which is diffracted by the inclined face of the prism is imaged on the side opposite the optical axis. For example, in FIG. 34B, the light upper the optical axis is imaged on the low side of the optical axis in the image surface. However, since the luminous flux from the upward portion of the optical axis and the luminous flux from the downward portion of the optical axis are intersected with each other, a state exists in which the light is gathered to a relatively narrow region in the vicinity of the optical axis.

For this reason, there is the case where separation of the image is not conducted in keeping with the defocus (or becomes insufficient). Thus, the function which removes a specific spatial frequency is eliminated (or becomes insufficient).

Specifically, in FIG. 34B, the image forms the double image at the defocus position which is shifted rearwardly from the focus position. However, the image forms, at the defocus position which is shifted forwardly, into a state in which the image is not separated into a double image. Thus, the low-pass filter function which removes the specific spatial frequency is eliminated.

In other words, since the form of the point image is changed by the defocus, the MTF is changed.

By contrast, since the inclined face is in a torsional relationship in FIG. 34A, the separation of the luminous flux which forms the two images is maintained also under a considerably defocused state. Accordingly, the function of the low-pass filter which removes the specific spatial frequency is not lost. Specifically, in FIG. 34A, the image forms a double image at the defocus position which is shifted rearwardly from the defocus position. The double image is similarly formed at the defocus position which is shifted forwardly. A separation distance thereof (a distance of the double image) is not almost changed. Accordingly, with respect also to the defocus image, the low-pass filter function which removes the specific spatial frequency corresponding to the double image is retained.

Accordingly, the embodiment has the function capable of preventing the moire from being generated with respect not only to a portion in which the imaged image is under the focus state, but also to a portion in which the image is imaged under the defocus state.

In other words, under the defocus state, the point image is remained to maintain two shapes, and the MTF comes into one in which influence of the defocus state is multiplied to the double image.

In the case where the multiple slant-face prism 2 having an inclined face (slant face) as is in FIG. 29A or the like is manufactured, a metallic mold is manufactured, and it is possible to manufacture the prism by plastic molding, glass molding or the like. Alternatively, the prism may be manufactured such that coating is conducted heterogeneously on a planar-face substrate.

In such a case, there are many cases where a face shape or a planar shape of the boundary portion between two slant faces (a portion encircled by a one-dot-and-chain in FIG. 37A to be described subsequently) of the single-face multiple slant-face prism 2 does not come into a shape in accordance with a design value, but comes into a disturbed one. In the disturbed portion, the low-pass filter function is reduced, and flare is generated by the fact that the light passes through the disturbed portion. To be described subsequently, in order to prevent the same from occurring, material which is impermeable to the light is applied to the disturbed portion, for example, so that a counterplan such as a light shielding portion or the like is conducted.

In the case where the multiple slant-face prism 2 is used in the television camera 6 (or a VTR camera for public welfare, a general TV camera or the like) which is mounted on the hard endoscope 5, it is desirable that at least one of conditional expressions (9)~(28) to be described subsequently is satisfied. The modification of the tenth embodiment is arranged as follows. That is, the setting is made so as to satisfy these conditional expressions. Even in the case where the moire or the like is generated by the sampling cycle or period or the like even under the defocus state, the moire or the like can be effectively removed.

In this case, in order to conduct expression by the conditional expression, a magnification or scale factor βr, a distance d of the double image, or the like is defined as follows:

βr . . . a scale factor of a lens between the multiple slant-face prism 2 and the imaging face (here, the solid-state image pickup element 8);

Sf . . . a distance, from the multiple slant-face prism 2, of the image which is formed by a lens located forwardly more than the multiple slant-face prism 2 (in the figure, the right is supposed to be positive);

d . . . a distance of the double image which is formed by the multiple slant-face prism 2 (refer to FIG. 32B); and n . . . a refractive index of the multiple slant-face prism 2.

In connection with the above, the distance Sf is a distance to an object in the case where, in FIG. 30, there is the other lens (the ocular lens 20 of the endoscope 5, or the like) in front of the multiple slant-face prism 2, but there is nothing in front of the multiple slant-face prism 2 (the object is directly photographed).

First, in the case where the moire due to the sampling, in the horizontal direction, of the mosaic filter is removed, the following expression is acquired:

$$1/|2(n-1)\theta Sf\beta r| = (P \times M) \qquad (9)$$

The denominator of the left-hand side member in the expression (9) expresses a distance twice the separation distance of the double image in the image face, and the denominator of the right-hand side member expresses a distance of the sampling period. Setting is made such that these distances are equalized to each other, whereby the moire is removed.

In practice, the moire may be more or less retained. Accordingly, the condition of the expression (9) is relaxed, and the following expression may be satisfied:

$$0.75/(P \times M) \leq 1/|2(n-1)\theta Sf\beta r| \leq 1.5/(P \times M) \qquad (10)$$

A lower limit in the expression (10) corresponds to a frequency at which the value of the MTF comes into about 40%. Thus, as the separation distance of the image increases more than that, the MTF on the side of the low frequency decreases so that reduction of the contrast of the image becomes a problem. An upper limit corresponds to the frequency at which a value of the MTF comes into about 70%. If the separation distance decreases less than that, the function to remove the moire is reduced.

Furthermore, in the case where the moire due to the sampling of the intensity is removed, in the expressions (9) and (10), it should be put as being M=M=1.

In the case of the television camera, an electronic scope or the like of an NTSC system, the moire due to the modulation of the color signal is generated. In the case where the moire at that time is required to be removed, the frequency of the color subcarrier is 3.58 MHz. Accordingly, the following expression must be satisfied:

$$0.75 \cdot 40 \cdot 3.58/Wy \leq 1/|2(n-1)\theta Sfx\beta r| \leq 1.5 \cdot 40 \cdot 3.58/Wy \qquad (11)$$

Specifically, the following expression must be satisfied:

$$107.4/Wy = 1/|2(n-1)\theta Sfx\beta r| 23\ 214.8/Wy \qquad (12)$$

Here, 1 MHz is used as corresponding to the number of 80TV.

Figure 35:
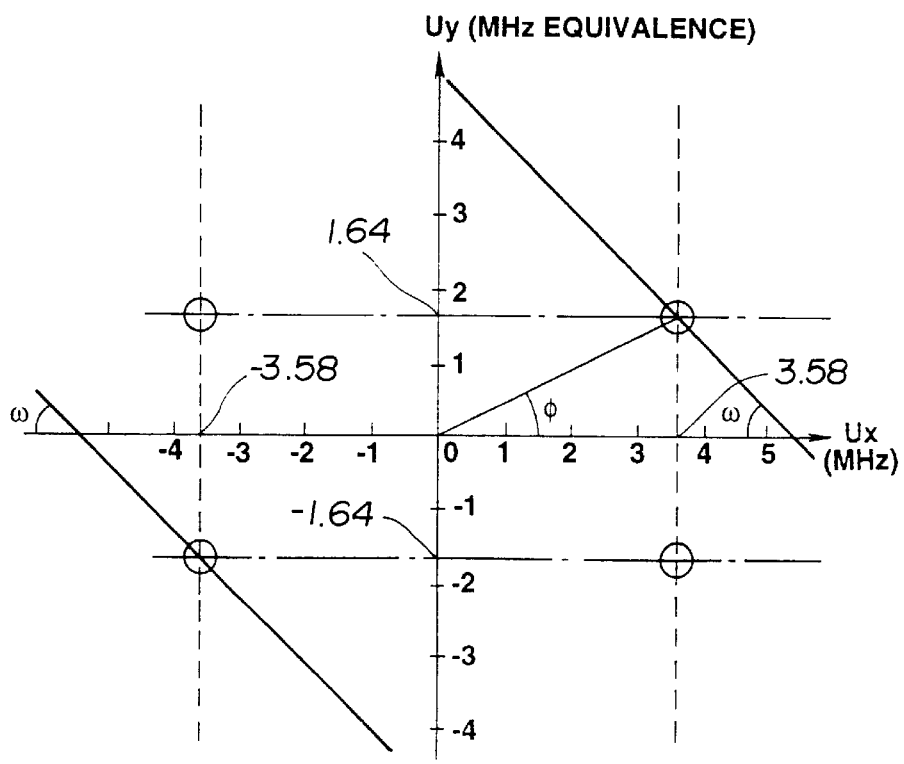

If the single-sided multiple slant-face prism 2 is put as shown in FIG. 32A, the trap line (a line in which MTF=0) enters like a broken line in FIG. 35. However, since the moire accompanied with the color modulation is generated at the round marks in FIG. 35, the trap line should pass through the point. If the division direction of the multiple slant-face prism 2 is inclined through ω+90° with respect to a horizontal direction, the trap line at that time enters like the solid line in FIG. 35. Accordingly, when the definition of φ is as follows:

When $$\phi = \text{arc tan } 1.64/3.58, \text{ that is, } 1.64/3.58 = \tan \phi, \qquad (13)$$

$$\cos(90° - \omega - \phi) \cdot 0.75 \cdot 40 \cdot A/Wy \leq 1/|2(n-1)\theta Sf\beta r| \leq \cos(90° - \omega - \phi) \cdot 1.5 \cdot 40A \qquad (14)$$

Here, A is $\sqrt{(1.64 \cdot 1.64 + 3.58 \cdot 3.58)}$ (here $\sqrt{(\ )}$ expresses the square root with ( )). If expressed by the square, A·A= 1.64·1.64+3.58·3.58. In this connection, it is supposed that an angle is positive when measured clockwise from a coordinate axis.

If rewritten, the expresses (14) becomes the following:

$$\sin(\omega+\phi)118.136/Wy \leq 1/|2(n-1)\theta Sf\beta r| \leq \sin(\omega+\phi)236.27/Wy \qquad (15)$$

This expression should be satisfied. Specifically, the division direction (the direction of the boundary line 1) or the like is set such that the condition of the expression (14) or (15) is satisfied, whereby it is possible to remove the moire due to the color modulation. In this connection, in FIG. 35, Ux and Uy indicate spatial frequencies in an X-direction and in a Y-direction in the image face (in this case, the photoelectric conversion face of the solid-state image pickup element 8).

The above-described trap line will supplementarily be described. Like an electrical circuit, in an optical system, the relationship between the spatial frequency (repetition number of the brightness and the darkness of the object (image) per 1 mm) and the strength or intensity is said to be frequency characteristics. A graph which expresses the frequency characteristics is called an MTF (Modulation Transfer Function).

In the case of a lens, differentiated from the electrical signal, consideration is made to a frequency planar face, since the object (image) corresponding to the signal is two-dimensional. FIG. 35 shows the frequency planar face. A coordinate axis showing the dimension of magnitude of the frequency response is a direction which is perpendicular to the sheet of paper. Accordingly, the dimension of the frequency response in each of the frequencies is unknown in FIG. 35. What is the trap line is a line which connects points where the MTF=0, to each other, that is, points where the frequency response comes into zero, to each other.

In connection with the above, in the case of a TV camera of a PAL system, or the like, 3.58 MHz in the expression (11) or the expression (14) should be replaced by 4.43 MHz.

In the case of an image pickup device such as a television camera of a high dignity television (abridged as "HD-TV"), an electrical scope or the like, the number of effective samples per one line (scanning line) is determined as being 1920. Accordingly, if the following expression is satisfied (refer to Television Technical Paper P. 20, January, 1991), $$0.75 \cdot (1920/Wx) \leq 1/|2(n-1)\theta Sf\beta r| \leq 1.5 \cdot (1920/Wx) \qquad (16)$$

it is possible to remove the moire of the intensity digital sampling. The number of color digital samples is determined to be 960 in order to remove the moire of the color-signal sampling (refer to the above Television Technical Paper) and, accordingly, the following relationship should be satisfied:

$$0.75 \cdot (960/Wx) \leq 1/|2(n-1)\theta Sf\beta r| \leq 1.5 \cdot (960/Wx) \qquad (17)$$

In the case where the number of horizontal pixels npx of the solid-state image pickup element 8 is insufficient with respect to 1920, the following relationship should be multiplied to the left- and the right-hand terms to the expressions (16) and (17):

$$npx/1920 \tag{18}$$

In the present specification, case of the expression (18) means, in an abridged manner, an inequality in which npx/1920 is multiplied to the expression (16) or the expression (17).

Figure 36:
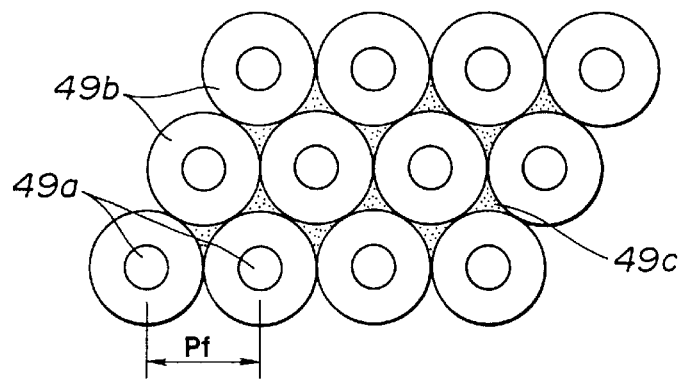

In order to use the fiber scope in which an image guide due to a fiber bundle in which fibers serving as a pixel transmission unit are arranged two-dimensionally is regularly arranged in image transmission means, and to use the multiple slant-face prism 2 for moire removal when combined with an electronic image pickup system such as a TV camera or the like, conduction is made as follows. Specifically, as shown in FIG. 36, if a fiber spacing in a fiber bundle image due to an array in which fibers are piled upon each other like a straw bag or bale, where distances between the adjacent fibers are equal respectively to each other, is Pf (in this case, a real image on the solid-state image pickup element 8 should be considered as an image), the following expression should be satisfied:

$$0.75/(Pf \cdot \sin 60°) \leq 1/|2(n-1)\theta Sf\beta r| \leq 1.5/(Pf \cdot \sin 60°) \tag{19}$$

In the case where some fiber scopes and the electronic image pickup system are combined with each other, an approximate mean value of Pf of any fiber scope or Pf of each fiber scope should satisfy the expression (19). This can be applied to Pf of expressions (29), (30) and (31) to be described subsequently.

If $$Uo=1/|2(n-1)\theta Sf\beta r| \tag{20}$$

the MTF is given by the following expression:

$$MTF = \cos(U/U0 \cdot \pi/2) \tag{21}$$

Accordingly, if the sign of equality of the expression (19) is held, the MTF in the frequency 1/(Pf·sin 60°) at that time becomes 0.5, and it is possible to restrain the moire to a value equal to or less than the half.

In FIG. 36, the fiber bundle image is an image of a fiber bundle end face which is imaged by the lens. The end face is one in which the fibers, for example, are collected regularly and fixed by an adhesive agent or the like.

In this case, the periphery of each of core parts 49$a$ which are indicated by circles in each of the fibers is coated by a corresponding one of clad parts 49$b$ have a lower refractive index than the core parts 49$a$, and adjacent clad parts 49$b$ are fixed to each other by an adhesive agent 49$c$. Reflection is made at a boundary face between the core parts 49$a$ and the clad parts 49$b$ so that each pixel is transmitted. Accordingly, the light transmission unit comes into the core parts 49$a$, and the clad parts 49$b$ and the adhesive agent 49$c$ portion surrounding the same come into a non-light transmission part. In the figure to be shown subsequently (FIG. 45B or the like, for example), in order for simplification, the fibers are shown only by the core parts 49$a$.

In the case where the multiple slant-face prism 2 as shown in FIG. 29A is manufactured, there are many cases where a metallic mold is prepared, and the prism is formed by a plastic molding or a glass molding. Alternatively, the arrangement may be such that the coating is non-uniformly conducted onto a planar-face substrate to manufacture the multiple slant-face prism 2.

In such time, the face shape of a boundary portion (a portion encircled by a one-dot-and-chain line in FIG. 37A) of the two slant faces of the multiple slant-face prism 2 does not form the designed shape, but forms instead a disturbed one. If an area which is occupied by Sm (a portion encircled by a broken line in FIG. 37A), it is desirable that an area Sα (a portion in FIG. 37A to which inclinations are applied) in which the disturbed portions occupy is as follows:

$$S\alpha/Sm < 0.3 \tag{22}$$

If this is exceeded, flare is applied to the image, which has no practical value. Further, in an endoscope having optical performance of high class which uses the relay lens and the image fibers which have a large number of fibers, if the following expression is held, $$S\alpha/Sm < 0.12 \tag{23}$$

an image having superior contrast can be acquired.

The above-described fact is experimentally confirmed by the use of the single-sided multiple slant-face prism 2 shown in FIG. 29A. At this time, the maximum value of slippage or shear of the face shape of a failure portion Sα is equal to or less than 10$\mu$.

Figure 38B:
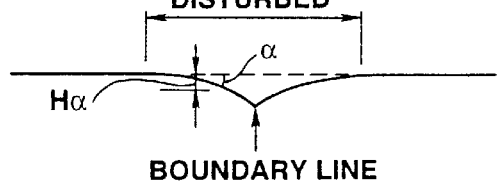
FIG. 38B is an enlarged view of a disturbed portion in a cross-section taken along A' in FIG. 38A.

FIG. 38B shows a detailed view of a portion in which the face shape is disturbed. Moreover, FIG. 38C shows a detailed view of a portion in which the face shape is disturbed whenever there is slippage between the faces.

Figure 38A:
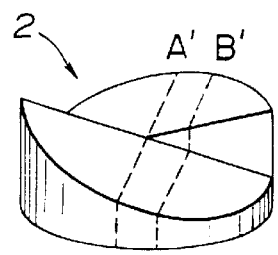
FIG. 38A is a perspective view of a single-sided multiple slant-face prism.
Figure 38C:
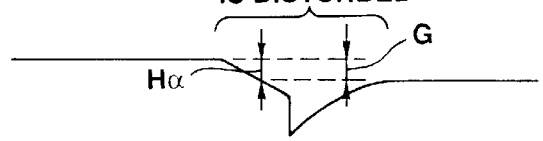
FIG. 38C is an enlarged view of a disturbed portion in a cross-section taken along line B' in FIG. 38A.

FIG. 38B shows a cross-section taken along a line A' in FIG. 38A, for example, FIG. 38C shows a cross-section taken along a line B'. That is, FIG. 38B shows a portion in which two inclined faces have the same height, while FIG. 38C shows a portion which is different in height therefrom.

Originally, the cross-section taken along the line A' is straight. As shown in FIG. 38B, however, a recess is formed at a center thereof. Furthermore, a cross-section taken along a line B' should come into square. However, there may be a case where a corner thereof is deformed, as shown in FIG. 38C.

Figure 37A:
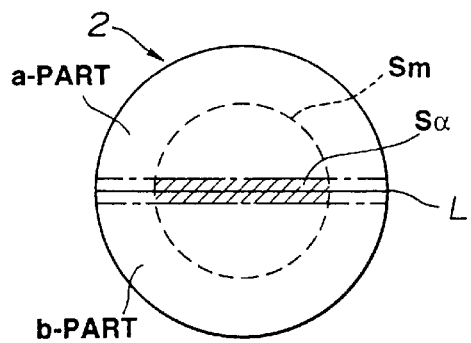
FIG. 37A is an explanatory view showing a disturbed portion in the vicinity of a boundary of a multiple slant-face prism.

First, a portion in which the face shape is disturbed in case of FIG. 37A is defined as follows:

A portion in which a shift amount of Hα from the face which is acquired by the fact that a portion which is spaced away from the boundary line extends smoothly as is follows as a mean value of the wavelength which utilizes λ is called "a portion in which the face shape is disturbed";

$$H\alpha > \lambda \tag{24}$$

Alternatively, a portion in which a portion in which an angle of α of a junction face of the point on the face, with respect to a face which is acquired by the aforesaid smooth extension satisfies the following expression is called "a portion in which the face shape is disturbed":

$$\alpha > 1° \tag{25}$$

In the case where there is a shift between the faces as shown in FIG. 38C, Hα is defined by the shift from the smooth extension of the face (broken lines in FIG. 38C). α is also similar.

It is desirable that the shift between the two faces (G in FIG. 38C) satisfies the following expression:

$$G < 10\mu \tag{26}$$

It is not preferable that, if G exceeds this value, when an object in the form of bright spots, or the like, is seen, a luminescent line appears strongly around the object.

The optical element which is used in the present embodiment is arranged such that a difference in height between the two inclined faces increases as the size of an effective diameter increases. However, when used in the endoscope, the dimension of the pupil is at the most a degree of 7 mm$\phi$. Accordingly, the dimension of the low-pass filter comes into such degree. In that case, it is preferable that the condition of the expression (26) is satisfied.

Figure 37B:
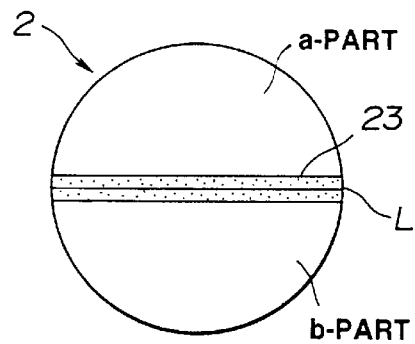
FIG. 37B is a view showing a light-shielding film which light-shields the disturbed portion in the vicinity of the boundary of the multiple slant-face prism.

In order to prevent the flare due to the fact that the light passes through the portion in which the face shape is disturbed, material through which the light passes may be attached to almost a portion of S$\alpha$ in FIG. 37A. As such material, a CrO2—Cr—CrO2 coat, a black paint or the like can be considered. The shield portion of the light may be provided at a position which substantially covers S$\alpha$, of a face opposite to the multiple slant-face prism 2. FIG. 37B shows an example in which the light shield part 23 is provided by the coat.

Figure 39:
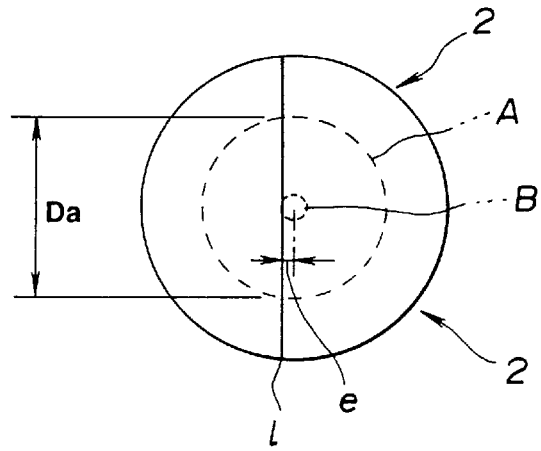

Similarly, in order to avoid the disturbance of the face shape, as shown in FIG. 39, a portion of the boundary line may be eccentric with respect to the marginal light flux. If performed in such a manner, in the case where the marginal light flux is thick in diameter, the portion S$\alpha$ in which the face shape is disturbed decreases with respect to Sm and, accordingly, there is no problem (A in FIG. 39). Further, when Sm is small (B in FIG. 39), the boundary line 1 goes out of the luminous flux. Accordingly, the moire removal function is eliminated, but it is possible to maintain the contrast of the image.

It is desirable that an eccentric amount e of the boundary line satisfies the following expression:

$$e/Da \leq 0.25 \quad (27)$$

If this is exceeded, the moire removal function is reduced even under the state of A in FIG. 39.

Figure 40:
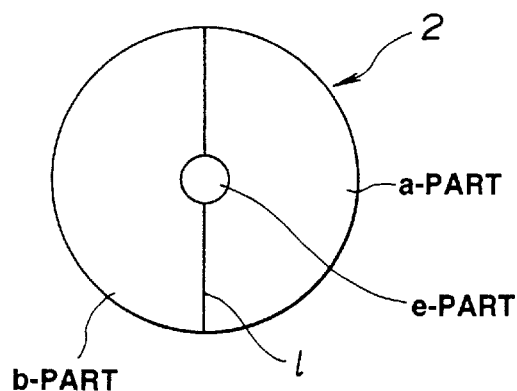

Alternatively, as shown in FIG. 40, the face may be divided into three face portion (that is, an a part, a b part and an e part in the vicinity of the center). This may be such that, when a mold of the multiple slant-face prism 2 is manufactured, only the center portion is polished or ground after polishing both faces to form the e part in which face turbulence or disturbance is removed. At this time, the boundary of division between the three face portions may not necessarily be clear.

Alternatively, a portion of the mold corresponding to the region of S$\alpha$ in FIG. 37A may be made smooth by re-polishing, grinding or the like, to remove a mold portion which is higher than the shape or form of a design value.

An example shown in FIG. 37B and FIG. 39 is particularly large or high in effect, in the case of being combined with a television camera in which the pupil diameter varies, an electronic scope, an adaptor, a hard endoscope, a fiber scope or the like.

Figure 41:
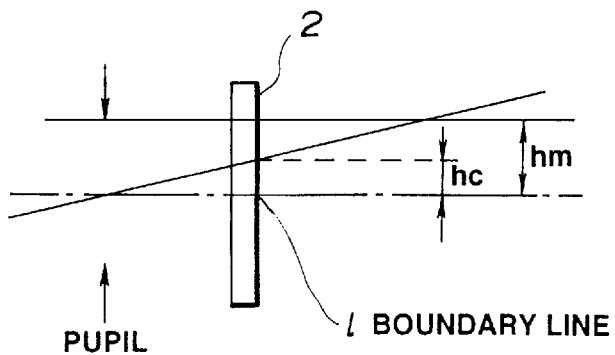

It has already been described that, in the case where the multiple slant-face prism 2 is placed in the optical system, the multiple slant-face prism 2 should be placed adjacent to the pupil. However, this will be considered in further detail.

hm and hc in FIG. 41 are a marginal light-ray height and a main light ray height of a light ray out of an axis in the multiple slant-face prism face of the multiple slant-face prism 2, respectively. Here, it is desirable that the following expression is satisfied:

$$|hc/hm| < 0.8 \quad (28)$$

If hc increases over the expression (28), a ratio of the area in which the light ray out of the axis passes through two faces of the multiple slant-face prism 2 is largely differentiated, so that the moire removal function is reduced. Even in the case where the expression (28) is not satisfied, if the multiple slant-face prism 2 is moved and is set to a position adjacent to the pupil, it is possible to satisfy the expression (28). Thus, it is desirable that the multiple slant-face prism 2 is set in the vicinity of the pupil.

In connection with the above, the multiple slant-face prism 2 may not be perpendicular to the optical axis O, and may be inclined ten degrees or more in order for the ghost removal.

According to the modification of the tenth embodiment, described above, there can be provided the following advantage. That is, setting is made so as to satisfy the conditional expression of moire removal. Thus, with respect also to the case where the moire is generated in keeping with the array of the pixel of the solid-state image pickup element 8, the sampling cycle or the like, the single-sided multiple slant-face prism 2 provided with the slant face in the torsional relationship is employed, which is high in optical low-pass filter function. Accordingly, with respect to the image which is imaged onto the image pickup face of the solid-state image pickup element 8 under the focus state or condition, but also with respect to the image which is imaged under the defocus condition, it is possible to sufficiently remove the moire (which is higher in moire removal function than a point-symmetry optical filter which is disclosed in Japanese Patent Unexamined Publication No. HEI 3-248695 (248695/1991)).

Accordingly, the endoscope image which is displayed on the color monitor 37 is superior in image quality in which the moire is removed. Further, it can be realized at a lower cost than the case where a quartz filter is used.

The double-sided multiple slant-face prism 1 which can increase the filter function more than the single-face multiple slant-face prism 2 and the endoscope apparatus according to the tenth embodiment which uses the double-sided multiple slant-face prism 1 will subsequently be described.

Figure 28A:
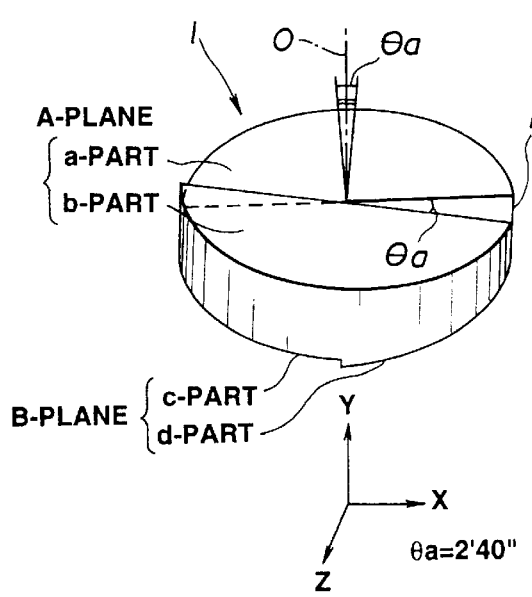
Figure 28B:
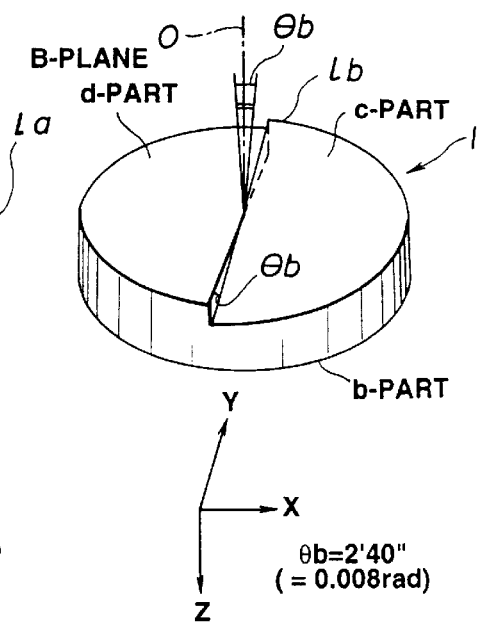
Figure 28C:
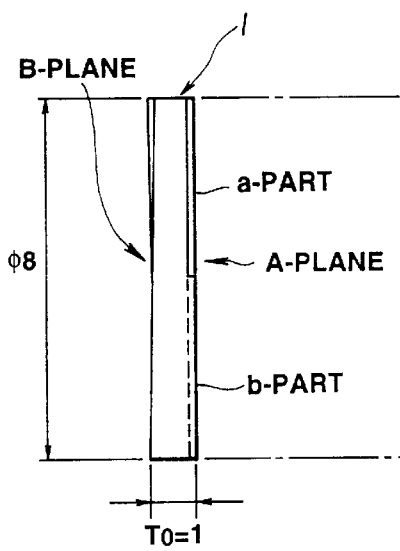
FIG. 28C and FIG. 28D are views respectively showing a side face or elevation and a front face or elevation of the double-sided multiple slant-face prism.
Figure 28D:
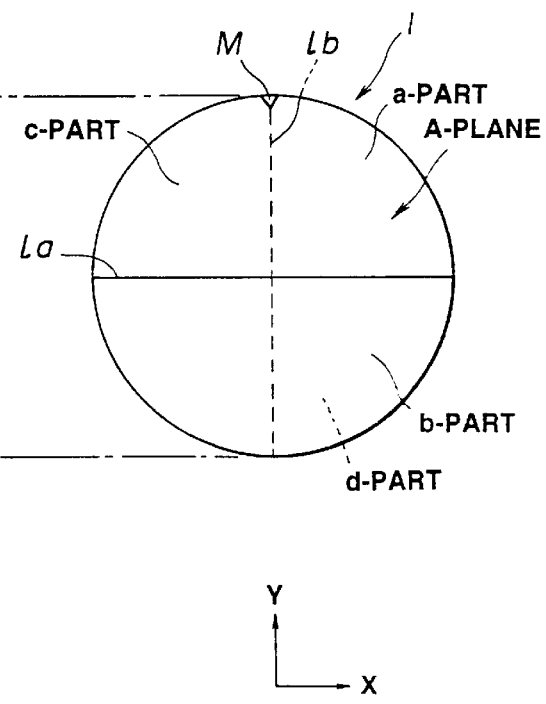

FIGS. 28A~28D show the double-sided multiple slant-face prism 1 which is used in the tenth embodiment of the invention. Similarly to the B side of the single-sided multiple slant-face prism 2, the double-sided multiple slant-face prism 1 has, on both sides thereof, two divided faces which are twisted like a propeller. Specifically, as shown in FIG. 28A, the A side of the double-sided multiple slant-face prism 1 has the a part and the b part of the two slant faces which almost use commonly the optical axis O, similarly to the single-sided multiple slant-face prism 2. The a part and the b part are formed semi-circularly, respectively, on both sides of the boundary line 1a which passes perpendicularly thereto. Moreover, as shown in FIG. 28B, in the other B side, the c part and the d part of the two slant faces commonly use almost the optical axis O, similarly to the single-sided multiple slant-face prism 2, and are formed semi-circularly, respectively, on both sides of the boundary line 1b which passes perpendicularly thereto. Furthermore, as shown in FIG. 28D, the boundary line 1a on the side of the A side and the boundary line 1b on the side of the B side are formed so as to be almost perpendicular to each other.

Normal lines which are almost elected respectively at centers of the two slant faces in the A side are in the torsional relationship, and are inclined only through an angle $\theta$a. Also on the B side, normal lines which are almost elected respectively at centers of the two slant faces are in the torsional relationship, and are inclined only through an angle $\theta$b.

By forming the normal lines so as to be in the torsional relationship, it is possible also in the case of the image under the defocus state in which the pint slips down as described above to sufficiently leave the function of the low-pass filter. In FIG. 28A and FIG. 28B, the angles θa and θb are set to θa=θb=2'40", for example.

The shape data of the A side of the double-sided multiple slant-face prism 1 becomes as follows, in the case where the direction of the optical axis O is set to the Z-axis, and the X-axis and the Y-axis are set in the plane which is perpendicular to the Z-axis, for example, a direction of the boundary between the a part and the b part is set to the X-axis:

The a part is a region in which Y is zero or positive (that is, Y≧0). A plane of the a part is Z=P·X.

The b part is a region in which Y is negative (that is, Y<0). A plane of the b part is Z=−P·X. Here, a parameter P which expresses the slant face is, for example, as follows:

$$P=\tan 1'20"\neq 0.0004$$

Further, a size of the double-sided multiple slant-face prism 1 is that, as shown in FIG. 28C, a diameter is φ8, a thickness To is To=1 mm, for example, and a refractive index n is n=1.51633, for example.

In connection with the above, as shown in FIG. 28D, the mark M for judging the orientation of the optical element is applied to the A side.

In connection with the above, the angles θa and θb of the double-sided multiple slant-face prism 1 may not be equal to each other, and should suitably be selected in accordance with the range of the value of Pf of several fiber scopes combined with each other, and Px, Py, N, M or the like of the solid-state image pickup element 8.

At this time, it is desirable that the angle θa or the angle θb satisfies at least two of the expressions (9), (10), (12), (14), (15), (16), (17) and (18) in which the angle θ is replaced by the angle θa or the angle θb. The effects or advantages thereof are similar to those of the modification in FIG. 29A. It is possible that both sides have respectively different filter functions. Accordingly, it is possible to remove much more causes which decrease the image quality upon observation or the like. Thus, the advantages thereof are high as compared with the single-sided multiple slant-face prism 2. Moreover, similarly to case of the modification, cost thereof can be remarkably reduced as compared with the quartz filter which has the equivalent functional advantages.

It is desirable, setting is made such that the A side and the B side of the double-sided multiple slant-face prism 1 satisfy at least one of the expressions (22), (23), (26), (27) and (28). Advantages thereof are the same as those of the single-sided multiple slant-face prism 2 in FIG. 29A.

The MTF of the double-sided multiple slant-face prism 1 is given by the product of the respective MTFs on the single sides. Accordingly, the double-sided multiple slant-face prism 1 can increase the trap line. Thus, the low-pass filter function can increase much more.

Figure 42:
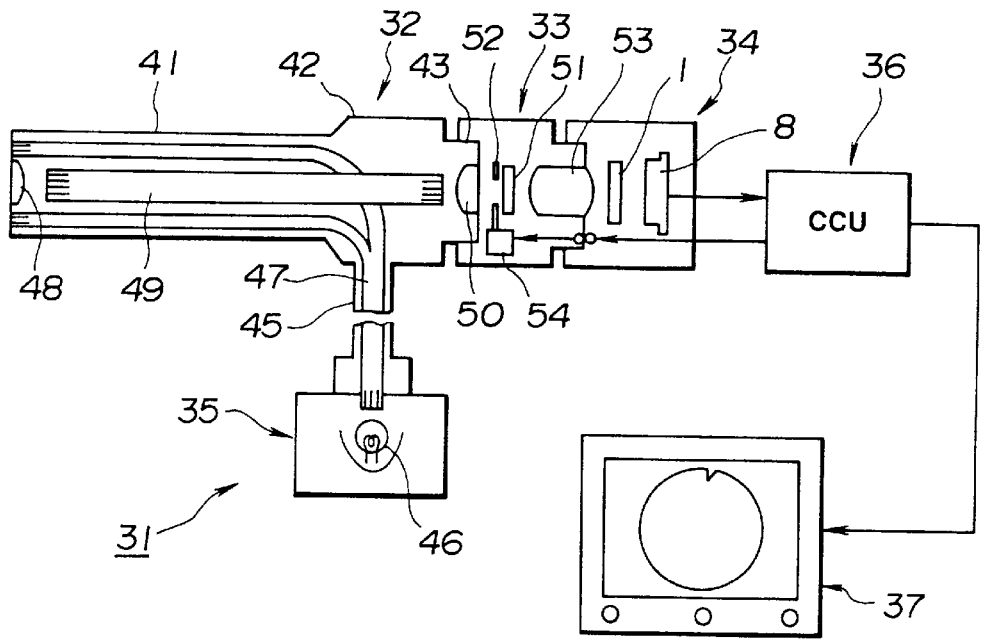

This is particularly effective in the case where the fiber scope in which the moire strongly appears and the television camera are combined with each other. FIG. 42 shows an endoscope apparatus 31 according to the tenth embodiment of the invention, which serves as an optical apparatus having such an arrangement (more particularly, an image pickup apparatus provided with image pickup function).

The endoscope apparatus 31 comprises a fiber scope 32 serving as a soft endoscope which is provided with an illumination optical system and an observation optical system, an image-pickup lens adaptor 33 which is detachably mounted on the fiber scope 32 and which has built therein an image pickup lens, a television camera 34 which is detachably mounted on the image-pickup lens adaptor 33 and which has built therein image pickup means, a light source device 35 for supplying an illumination light to illumination-light transmitting means of the fiber scope 32, a CCU 36 for conducting signal processing with respect to the solid-state image pickup element 8 such as a CCD or the like which is built in the television camera 34, and a color monitor 37 connected to the CCU 36, for displaying an image signal.

The fiber scope 32 has elasticity, and comprises an elastic elongated insertion part 41 which is inserted into a body cavity or the like, a large-width operation part 42 which is formed at a rearward end of the insertion part 41 and which is provided with curvature operation means or the like (not shown), and an ocular part 43 formed at a rearward end of the operation part 42. A light guide cable 45 extends from the operation part 43, and is detachably connected to the light source device 35.

A white illumination light of a lamp 46 within the light source device 35 supplied the illumination light to a light guide 47 within the light guide cable 45. The illumination light which is transmitted from a distal end face which is mounted on an illumination window at a distal end part of the insertion part 41 is outputted forwardly. Thus, an illumination optical system is formed which illuminates an object such as an affected or diseased part or the like.

In the distal end part, an objective lens 48 is mounted on an observation window which is formed adjacent to the illumination window so that the object illuminated by the objective lens 48 is imaged. At this imaging position, a distal end face of the fiber assembly having an image transmitting function, specifically, an image guide 49 which is formed by a fiber bundle in which, for example, fibers are bundled together, is arranged to transmit an image to a rearward-end face on the rear side by the image guide 49 which is inserted into the insertion part 41. An observation optical system is formed in which the image which is transmitted to the rearward end face can be observed by the naked eye through an ocular lens 50 which is provided at an ocular window of the ocular part 43.

In the case where the television camera 34 is mounted on the ocular part 43 through the image-pickup lens adaptor 33, the image which is transmitted by the image guide 49 serving as an image transmitting optical system is imaged on the solid-state image pickup element 8 having a color separation filter such as a mosaic filter or the like, through the ocular lens 50, an iris 52 within the image pickup lens adaptor 33, a second double-sided multiple slant-face prism 51, an image pickup lens 53, and a first double-sided multiple slant-face prism 1 which is arranged within the television camera 34. Thus, an image pickup means (or an image pickup device) is formed.

An image pickup signal which is photoelectrically converted by the solid-state image pickup element 8 is converted to a standard image signal by the CCU 36, and a color image is displayed on the color monitor 37 which serves as a color display means.

The CCU 36 generates a light modulation signal for light modulation in which, for example, an intensity or luminance signal is integrated during a period of one frame to provide a mean value of brightness, and outputs the same to an iris drive device 54 in which an amount of opening and closing of the iris 52 within the image-pickup lens adaptor 33 values. Control is carried out such that, in case where the mean level of the intensity signal is high, the iris 52 is throttled and, conversely, in the case where the mean level of the intensity signal is low, the iris 52 is opened. That is, an automatic iris control mechanism is formed. Thus, automatic control is conducted such that the brightness of the endoscope image which is displayed on the color monitor 37 always has a brightness which is suitable for observation.

The first double-sided multiple slant-face prism 1 in the tenth embodiment provides that the multiple slant-face prism faces of the A side and the B side satisfy the expression (9) (or (10)) and the expression (11) (or (12), or (14) or (15)), so as to be set to remove the moire due to the mosaic filter and the moire due to the modulation of the color signal.

Further, the second double-sided multiple slant-face prism 51 is so set that the multiple slant-face prism faces including the A side and the B side satisfy the expression (19). Moreover, the moire resulting from the fiber spacing Pf of the image of the fiber bundle is removed in a two-dimensional direction, as shown in FIG. 36.

Figure 47A:
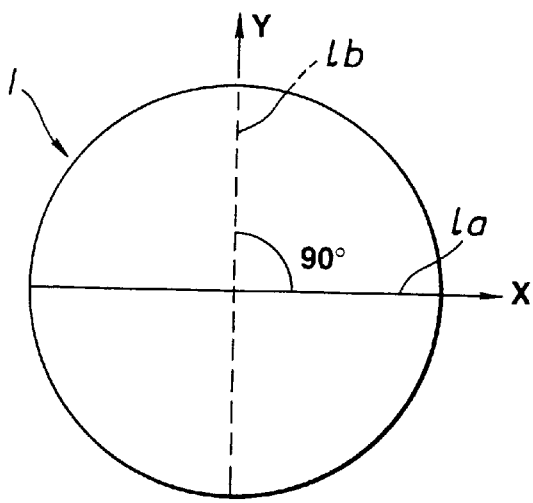
Figure 48:
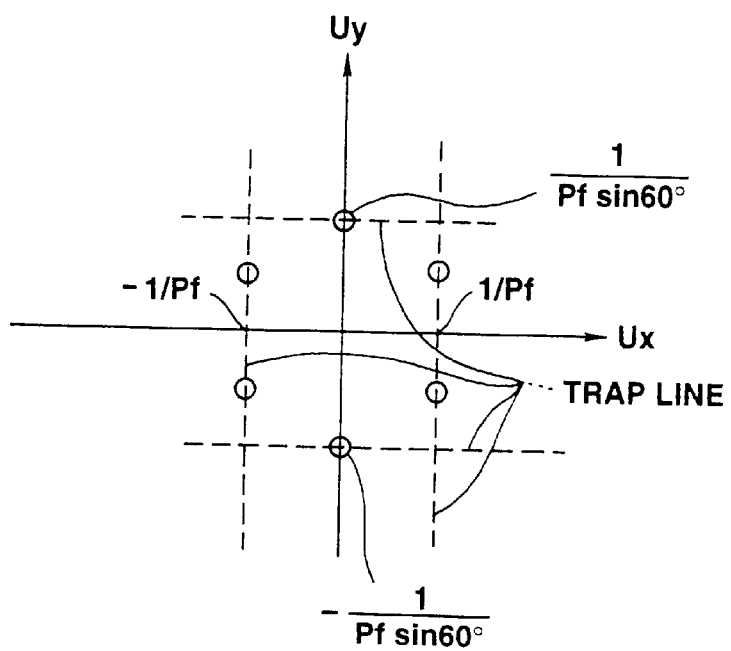

The second double-side multiple prism 51 is set as shown in FIG. 47A to be described subsequently. Setting may be made such that the trap line is set as shown in FIG. 48, to erase a clad portion in the fiber scope image in which the clad portion of each fiber is black and is conspicuous.

Furthermore, the single-sided multiple slant-face prism 2 may be used in place of the second double-sided multiple slant-face prism 51, to satisfy the expression (19).

The endoscope apparatus 31 according to the tenth embodiment, similarly to the modification which uses the single-sided multiple slant-face prism 2, sufficiently removes the moire or the like, with respect not only to the image under the defocus condition. Accordingly, there can be acquired an image having high quality, having no moire or the like, where the affected part or the like is observed.

Furthermore, in the present embodiment, since the multiple slant-face prisms are formed on both faces, causes reducing the image quality can be solved much more than the case of the modification which uses the single-sided multiple slant-face prism 2. Accordingly, images superior in quality can be acquired.

Further, it is possible to acquire similar advantages at a cost considerably less than that where the quartz filter is used.

In the first embodiment illustrated in FIG. 42, the hard endoscope 5 may be combined therewith in which the image-pickup lens adaptor 33 is exchanged, an image pickup lens adaptor 56 which is provided with a cover glass 55 is mounted in place of the double-sided multiple slant-face prism 51, and a relay lens system having low moire generation characteristics is used.

Figure 43:
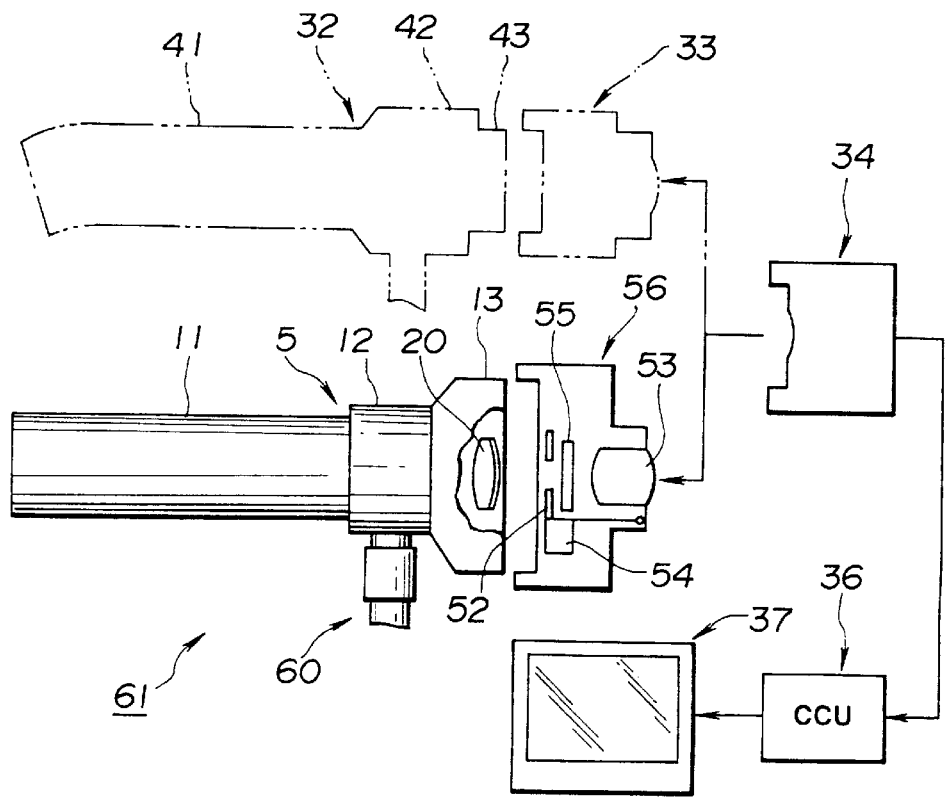
FIG. 43 is an arrangement view showing a system according to an eleventh embodiment of the invention.

By doing so, only the fact that the image pickup lens adaptor 33 is exchanged by the image pickup lens adaptor 56 can realize an endoscope apparatus 60 which is provided with the adequate low-pass filter function. FIG. 43 is an arrangement view of the endoscope system 61 according to the eleventh embodiment of the invention, which realizes such endoscope apparatuses 31 and 60 (a light source device is omitted).

In FIG. 43, an endoscope 60 is illustrated by solid lines. The endoscope apparatus 60 is constituted such that the hard endoscope 5 is used in substitution for the fiber scope 32 in FIG. 42 and, according thereto, the image pickup lens adaptor 33 is replaced or changed by the image pickup lens adaptor 56. A television camera 34 which is shared or which is used in common is detachably mounted on the image pickup lens adaptor 56.

Also, the endoscope apparatus 60 can remove the moire due to the mosaic filter and the moire due to modulation of the color signal. Thus, there can be provided an image which is high in quality. In this connection, the hard endoscope 5 is principally the same in arrangement as that shown in FIG. 30, for example.

Figure 44:
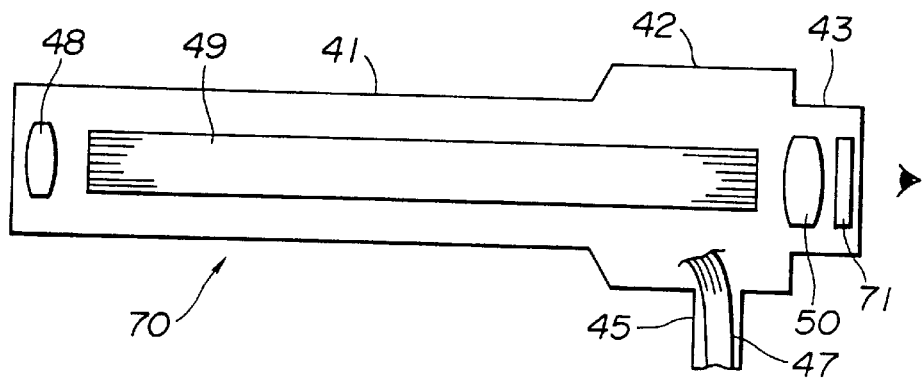
FIG. 44 is an explanatory view showing structure of a fiber scope according to a twelfth embodiment of the invention.

FIG. 44 shows a fiber scope 70 according to a twelfth embodiment of the invention. In the fiber scope 70, a double-sided multiple slant-face prism 71 is provided adjacent to the vicinity of a pupil of the ocular lens 50. The arrangement is such that setting is made such that θa and θb of the double-sided multiple slant-face prism 71 satisfy:

$$0.75/Pf \leq 1/|2((n-1)\theta a Sf\beta r| \leq 1.5/Pf \qquad (29)$$

$$0.75/Pf \leq 1/|2((n-1)\theta b Sf\beta r| \leq 1.5/Pf \qquad (30)$$

Further, an angle ψ defined between the boundary lines 1a and 1b satisfies:

$$45° \leq \psi \leq 75° \qquad (31)$$

Thus, the basic spatial frequency of the array of the fiber bundle can all be eliminated two-dimensionally. In this connection, here, βr is a scale factor or magnification of the ocular lens 50 between the multiple slant-face prism 71 and a position of an imaging face, while Sf is a distance from the multiple slant-face prism 71 of the image which is formed by the ocular lens 50 forward from the multiple slant-face prism 71.

Figure 45A:
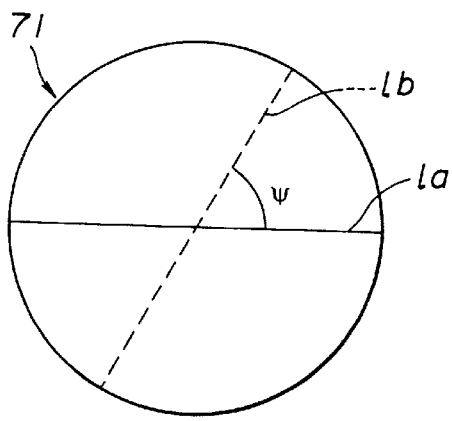
FIG. 45A is an explanatory view showing a direction of a boundary line of a double-sided multiple slant-face prism.
Figure 45B:
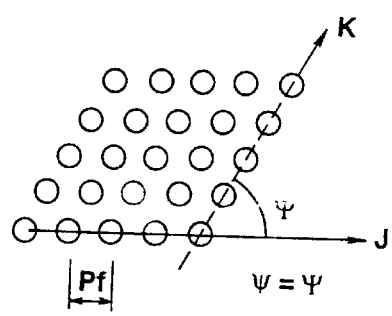
FIG. 45B is an explanatory view showing an array of a fiber bundle.

Specifically, as shown in FIG. 45A and in FIG. 45B, a direction of the boundary lines 1a and 1b of the double-sided multiple slant-face prism 71 is set to extend in parallel with a row of the fiber bundle (that is, an array direction J in the horizontal direction and an array direction K in the oblique upward direction) (the boundary line 1a is in parallel with the direction J, while the boundary line 1b is in parallel with the direction K). Accordingly, an angle ψ defined between the array direction J in the horizontal direction of the fiber bundle and the array direction K in the oblique upward direction K is equal to the angle ψ defined between the boundary lines 1a and 1b (ψ=Ψ).

Figure 46:
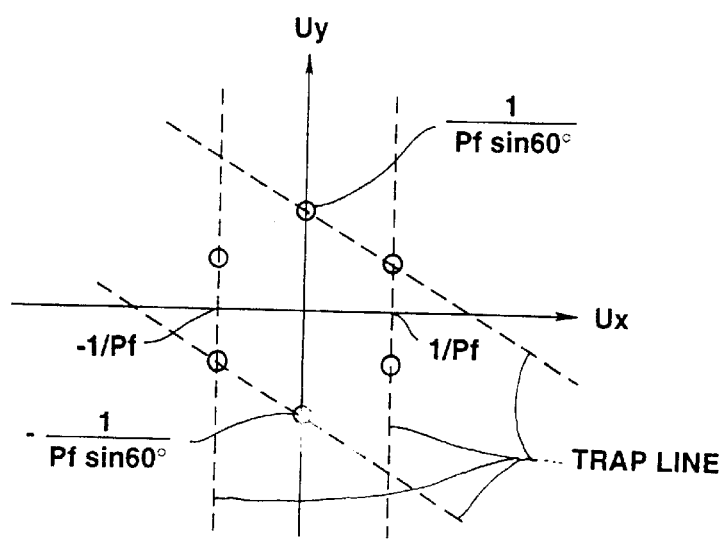
FIG. 46 is an explanatory view showing a shadow-part or dark-part removal operation of a clad part by a spatial frequency planar face, due to the twelfth embodiment.

An aspect of the spatial frequency spectrum (round marks) of the image of the fiber bundle and the trap line (the broken line) due to the double-sided multiple slant-face prism 71, at this time, is shown in FIG. 46. In this connection, in the case where the image fibers are arranged in a random array, a mean value should be taken as Pf.

Alternatively, in FIG. 44, the arrangement may be the arrangement of the first modification (of the eleventh embodiment) which utilizes the double-sided multiple slant-face prism 1 shown in FIG. 28A in place of the double-sided multiple slant-face prism 71.

Figure 47B:
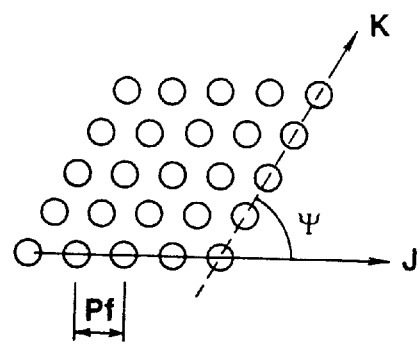
FIG. 47B is an explanatory view showing an array of a fiber bundle.

Specifically, the double-sided multiple slant-face prism 1 shown in FIG. 28A or the like in which the boundary lines 1a and 1b extend perpendicularly to each other as shown in FIG. 47A may be arranged such that the boundary line 1a is made parallel to J, with respect to the array of the fiber bundle in FIG. 47B. At this time, one of the angles θa and θb should satisfy the expression (29) or the expression (30). The remainder of the angles θa and θb should satisfy an expression in which θ in the expression (19) is displace or replaced by θa or θb.

An aspect of the spatial frequency spectrum (round marks) of the image of the fiber bundle and the trap line (the broken line) due to the double-sided multiple slant-face prism 1, at this time, is shown in FIG. 48.

As shown in FIG. 48, since the basic frequency of the fiber bundle can drop down to the vicinity of 0, the non-light transmission part such as the clad part or the like is not conspicuous, and the moire which is combined with the TV camera is also not conspicuous. If the basic frequency of the fiber bundle cannot drop down to one in the vicinity of 0, the non-light transmission part comes into a conspicuous dark part which is black, within the visual field or within the image, and the image quality is reduced or lowered. However, if the MTF of the basic frequency of the fiber bundle can be set to one in the vicinity of 0 in this manner, it is possible that the non-light transmission part or the dark part such as the clad part or the like is not conspicuous.

In connection with the above, in FIG. 35 or FIG. 46 and FIG. 48, the trap line in which the MTF of the multiple slant-face prism comes into 0 is in parallel to the X-axis or the Y-axis. However, the trap line may not necessarily be in parallel with the X-axis or the Y-axis in order to remove the moire when the television camera is mounted on the fiber scope, to remove the dark part of the clad part, or to remove the dark part of the clad part upon observation by the naked eye by the fiber scope.

Figure 49A:
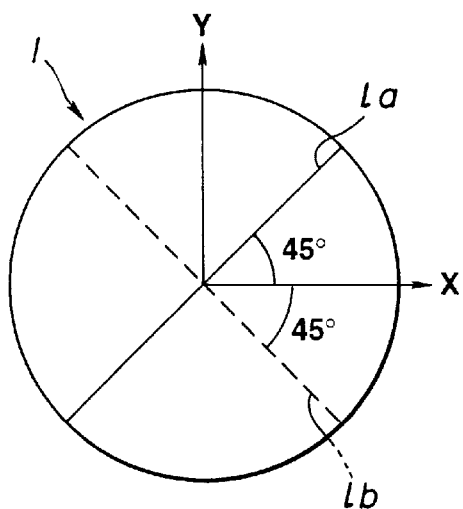
FIG. 49A and FIG. 49B relate to a second modification of the twelfth embodiment, FIG. 49A being an explanatory view showing a direction of a boundary line of a double-sided multiple slant-face prism.
Figure 49B:
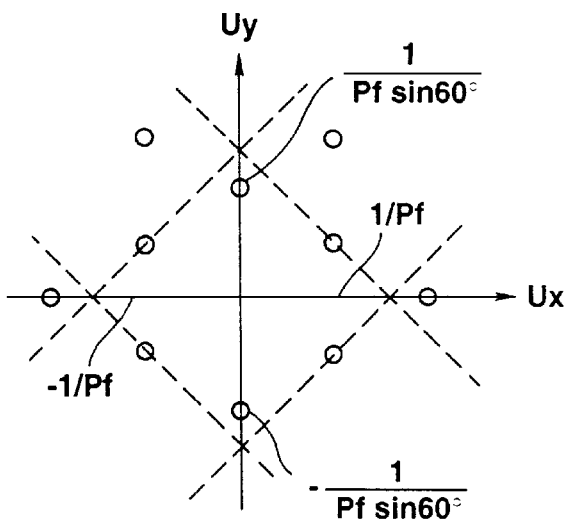

As shown in FIG. 49A, the boundary lines 1a and 1b should be arranged ±45° with respect to the X-axis. As shown in FIG. 49B, the trap line (the broken line) should pass through the vicinity of a point (the round mark in the figure) of the basic frequency of the fiber (or a high order frequency thereof).

Figure 50:
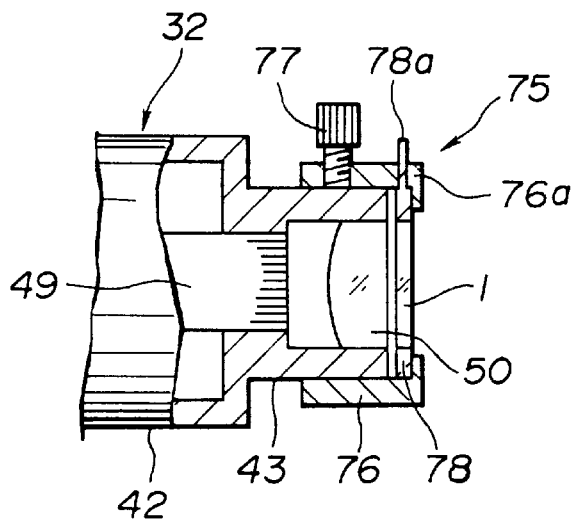

Further, the arrangement may be such as in a thirteenth embodiment of the invention shown in FIG. 50, and the removal of the dark part of the clad part upon observation by the naked eye by the fiber scope is carried out, for example.

Specifically, the arrangement may be such that, like a dark-part removing ocular adaptor 75 shown in FIG. 50, the double-sided multiple slant-face prism 1, for example, which is housed in the ocular adaptor 75 can be rotated so that the low-pass filter function is variable.

The arrangement can be such that the side of the distal end of a frame 76 in the form of a ring which serves as a mounting part for the ocular adaptor 75 is externally fitted over the ocular part 43 of the existent fiber scope (the reference numeral 32 in FIG. 43, for example), and is fixed (the ocular adaptor 75 is detachably fixed to the ocular part 43) by a fixing screw 77. A lens frame 78 to which the double-sided multiple slant-face prism 1 is mounted is fitted in an inner peripheral surface on the side of a rearward end of the frame 76 and is rotatably housed on the side of a rearward end of the frame 76.

A groove 76a is formed in the frame 76 over a range equal to or greater than 90° in a peripheral direction, and a pin 78a which is provided in projection in the lens frame 78 projects through the groove 76a. A projecting part of the pin 78a which projects from the groove 76a is rotated whereby the double-sided multiple slant-face prism 1 can be rotated.

Figure 51A:
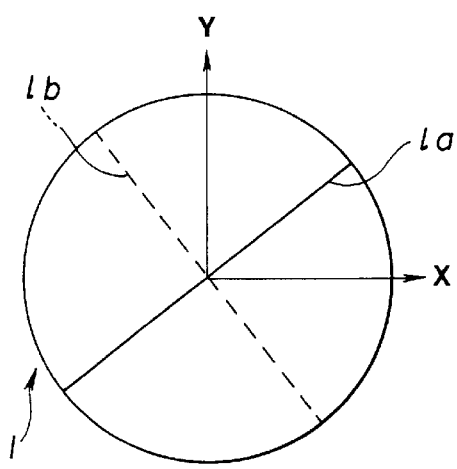
FIG. 51A is an explanatory view showing a direction of a boundary line of a double-sided multiple slant-face prism in case where the ocular adaptor is rotated.
Figure 51B:
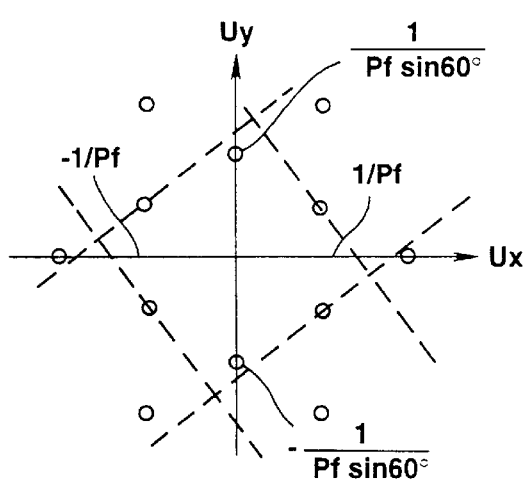

When the pin 78a is rotated 45° from a reference position (a state where the pin 78a projects in an upward direction, for example) as shown in FIG. 47A, for example, setting can be made to a state shown in FIG. 49A. As the rotation proceeds further, setting can be made to a state shown in FIG. 51A. Even under a state in which the boundary lines 1a and 1b are intersected with the X-axis with an oblique angle other than ±45° as shown in FIG. 51A, if the trap line passes through the vicinity of the frequency component (round marks in the figure) of the fiber as shown in FIG. 51B, the function of the low-pass filter appears.

According to the present embodiment, the ocular adaptor 75 is mounted on the ocular part 43 of the existent fiber scope 32, whereby the dark part such as the clad part or the like or the non-light transmission part which obstructs the observation and which decreases the image quality can be erased. Thus, an image is acquired which is adequate for observation. Such a multiple slant-face prism adaptor may be mounted on a TV camera or a TV adaptor.

Furthermore, an amount of rotation is adjusted whereby setting can be made to the image state which is most ideal for observation. Specifically, at a position of the angle which is not rotated, but is fixed (referred also to "azimuth"), there may be a case where, under a state of FIG. 47A, for example, setting cannot be made to a desirable state in which the dark part can be removed as shown in FIG. 48, or case where, under a state of FIG. 49A, setting cannot be made to a desirable state in which the dark part can be removed as shown in FIG. 49B. Even in such a case, the amount of rotation is adjusted whereby setting can be made to acquire an image which is the easiest to observe with the double-sided multiple slant-face prism 1.

In connection with the above, in the invention, what is the fiber bundle serving as the fiber assembly includes both an image guide in which optical fibers are disconnected from one another, or an image fiber in which clads of the respective optical textiles or fibers adhere to each other. Further, any of the image guide and the image fibers may be used with the fiber scope. As the image fibers, ones may be used in which the fibers are regularly arranged, or alternatively, ones may be used which are called "random fibers". What is the random fibers is one which is called generically except for such an arrangement in which fibers are the same in diameter here as each other, but the fibers are arrayed regularly, such as an arrangement in which diameters of the respective fibers which form the image guide are various, an arrangement in which, although the fibers are the same in diameter as each other, an array is irregular, or the like. Accordingly, an arrangement in which fibers of three kinds or types, for example, which are different in thickness or diameter from each other are arranged regularly like thick, middle and thin is included in the conception of the random fibers.

By the way, in the double-sided multiple slant-face prim 1, 51, 71 or the like which is provided with multiple slant-face prism parts on both faces, in the case where this is applied to all the image pickup optical systems, it is necessary to notice that refraction functions of the faces on both sides cancel each other out in the case where the angle $\psi$ defined between the boundary lines on both or opposite sides is $\psi \leq 30°$. That is, $$\psi \leq 30°, \text{ and } \theta a - \theta b = 0 \tag{32}$$

Figure 52:
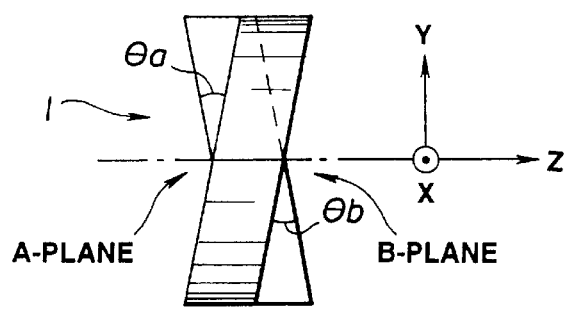
FIG. 52 is an explanatory view showing the fact that filter function is eliminated when an angle defined by a boundary line of a double-sided multiple slant-face prism satisfies a specific condition.

Here, what is a condition of $\psi=0$ and $\theta a - \theta b = 0$ indicates that $\theta a$ and $\theta b$ cancel each other out on the two faces at the time a difference of a single luminous flux, in the refraction direction, between the A side and the B side is $\psi \leq 30°$, as shown in FIG. 52.

When $\psi \leq 30°$, it is possible to select almost any value of $\theta a$ and $\theta b$.

In connection with the above, the multiple slant-face prism 2 or the double-sided multiple slant-face prism 1 may be variable in amount of eccentricity with respect to the luminous flux so that the low-pass filter function is variable.

Figure 53A:
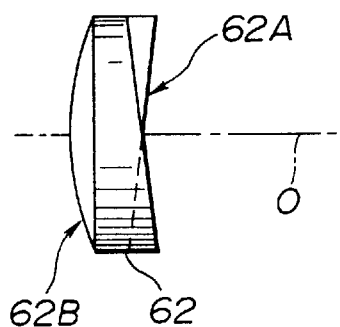
FIG. 53A and FIG. 53B are views showing a single-sided multiple slant-face lens which serves as an optical element having lens function and filter function in a fourteenth embodiment.

FIG. 53A shows an optical element 62 according to a fourteenth embodiment, which is provided both with the function of an optical low-pass filter and imaging function. The optical element 62 has the low-pass filter function by the fact that one face thereof is made to multiple slant-face prism 62A, and the imaging function by the fact that the other face is made to shape of a lens such as a normal convex lens 62B or the like. It is possible to use the optical element 62, in place of the single-sided multiple slant-face prism 2 and the imaging lens 21 in FIG. 30, for example.

Figure 53B:
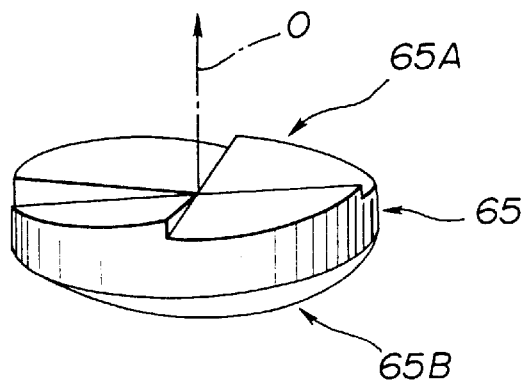

Further, as a shape or form of the multiple slant-face prism which has the advantages similar to those of the double-sided multiple slant-face prism 1, the arrangement may be such that, as shown in FIG. 53B, four faces like a multiple slant-face prism 65 which is formed, in one side thereof, with a multiple slant-face prism by four division has, in one face, a multiple slant-face prism face 65A which is twisted like a shape of a blade of a fan, and, in the other face, a normal convex lens 65B.

Specifically, the optical element 65 has a pair of two slant faces and a pair of two slant faces which are in a torsional relationship.

The optical element 65 may be used in substitution for the double-sided multiple slant-face prism 51 and the image pickup lens 53 in FIG. 42, and may be used in substitution for the ocular lens 50 and the double-sided multiple slant-face prism 71 in FIG. 44, for example.

In this manner, because the optical element 62 has both functions including the function of the optical low-pass filter and the line function, the necessity to provide a new lens is eliminated, and the need to assemble separate optical parts with each other to adjust the same may be avoided. Accordingly, as a result, costs are reduced. Moreover, less variation among products results, and the products can be made compact.

Figure 54:
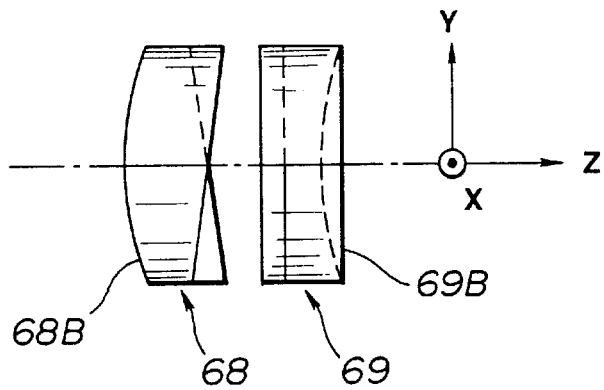
FIG. 54 is a view showing an optical system in the fifteenth embodiment.

The number of the divided faces of the multiple slant-face prism 65 is four. However, the number may be any one including three, five or the like. FIG. 54 shows an example of an optical system according to a fifteenth embodiment in which two multiple slant-face prisms 68 and 69 are so arranged that a direction in which an MTF is reduced is changed. For example, the optical system may be used in place of the double-sided multiple slant-face prism 51 and the image pickup lens 53 in FIG. 42.

The multiple slant-face prisms 68 and 69 have respective sides thereof which are multiple slant-face prism faces 68A and 69B. The normal lens faces 68B and 69B are formed respectively on the other faces thereof.

Function of the optical system in the case where two single-sided multiple slant-face prisms are arranged can almost be the same as that of the double-sided multiple slant-face prism 1 in the first embodiment in FIG. 28A, and is superior in that processing is easy, as compared with the case where they are formed respectively on both faces.

Furthermore, by the fact that the other faces which are not the multiple slant faces are made to the lens faces 68B and 69B, it is dispensed with to provide a separate lens. Further, the arrangement may be such that single-sided multiple slant-face prisms equal to or more than three are arranged side-by-side to form the optical system, and one double-sided multiple slant-face prism and one or more single-sided lens are combined with each other to form the optical system. Moreover, one single-sided multiple slant-face prism and one or more double-sided lens or lenses may be combined with each other to form the optical system.

Figure 55A:
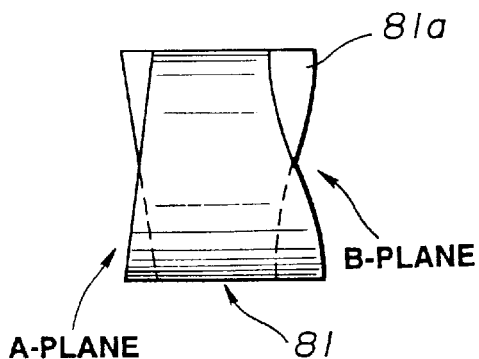
FIG. 55A and FIG. 55B are views which respectively show an optical element in a modification of the fifteenth embodiment.

The arrangement may be such that, like the optical element 63 according to a modification shown in FIG. 55A, it includes a double-sided multiple slant-face prism 81 in which a divided face of at least one face of the double-sided multiple slant-face prism 1 adjacent to the multiple slant-face prism is made to an aspherical face 81a, to control an MTF. If doing so, it is possible to universally change the low-pass filter function.

Figure 55B:
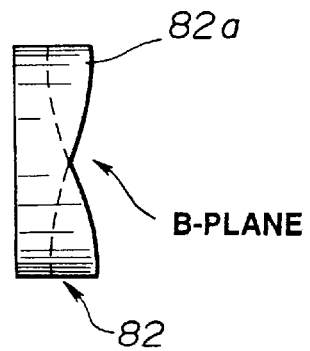

Moreover, with respect to the single-sided multiple slant-face prism 2 in FIG. 29A, the arrangement may be such that, as shown in FIG. 55B, a divided face (two inclined faces) thereof is made to an aspherical face, to control the MTF or the low-pass filter function.

Alternatively, the clad portion of the fiber scope may be eliminated, in which the clad portions of the textiles of the fibers are black and are conspicuous.

The fabrication process is difficult. However, the face on the one side may be a planar face, a spherical face or an aspherical face. Accordingly, a degree of freedom of the optical system design increases, and it is possible to bring high function. Also, in this example, at least one of the expressions (22), (23), (26), (27) and (28) can be applied, and there can be acquired the afore-mentioned advantages.

If the multiple slant-face prism in FIG. 55B is combined with the camera with an automatic iris, it is conveniently possible to change the low-pass filter function together with a change in the stop diameter.

Figure 56A:
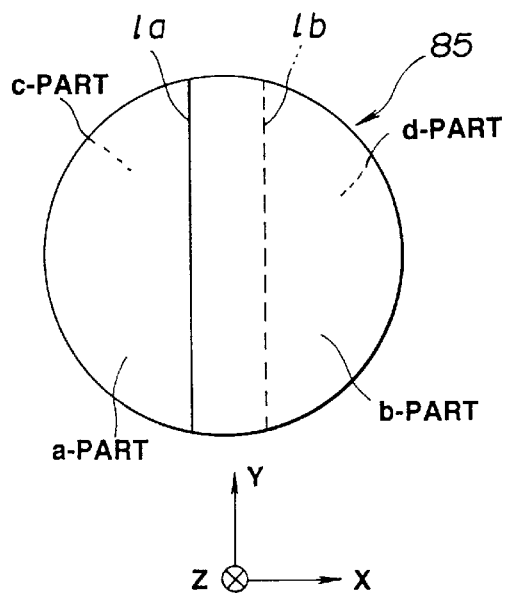
FIG. 56A and FIG. 56B are views respectively showing a front face or elevation and a side face or elevation of a double-sided multiple slant-face prism in a sixteenth embodiment.
Figure 56B:
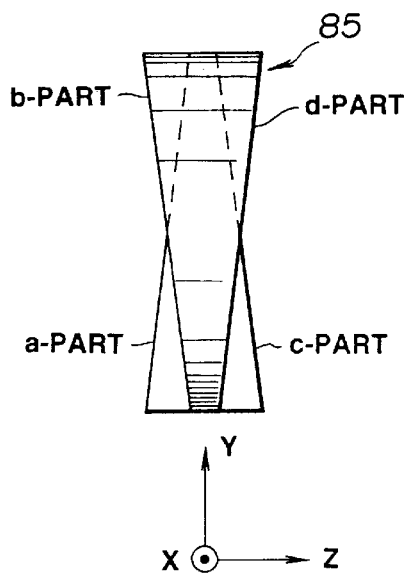

FIG. 56A and FIG. 56B show a double-sided multiple slant-face prism 85 according to a sixteenth embodiment of the invention. The double-sided multiple slant-face prism is an example of the multiple slant-face prism 85 in which boundary lines 1a and 1b of faces on both sides extend out of an optical axis when viewed from Z-direction, and exist in a plurality of locations, in which, when a luminous flux is thick in size, the luminous flux is divided in to three and is imaged. Alternatively, in a combination of optical systems, when a luminous flux is thin in size, the luminous flux is not divided. Accordingly, the double-sided multiple slant-face prism 85 is superior in that the low-pass filter function can be changed by an iris or stop diameter.

In connection with the above, the face on the one side may be divided into three or more.

Figure 57A:
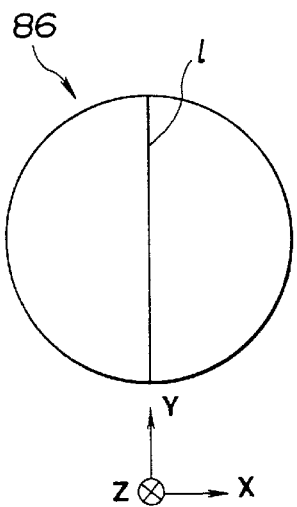
FIG. 57A to FIG. 57D relate to a seventeenth embodiment, FIG. 57A to FIG. 57C showing respectively a front face or elevation, a side face or elevation and a bottom face or elevation of a single-sided multiple slant-fact prism in the seventeenth embodiment.
Figure 57B:
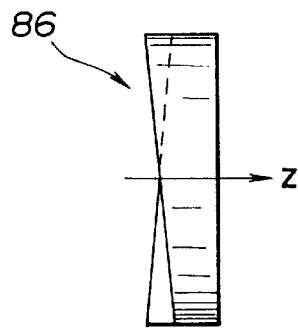
Figure 57C:
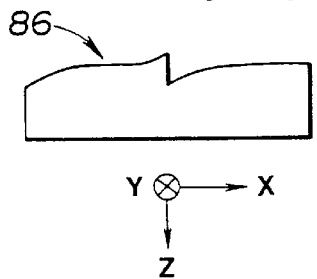
Figure 57D:
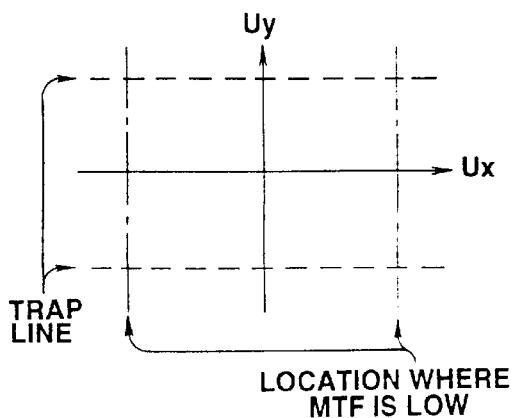

FIG. 57A~FIG. 57C show a single-sided multiple slant-face prism 86 according to a seventeenth embodiment. The multiple slant-face prism 86 is made to an aspherical face in order to increase the number of traps. Thus, spatial frequency characteristics are realized as shown in FIG. 57D.

The multiple slant-face prism 86 shown in FIG. 57A~FIG. 57C is such that a cross-sectional shape is an aspherical face in a direction which is perpendicular to a dividing boundary line 1 of a face. In the modification illustrated in FIG. 29A, only one parallel set of trap lines of the MTF is acquired. However, in the embodiment, as shown in FIG. 57D, the MTF can be reduced also in a direction parallel to the boundary line 1.

The present embodiment has function to divide an image of a dish in to a plurality of ones substantially at that portion. Accordingly, a face may be an aspherical face which has a point of inflection on the way, for example, an aspherical face of a multiple optical axis as shown in FIG. 58A, an angular aspherical face as shown in FIG. 57B and FIG. 57C, or the like.

FIG. 59 shows a single-sided multiple slant-face prism 92 according to an eighteenth embodiment of the invention. The single-sided multiple slant-face prism 92 is an example having four divided faces. The embodiment is different from that shown in FIG. 29A or FIG. 53B in that a step cannot be formed at a boundary. It is desirable that the embodiment satisfies at least any one of the expressions (22), (23), (27) and (28). Two faces of the single-sided multiple slant-face prism 92, which are not adjacent to each other or which are not joined to each other, are in a torsional relationship like a propeller.

FIG. 60A and FIG. 60B show a single-sided multiple slant-face prism 94 according to a modification. The single-sided multiple slant-face prism 94 has divided faces 94a which are divided substantially in parallel to each other. Normal directions of the respective faces 94a are selected whereby it is possible to control the MTF.

It is also desirable that the modification at least satisfies any one of the expressions (22), (23), (26), (27) and (28).

In the case where the multiple slant-face prism 94 like that as shown in FIG. 60A is formed by a plastic molding, a glass molding or the like, several divided faces are desirable to be a shape illustrated in FIG. 60B so that a grindstone of die grinding is not abutted against a face which has already been ground, so as to facilitate the manufacturing.

In the above consideration, the light has been treated geometrically optically.

However, in any of the examples shown in FIG. 28A and FIG. 38A, a different in height between the divided faces is a degree of $1\mu$-several $\mu$. In such a case, wave optical consideration is required. That is, in addition to an MTF of a wedge-shaped prism, advantages like a phase filter exist on a multiple slant-face prism.

For example, FIG. 61 shows an optical path length Lo when the double-sided multiple slant-face prism 1 in the embodiment in FIG. 28A is seen from a Z-direction. A straight line indicates an equal light ray having the optical path length Lo.

$$Lo=Tz(n-1)/\lambda c \tag{33}$$

Here, Tz is a thickness of the double-sided multiple slant-face prism 1 in the Z-direction and is function of X and Y. Further, n is a refractive index of the double-sided multiple slant-face prism 1, and $\lambda c$ is a used wavelength or a mean thereof.

Specifically, Tz becomes as follows:

When $X \geq 0$ and $Y \geq 0$, $Tz=(-Y+X)P+T_o$
When $X \geq 0$ and $Y<0$, $Tz=(-Y-X)P+T_o$
When $X<0$ and $Y \geq 0$, $Tz=(Y+X)P+T_o$
When $X<0$ and $Y<0$, $Tz=(Y-X)P+T_o$ Here, To=1 mm. To indicates the thickness of the double-sided multiple slant-face prism 1 in X=Y=0.

The wave-optical MTF R(Ux', Uy') is substantially given by the following expression (34)' at this time.

Pupil function is defined as follows:

$$H(X, Y)=A(X, Y)\exp\{2 \pi Lo(X, Y)\} \tag{34}$$

A(X, Y) is amplitude transmittance of the pupil. If this pupil function H(X, Y) is used, the following expression can be acquired:

$$R(Ux', Uy')=(1/C)\int\int H(X, Y)H^+i(X-Xo, Y-Y0)dXdY \tag{35}$$

In connection with the above, integration is conducted over the entire face of the pupil. $^+i$ expresses complex conjugate of H(X, Y). Moreover, C is a constant of standardization.

$$Xo=\lambda cUx'S, Yo=\lambda cUy'S \tag{36}$$

Here, S is a distance from a face having the low-pass filter advantages after having been passed through a face having the low-pass filter advantages of the multiple slant-face prism, to an intermediate image (an image formed in the case where it is supposed that there is no lens system at the rear of the multiple slant-face prism (on the side of injection)). Spatial frequencies at the intermediate image are expressed by Ux' and Uy'.

A fiber spacing of the fiber bundle image of the intermediate image is expressed by Pf'. If Tx(X, Y) is so selected as to satisfy the following expressions in place of the expressions (19), (29) and (30), it is possible to reduce the moire combined with the fiber scope, to a value equal to or less than 50%:

$$0<R(Ux', Uy')<0.5 \tag{37}$$

$$\sqrt{(Ux'\cdot Ux'+Uy'\cdot Uy')}=1/(Pf' \sin 60°) \tag{38}$$

In connection with the above, $\sqrt{()}$ in the left-hand side member of the expression (38) expresses a square root of ( ).

With respect to all Ux' and Uy' which satisfy the expression (38), it is unnecessary to satisfy the expression (37). With respect to Ux' and Uy' which satisfy the expression (38) in the vicinity of the fundamental or basic spatial frequency spectrum of the image of the fiber bundle, the expression (37) may be satisfied.

Here, since the manufacturing error of only the fibers is a degree of few %, and a magnification error of the lens is few %, they are put together. A range of a degree of ±10% of the basic spatial frequency of the image of the fiber bundle means the neighborhood of a spectrum thereof.

Similarly, in place of the expression (10), the following expression (39) should be satisfied:

$$0<R(1/PxM, Uy')<0.5 \tag{39}$$

In connection with the above, Px' is an image size or dimension of a single pixel of the solid-state image pickup element 8 in the X-direction at the intermediate image position.

Similarly, in place of the expression (12), the following expression (40) should be satisfied:

$$0<R(40\cdot 3.58/Wy', Uy')<0.5 \tag{40}$$

Wy' is a vertical size of an effective component or portion of the solid-state image pickup element 8, which is converted into the intermediate image position.

Similarly, in place of the expression (16), the following expression (41) should be satisfied:

$$0<R(1920/Wx', Uy')<0.5 \tag{41}$$

Wx' is a horizontal size of the effective portion of the solid-state image pickup element 8, which is converted into the intermediate image position.

Similarly, in place of the expression (17), the following expression (42) should be satisfied:

$$0<R(960/Wx', Uy')<0.5 \tag{42}$$

Similarly, in the case where the number of pixels in the horizontal direction is insufficient, npx/1920 should be multiplied to a first argument of R of the expressions (41) and (42).

Function or a functional type of the optical path length Lo (x, Y) will be considered. It is preferable that astigmatism is not generated on the optical axis. For this purposed, however, Lo (X, Y) should be coincident with Lo (X, Y) when rotated through 360°/nr about the Z-axis. In this connection, nr is the natural number and satisfies the following expression:

$$nr \geq 3 \tag{43}$$

The double-sided multiple slant-face prism 1 is an example of nr=4.

As described above, the multiple slant-face prism is treated in a manner of wave optics, whereby it is possible to extract ? performance from the low-pass filter.

Figure 62:
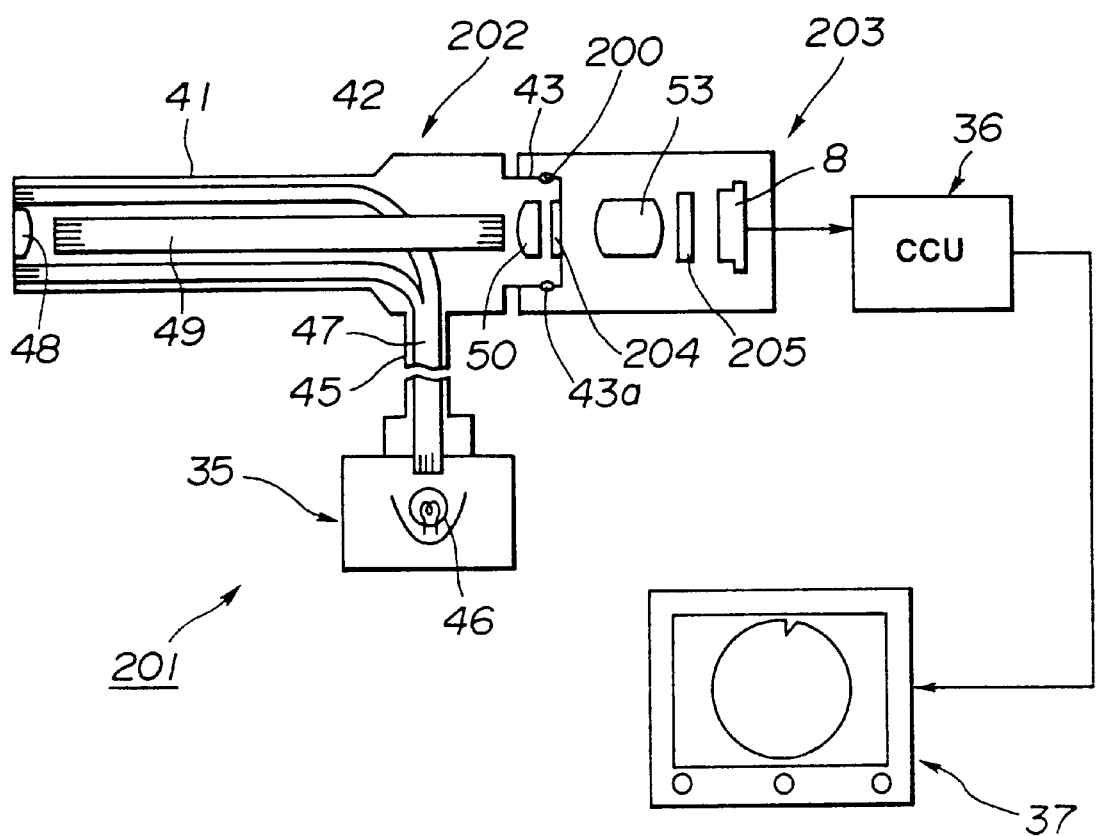
FIG. 62 and FIG. 63A relate to a nineteenth embodiment of the invention, FIG. 62 being a whole arrangement view of an endoscope apparatus according to the nineteenth embodiment.

FIG. 62 shows an endoscope apparatus 201 according to a nineteenth embodiment of the invention. The endoscope apparatus 201 comprises a fiber scope 202, a television camera 203 which is detachably and rotatably mounted on the fiber scope 202 and which has built therein the solid-state image pickup element 8, the light source device 35, the CCU 36 and the color monitor 37.

A ring-like element 43a having elasticity is mounted on a cylindrical face of the ocular part 43 of the fiber scope 202 so as to project onto a ring-like groove, for example. A ring-like recess 200 capable of housing the ring-like element 43a is provided on an inner peripheral surface of a mounting columnar opening which is provided in the television camera 203. Thus, a rotatable mounting mechanism is formed.

The television camera 203 is strongly moved in an axial direction with respect to the fiber scope 202, whereby the ring-like element 43a is elastically compressed so that it is possible to conduct mounting and demounting.

Under a mounting state in which the ring-like element 43a is fitted in the recess 200, the television camera 203 is relatively rotatable with respect to the fiber scope 202, under a state in which the television camera 203 is restricted against movement of the ocular part 43 in the axial direction.

The fiber scope 202 is arranged such that, in the fiber scope 32 shown in FIG. 42, in addition to the ocular lens 50, a double-sided multiple slant-face prism 204 is arranged on the ocular part 43 such that the basic spatial frequency component of the two-dimensional array of the fiber at the end face of the image guide 49 is removed.

Further, the phase filter 205 for removing the spatial frequency component or the sampling frequency component due to the two-dimensional array of the photoelectric conversion element of the solid-state image pickup element 8 is arranged in front of the solid-state image pickup element 8 within the television camera 203.

Specifically, in the present embodiment, the double-sided multiple slant-face prism 204 serving as an LPF of a pupil division type is arranged on one side (here, the fiber scope 32) of the fiber scope 32 which forms an image pickup device and the television camera 203 which is rotatably mounted on the fiber scope 32. The phase filter 205 serving as an LPF of a non-pupil division type is arranged on the other side.

In this manner, the LPF of the pupil division type and the LPF of the non-pupil division type are respectively provided on two devices which are rotatable relatively to each other, whereby, even if one is rotated relatively to the other, affection or influence is not exerted upon the functions of the respective LPFs.

Figure 63A:
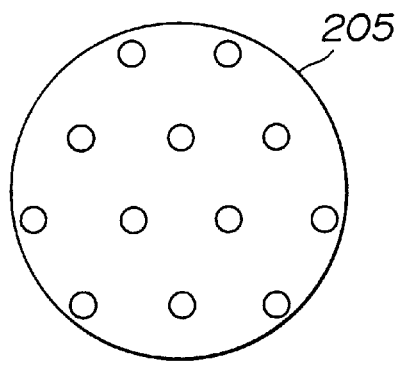

As shown in FIG. 63A, the phase filter 205 is such that a plenty of minute spot-like deposition or evaporation films 208 each having an optical path length of ½ wavelength (or a value equivalent thereto, ³⁄₂ wavelength or the like, for example) are formed on an optical element such as a transparent glass plate 207, for example. The portions on which the deposition films are formed cooperate with the portions on which the deposition films 208 are not formed, to give a phase difference of ½ wavelength. The embodiment utilizes a refraction phenomenon of the light to two-dimensionally limit the spatial frequency. The phase filter 205 may be manufactured at low cost.

The other arrangement is similar to that which has been described with reference to FIG. 42.

In the present embodiment, the spatial frequency component due to the array of the fiber on the side of the fiber scope 202 is removed by the double-sided multiple slant-face prism 204, and the spatial frequency component due to the two-dimensional array of the photoelectric conversion element on the side of the television camera 203 is removed by the phase filter 205. This function is maintained even if the side of the television camera 203 is rotated with respect to the fiber scope 202.

Accordingly, in a rotated optional mounting state, the moire can be removed under a state in which the moire is generated by the array of the fibers and the array of the photoelectric conversion element. Even under a state in which the moire is not conspicuous, the dark part or the like due to the array of the fibers can be removed. Thus, it is possible to improve the image quality.

Figure 63B:
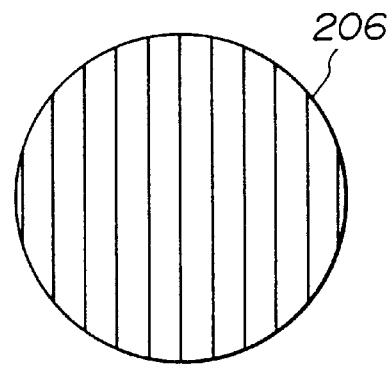
FIG. 63B is a front elevational view of a diffraction grating filter in a modification of the nineteenth embodiment.

In FIG. 62, the phase filter 205 shown in FIG. 63A is employed. However, the diffraction-grating filter 206 shown in FIG. 63B may be used as a filter of a phase type. The diffraction-grating filter 206 is such that linear grooves 209 are finely formed in a transparent glass plate 207 or in an optical element such as plastic or the like. The diffraction-grating filter 206 utilizes diffraction of the light to have function to limit one-dimensionally the spatial frequency (with respect to the frequency in a direction which extends perpendicularly to a direction of the grooves 209). The diffraction-grating filter 206 has also a merit so as to be manufactured at considerably low cost, less than the case where quartz plates are used.

Figure 64:
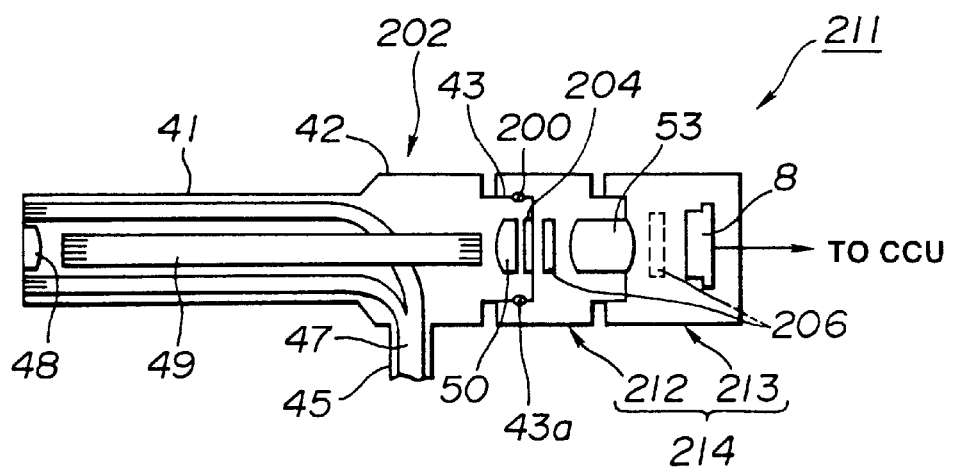
FIG. 64 is an arrangement view of a principal part of an endoscope apparatus in a twentieth embodiment of the invention.

FIG. 64 shows a principal part of an endoscope apparatus 211 according to a twenty-first embodiment. In place of the television camera 203 shown in FIG. 62, a television camera 214 is employed which comprises an adaptor 212 which is detachably and rotatably mounted on the ocular part 43 of the fiber scope 202, and a television camera body 213 which is mounted under a state which is restricted in rotation by the adaptor 212. The endoscope apparatus 211 has a single or a plurality of diffraction-grating filters 206 arranged within the adaptor 212. The diffraction-grating filter 206 may be arranged not on the side of the adaptor 212, but on the side of the television camera body 213 as indicated by a broken line in FIG. 64.

The other arrangement is the same as that in FIG. 62. Function and advantages of the embodiment are substantially similar to those of the twentieth embodiment. The phase filter 205 may be used in place of the diffraction-grating filter 206.

Figure 65:
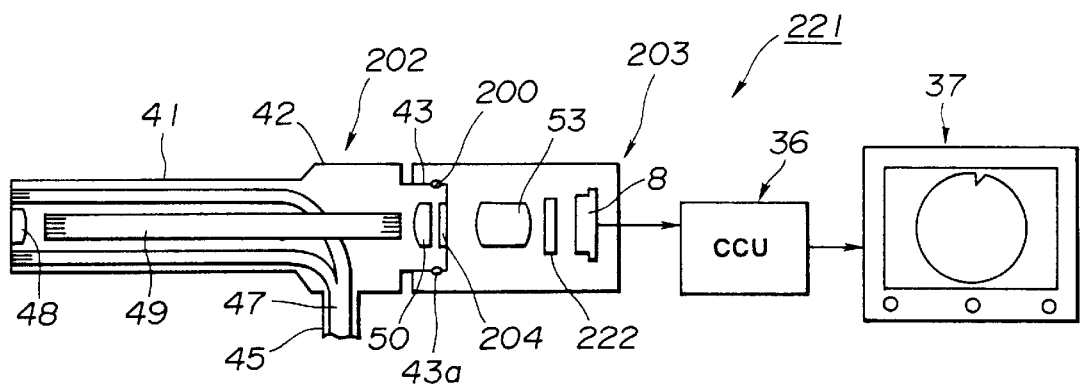
FIG. 65 is an arrangement view of a principal part of an endoscope apparatus in a twenty-first embodiment of the invention.

FIG. 65 shows a principal part of an endoscope apparatus 221 according to a twenty-first embodiment. In the present embodiment, a birefringence or double refraction LPF which is formed by a quartz plate 222 having double refraction characteristics is arranged in place of the phase filter 205 in FIG. 62. The embodiment has a higher price than the case where the phase filter 205 or the refraction-grating filter 206 is used. However, the double-sided multiple slant-face prism 204 can also be realized at a lower cost than the arrangement which is replaced by a double refraction LPF due to the quartz plates (that is, the arrangement which does not wholly use the multiple slant-face prism, but all uses the double refraction LPF.).

Figure 66:
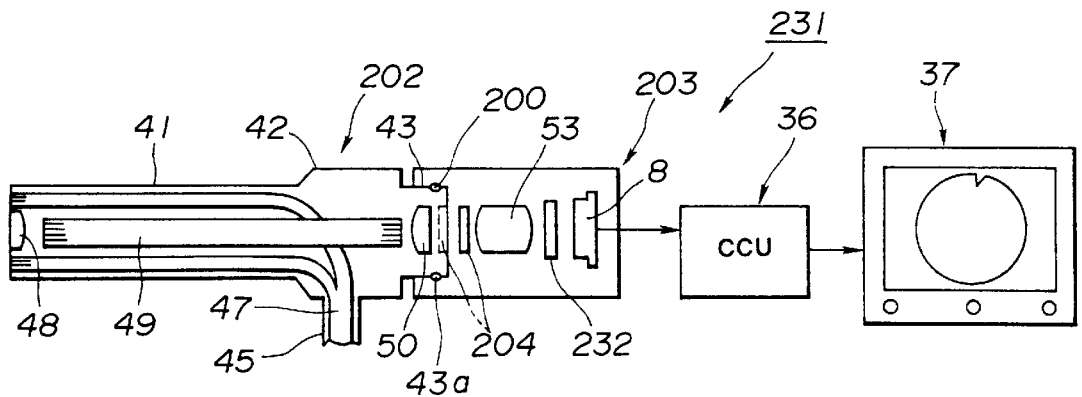
FIG. 66 is an arrangement view of a principal part of an endoscope apparatus in a twenty-second embodiment of the invention.

FIG. 66 shows a principal part of an endoscope apparatus 231 according to a twenty-second embodiment. In the present embodiment, an LPF which is formed by a double-sided multiple slant-face prism 232 is arranged in place of the phase filter 205 in FIG. 62. Moreover, the double-sided multiple slant-face prism 204 indicated by a broken line on the side of the fiber scope 202 is arranged on the side of the television camera 203. The other is similar in arrangement to FIG. 62.

Since both of the fiber scope 202 and the television camera 203 are rotatable, if the double-sided multiple slant-face prism 204 is arranged on the side of the fiber scope 202 as indicated by the broken line, there is the possibility that the LPF functions of the two respective double-sided multiple slant-face prisms 204 and 232 are cancelled out from each other, depending upon both the rotational positions.

Accordingly, in the present embodiment, the two double-sided multiple slant-face prisms 204 and 232 are arranged on one side (here, on the side of the television camera) so that the LPF function can be retained or held.

In connection with the above, the two double-sided multiple slant-face prisms 204 and 232 may be arranged not on the side of the television camera 203, but on the side of the fiber scope 202. Furthermore, for example, the arrangement may be such that, in place of the double-sided multiple slant-face prism 204, two single-sided multiple slant-face prisms are piled upon each other so that directions of the boundary lines are oriented toward different directions, or the like.

In connection with the above, embodiments or the like arranged such that the above-described embodiments or the like are combined with each other partially or the like belong to the present invention.

The invention can also be applied to an image pickup apparatus such as video scope, a TV camera or the like, and can realize the image pickup system or the image pickup apparatus, which can remove factor which reduces the image quality, such as the moire or the like, which is low in cost and which is superior in image quality.

What is claimed is:

1. An endoscope system comprising:

a first endoscope body of relay lens type having first illumination-light output means for outputting an illumination light from a distal end of an elongated first insertion part, a first object optical system provided on the distal end of said first insertion part, for focusing an image of an object which is illuminated by said illumination light, and a first image transmission optical system arranged within said first insertion part, and formed by the use of a lens which transmits said image to the rearward side of said first insertion part in a relay manner;

a second endoscope body of a fiberscope type having second illumination-light output means for outputting a second illumination light from a distal end of an elongated second insertion part, a second object optical system provided on the distal end of said second insertion part for focusing the image of the object which is illuminated by said second illumination light, a second image transmission optical system arranged within said second insertion part and formed by image guide fibers for image transmission and which transmits said image to the rearward side of said second insertion part, an ocular optical system for observing the image of the object transmitted by said second image transmission optical system, and low-pass filter means provided on a rearward end of said second image transmission optical system for optically removing moire which is generated by using said image guide fibers for image transmission;

image pickup means detachably mounted on a rearward end of one of said first and second endoscope bodies so as to be rotatable with respect to one of said first and second endoscope bodies, said image pick-up means having an imaging optical system for imaging an image which is transmitted by one of said first and second image transmission optical systems, and an image pickup element for conducting photoelectric conversion;

signal processing means for conducting signal processing with respect to said image pickup element; and image display means to which an image signal generated by said signal processing means is inputted to thereby display an image which is photoelectrically converted by said image pickup element, wherein said low-pass filter means is contained only within said second endoscope body and not contained within said first endoscope body, wherein said low-pass filter means include a multiple slant face prism arranged adjacent a diaphragm stop forming a pupil of said ocular optical system, and wherein said low-pass filter means removes moire regardless of the rotated position of said image pickup means when said image pick-up means is mounted to said second endoscope body with respect to said second endoscope body.

2. An endoscope system according to claim 1, wherein said multiple slant-fact prism has at least a pair of slant faces which are in a torsional relationship with respect to an optical axis, said multiple slant-face prism forming a multiple image.

3. An endoscope system according to claim 1, wherein said first endoscope body includes an ocular optical system for conducting observation with the naked eye in the rear of said first and second image transmission optical systems.

4. An endoscope system comprising:

a first endoscope body of relay lens type having:

first illumination-light output means for outputting an illumination light from a distal end of an elongated first insertion part, a first object optical system provided on the distal end of said first insertion part, for focusing an image of an object which is illuminated by said illumination light, and a first image transmission optical system arranged within said first insertion part, and formed by the use of a lens which transmits said image to the rearward side of said first insertion part in a relay manner;

a second endoscope body of a fiberscope type having:

second illumination-light output means for outputting an illumination light from a distal end of an elongated second insertion part, a second object optical system provided on the distal end of said second insertion part for focusing the image of the object which is illuminated by said illumination light, a second image transmission optical system arranged within said second insertion part and formed by the use of image guide fibers for image transmission which transmit said image to the rearward side of said second insertion part, an ocular optical system for observing the image of the object transmitted by said second image transmission optical system, and low-pass filter means provided on a rearward end of said second image transmission optical system for optically removing moire which is generated by using said image guide fibers for image transmission;

image pickup means detachably mounted on a rearward end of one of said first and second endoscope bodies so as to be rotatable with respect to one of said first and second endoscope bodies, said image pickup means having an imaging optical system for imaging an image which is transmitted by one of said first and an image pickup element for optical systems, and an image pickup element for conducting photoelectric conversion;

signal processing means for conducting signal processing with respect to said image pickup element; and image display means to which an image signal generated by said signal processing means is inputted to thereby display an image which is photoelectrically converted by said image pickup element, wherein said low-pass filter means is contained only within said second endoscope body and not contained within said first endoscope body, wherein said low-pass filter means includes a multiple slant face prism arranged at a position which is in a vicinity of the position of a pupil of an ocular lens at the exit side of said ocular optical system, which has a diaphragm stop forming said pupil; and wherein said low-pass filter means removes moire regardless of the rotated position of said image pickup means when said image pickup means is mounted to said second endoscope body with respect to said second endoscope body.

5. An endoscope system according to claim 4, wherein said low-pass filter means has a multiple slant-face prism having at least a pair of slant faces which are in a torsional relationship with respect to the optical axis, and said multiple slant-face prism forms a multiple image.

6. An endoscope system according to claim 4, wherein said first and second endoscope bodies have an ocular optical system for conducting naked eye observation in rear of said first and second image transmission optical systems.

* * * * *